(12) United States Patent
Loessner et al.

(10) Patent No.: US 10,174,300 B2
(45) Date of Patent: *Jan. 8, 2019

(54) POLYPEPTIDE

(71) Applicant: Micreos Human Health B.V., Wageningen (NL)

(72) Inventors: Martin Johannes Loessner, Ebmatingen (CH); Fritz Eichenseher, Zurich (CH)

(73) Assignee: MICREOS HUMAN HEALTH B.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,448

(22) Filed: Jun. 2, 2016

(65) Prior Publication Data

US 2016/0369255 A1    Dec. 22, 2016

Related U.S. Application Data

(63) Continuation of application No. 14/115,609, filed as application No. PCT/NL2011/050307 on May 4, 2011, now Pat. No. 9,382,298.

(51) Int. Cl.
| | | |
|---|---|---|
| *C07K 14/31* | (2006.01) | |
| *C07K 16/40* | (2006.01) | |
| *C12N 9/36* | (2006.01) | |
| *G01N 33/569* | (2006.01) | |
| *A61K 38/00* | (2006.01) | |

(52) U.S. Cl.
CPC ............ *C12N 9/2462* (2013.01); *C07K 14/31* (2013.01); *G01N 33/56938* (2013.01); *A61K 38/00* (2013.01)

(58) Field of Classification Search
CPC combination set(s) only.
See application file for complete search history.

(56) References Cited

FOREIGN PATENT DOCUMENTS

| WO | 2009024327 A2 | 2/2009 |
|---|---|---|
| WO | 2010002959 A2 | 1/2010 |
| WO | 2010020657 A2 | 2/2010 |

OTHER PUBLICATIONS

Becker, Stephen C. et al., Differentially conserved *Staphylococcal* SH3b_5 cell wall binding domains confer u increased *Staphylolytic* and *Streptolytic* activity to a *Streptococcal* prophage endolysin domain, Gene, Aug. 15, 2009; 143 (1-2):32-41.
Donovan, David M. et al., Peptidoglycan Hydrolase Fusions Maintain Their Parental Specificities, Applied and Environmental Microbiology, vol. 72, No. 4, pp. 2988-2996, Apr. 2006.
Kwan, Tony et al., The complete genomes and proteomes of 27 *Staphylococcus aureus* bacteriophages, Journal of Proc. Natl. Acad. Sci. U.S.A. 102 (14), 5174-5179 (2005).
Loessner, Martin J. et al., C-terminal domains of Listeria monocytogenes bacteriophage murein hydrolases determine specific recognition and high-affinity binding to bacterial cell wall carbohydrates, Molecular Microbiology, Wiley-Blackwell Publishing Ltd., GB, vol. 44, No. 2, Apr. 1, 2002, pp. 335-349.
Sass, Peter and Bierbaum, Gabriele, Lytic Activity of Recombinant Bacteriophage φ11 and φ12 Endolysins on Whole Cells and Biofilms of *Staphylococcus aureus*, Applied and Environmental Microbiology, American Society for Microbiology, US, vol. 73, No. 1, Jan. 2007, pp. 347-352.
International Search Report for Intl. App. No. PCT/NL2011/050307, dated Jan. 16, 2012.

*Primary Examiner* — Kagnew H Gebreyesus
(74) *Attorney, Agent, or Firm* — McDonnell Boehnen Hulbert & Berghoff LLP

(57) ABSTRACT

The invention relates to a polypeptide, a corresponding nucleic acid molecule, a construct and/or vector and/or cell comprising such nucleic acid molecule and/or a composition comprising said polypeptide, nucleic acid molecule, construct, vector and/or cell. The invention further relates to such composition for medical use, preferably for use in treating an infectious disease. Furthermore, the invention relates to the use of said polypeptide, nucleic acid molecule, construct, vector, cell and/or composition as an antimicrobial, preferably as a food additive or disinfectant, or for detecting bacteria, preferably in a diagnostic application.

27 Claims, 5 Drawing Sheets

Specification includes a Sequence Listing.

POLYPEPTIDE

SPECIFICATION

This application is a continuation of U.S. application Ser. No. 14/115,609, filed Jan. 6, 2014, which is a U.S. National Phase Application under 35 U.S.C. § 371 of International Application No. PCT/NL2011/050307, filed on May 4, 2011.

FIELD OF THE INVENTION

The invention relates to a polypeptide, a corresponding nucleic acid molecule, a construct and/or a vector and/or a cell comprising such nucleic acid molecule and/or a composition comprising said polypeptide, nucleic acid molecule, construct, vector and/or cell. The invention further relates to such polypeptide, corresponding nucleic acid molecule, construct and/or vector and/or cell comprising such nucleic acid molecule and/or composition for medical use, preferably for use in treating an infectious disease. Furthermore, the invention relates to the use of said polypeptide, nucleic acid molecule, construct, vector, cell and/or composition as an antimicrobial, preferably as a food additive or disinfectant, or for detecting bacteria, preferably in a diagnostic application.

BACKGROUND OF THE INVENTION

*Staphylococcus aureus* is a major human pathogen frequently implicated in several serious infectious diseases and food poisoning. Its treatment becomes more and more difficult because of emerging antibiotic resistant strains. Endolysins from phages infecting *Staphylococcus aureus* have been shown to potentially control these pathogens and can be used for their specific detection. In most cases, major obstacles in the application of endolysins targeting *Staphylococcus* species are low enzyme activity, difficult production in large quantities and/or protein stability.

There is always a need for new antimicrobials with improved characteristics on for example antimicrobial activity and/or stability.

DESCRIPTION OF THE INVENTION

Reported here is the newly characterised Ply2638, the endolysin of *S. aureus* bacteriophage Φ2638a. The enzyme and several engineered derivatives were expressed in a soluble way in *E. Coli* and showed surprising stability after lyophilisation as proven by their lytic activity after reconstitution. In addition to a cell wall-binding domain which binds the cell wall of *Staphylococcus* genera, we showed that two functional domains, i.e. an M23 endopeptidase domain and an amidase domain, are crucial for optimal lytic activity.

We showed that retrofitting of the enzyme with catalytic domains and/or duplication of the cell wall-binding domain originating from *S. aureus* Φ11 endolysin, ΦTwort endolysin, and Lysostaphin resulted in a heterologous polypeptide fusion product with an enhanced lytic activity and/or a shifted pH optimum and/or an increased stability after lyophilisation and reconstitution.

Nucleic Acid Molecule

In a first aspect, there is provided a nucleic acid molecule comprising or consisting of a first nucleotide sequence, said nucleotide sequence having 80, 81, 82, 83, 84, 85, 86, 87, 88, 89, 90, 91, 92, 93, 94, 95, 96, 97, 98, 99 or 100% sequence identity with SEQ ID NO: 12 (referred is to Table 1 for an overview of all SEQ ID NOs used herein). Preferably, said first nucleotide sequence has a length of at least 282, 285, 290, 300, 310, 320, 330, 340, 350, 360 or 370 nucleotides, more preferably, at least 381 nucleotides and/or a length of at most 510, 480, 450, 420 or 390 nucleotides. Preferably, said nucleic acid molecule has a length of at least 282, 285, 290, 300, 310, 320, 330, 340, 350, 360, 370 nucleotides, more preferably at least 381 nucleotides and/or a length of at most 4500, 4200, 3900 and/or 3600 nucleotides. Preferably, said nucleic acid molecule has a length of at least 1200, 1230, 1260, 1290, 1320, 1350, 1380, 1410, 1440, 1470, 1500, 1530 or 1560 nucleotides and/or a length of at most 4500, 4200, 3900 and/or 3600 nucleotides. Also preferred is a nucleic acid molecule according to the invention with a length of at least 1890, 1920, 1950, 1980, 2010, 2040, 2070, 2100, 2130 or 2160 nucleotides and/or a length of at most 4500, 4200, 3900 and/or 3600 nucleotides. Preferably, said first nucleotide sequence encodes a cell wall-binding domain which binds the peptidoglycan cell wall of *Staphylococcus* genera. Preferably, said first nucleotide sequence originates from *S. aureus* bacteriophage Φ2638a endolysin.

As estimated from alignments with the crystal structure of the C-terminal 92 residues of ALE-1 (Lu et al., J. Biol. Chem., 2006, 281(1):549-58), it was estimated that a minimum of 94 amino acids from the cell wall-binding domain originating from *S. aureus* bacteriophage Φ2638a endolysin may be sufficient to direct the enzyme to the cell wall of *Staphylococcus* genera.

Binding of a domain to the peptidoglycan cell wall of *Staphylococcus* genera may be assessed using assays well known to the artisan. In a preferred embodiment, an immunohistochemical technique and/or a gene fusion technique resulting in labelled constructs are used for assessing specific binding of peptides, polypeptides or proteins to the peptidoglycan cell wall of *Staphylococcus* genera. Quantification methods of signals used in the above mentioned immunohistochemical or fusion techniques are well known in the art.

In one embodiment, *Staphylococcus* peptidoglycan cell wall-binding can be quantified using a fluorescent fusion construct comprising a polypeptide comprising a domain encoded by a first nucleotide sequence. Such a cell wall-binding assay is described in detail by Loessner et al (Molecular Microbiology 2002, 44(2): 335-349) and in Example 1. In this assay a solution comprising said fluorescent fusion construct or a negative control, preferably Green Fluorescent Protein (GFP), is subjected to *Staphylococcus* cells, preferably *S. aureus* cells, more preferably *S. aureus* BB255 for an indicated time period where after the cells are sedimented by centrifugation together with the bound fluorescent fusion constructs. The fluorescent signal of the *Staphylococcus* cells exposed to a fluorescent fusion construct subtracted by the fluorescence signal of the *Staphylococcus* cells exposed to a negative control, preferably GPF, is a measure for cell binding as meant in this disclosure.

Preferably, within the context of the invention a nucleic acid molecule will be said to encode a polypeptide domain that binds the peptidoglycan cell wall of *Staphylococcus* genera when using this assay an increase in fluorescent signal of the sedimented cells above the negative control as defined herein is detected. The binding is preferably said to be specific. Preferably, the invention relates to a nucleic acid molecule encoding a polypeptide or a domain which exhibits binding as defined herein of at least 50, 60, 70, 80, 90 or 100, 150 or 200% of peptidoglycan cell wall binding of *S. aureus* bacteriophage Φ2638a endolysin (Ply2638) encoded by SEQ ID NO: 1.

In an embodiment, the invention relates to a nucleic acid molecule that has 80, 81, 82, 83, 84, 85, 86, 87, 88, 89, 90, 91, 92, 93, 94, 95, 96, 97, 98, 99 or 100% sequence identity with SEQ ID NO: 1 encoding for *S. aureus* bacteriophage Φ2638 endolysin.

The present invention further relates to a nucleic acid molecule comprising in addition to said first nucleotide sequence, a heterologous nucleotide sequence encoding a lytic domain. Preferably, said lytic domain exhibits peptidoglycan hydrolase activity as defined later herein. Said nucleic acid molecule comprising heterologous nucleotide sequences being defined herein as a "retrofitted construct".

As used herein the term "heterologous sequence" or "heterologous nucleic acid" is one that is not naturally found operably linked as neighbouring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature.

A "peptidoglycan hydrolase activity" herein also defined as a "lytic activity" can be assessed by methods well known to the artisan. In an embodiment, lytic activity can be assessed spectrophotometrically by measuring the drop in turbidity of substrate cell suspensions. Preferably, lytic activity can be assessed spectrophotometrically measuring the drop in turbidity of a *S. aureus* suspension, wherein turbidity is quantified by measuring $OD_{595}$ spectrophotometrically (Libra S22, Biochrom). More preferably, 200 nM of a polypeptide encoded by a nucleic acid molecule as identified herein is incubated together with an *S. aureus* suspension having an initial $OD_{600}$ of 1±0.05, as assessed spectrophotometrically (Libra S22, Biochrom), in PBS buffer pH 7.4, 120 mM sodium chloride for 30 min at 37° C. The drop in turbidity is calculated by subtracting the $OD_{595}$ after 30 min of incubation from the $OD_{595}$ before 30 min of incubation. Within the context of the invention a nucleic acid molecule will be said to comprise a nucleic acid sequence encoding a lytic domain when using this assay a drop in turbidity of at least 10, 20, 30, 40, 50 or 60% is detected. Preferably, a drop of at least 70% is detected. Preferably, the invention relates to a nucleic acid molecule encoding a polypeptide which exhibits a lytic activity of at least 50, 60, 70, 80, 90, 100, 150 or 200% or more of a lytic activity of *S. aureus* bacteriophage Φ2638a endolysin (Ply2638) encoded by SEQ ID NO: 1.

In an embodiment a nucleic acid molecule of the invention may not comprise or consist of SEQ ID NO:1. SEQ ID NO: 1 encodes for *S. aureus* bacteriophage Φ2638 endolysin.

A preferred embodiment encompasses a nucleic acid molecule comprising said first nucleotide sequence as identified herein and further comprising as a lytic domain a second and third nucleotide sequences, wherein said second sequence encodes an endopeptidase domain and third nucleotide sequence encodes an amidase domain. Accordingly, the invention relates to a nucleic acid molecule comprising said first nucleotide sequence, wherein said nucleic acid molecule has 80, 81, 82, 83, 84, 85, 86, 87, 88, 89, 90, 91, 92, 93, 94, 95, 96, 97, 98, 99 or 100% sequence identity with SEQ ID NO: 1, or wherein said nucleic acid molecule further comprises a heterologous nucleotide sequence encoding a lytic domain.

An endopeptidase domain as used herein preferably cleaves the pentaglycine cross-bridges (Trayer, H. R. and Buckley, C. E. (1970) *Molecular properties of lysostaphin, a bacteriolytic agent specific for Staphylococcus aureus. J. Biol. Chem.* 245, 4842-4846) that are found in the cell wall of *Staphylococcus* genera, preferably in the cell wall of *S. aureus, S. simulans* and *S. carnosus*. An amidase domain as used herein preferably hydrolyzes gamma-glutamyl-containing substrates. The functionality and activity of these domains in a polypeptide can be confirmed by characterizing the cleavage products upon incubation of said polypeptides containing any of these domains with purified peptidoglycan. Preferably, each of the nucleotide sequences encoding the second or third domain is of bacterial or bacteriophage origin. In a preferred embodiment, said second and third nucleotide sequences originate from a gene encoding for an enzyme selected from the group consisting of *S. aureus* bacteriophage Φ2638a endolysin, *S. aureus* bacteriophage Φ11 endolysin, *S. aureus* bacteriophage ΦTwort endolysin and *S. Simulans* lysostaphin. Preferably, said second nucleotide sequence has 80, 81, 82, 83, 84, 85, 86, 87, 88, 89, 90, 91, 92, 93, 94, 95, 96, 97, 98, 99 or 100% sequence identity with SEQ ID NO: 14 or 15 and said third nucleotide sequence has 80, 81, 82, 83, 84, 85, 86, 87, 88, 89, 90, 91, 92, 93, 94, 95, 96, 97, 98, 99 or 100% sequence identity with SEQ ID NO: 17 or 18.

The invention encompasses all constructs as defined herein containing the functional domains as meant in the invention at any possible location within the construct. In a preferred embodiment, a nucleic acid molecule as defined herein encodes for a polypeptide with a C-terminal domain encoded by a first nucleic acid sequence as identified herein, which is shown herein to encode for functional polypeptides able to target for *Staphylococcus* genera. Even more preferred is a nucleic acid molecule as defined herein comprising a nucleic acid molecule that has 80, 81, 82, 83, 84, 85, 86, 87, 88, 89, 90, 91, 92, 93, 94, 95, 96, 97, 98, 99 or 100% sequence identity with SEQ ID NO: 9. SEQ ID NO: 9 comprises a first nucleotide sequence encoding a C-terminal SH3b homologue cell wall-binding domain (both domains from Ply2638 encoded by SEQ ID NO: 1: Leu138-Lys486), a second nucleotide sequence encoding a polypeptide comprising an N-terminal M23 glycyl-glycine endopeptidase homologue domain (mature Lysostaphin encoded by SEQ ID NO: 33: Ala1-Gly154) and a third nucleotide sequence encoding a central amidase-2 homologue domain. It has a theoretical size of 58.266 kDa. A polypeptide encoded by SEQ ID NO: 9 differs from *S. aureus* bacteriophage Φ2638a endolysin in that the N-terminal M23 endopeptidase domain is substituted by an M23 endopeptidase domain from *S. Simulans* lysostaphin. We showed here that a polypeptide encoded by SEQ ID NO: 9 demonstrated at least 20% increased lytic activity as compared to *S. aureus* bacteriophage Φ2638a endolysin while the lytic activity is maintained after lyophilisation and reconstitution. In a preferred embodiment, a nucleic acid molecule comprising said first, second and third nucleotide sequences encodes for a polypeptide exhibiting a lytic activity of at least 0.7, 0.8, 0.9, 1.0, 1.1, 1.2, 1.3, 1.4, 1.5, 1.6, 1.7, 1.8, 1.9 or 2 fold as compared to a lytic activity of *S. aureus* bacteriophage Φ2638a endolysin encoded by SEQ ID NO:1. In a preferred embodiment, a nucleic acid molecule comprising said first, second and third nucleotide sequences encodes for a polypeptide exhibiting a decrease in lytic activity of at most 1, 2, 3, 4, 5, 6, 7, 8, 9 or 10% after lyophilisation and reconstitution as defined herein as compared to freshly prepared polypeptide, wherein "freshly prepared" is preferably defined herein as at most 2 days storage at 1.63 mg/mL in lyophilisation buffer (50 mM Tris, 500 mM sucrose, 200 mM mannitol, 0.05% polysorbate 20+50% glycerol) at −20° C. and thawed immediately before assessing lytic activity in an assay as identified herein.

Lyophilisation and reconstitution is defined herein as dehydration by freeze-drying and subsequent reconstitution of the sample by adding water. In an embodiment, lyophilisation and reconstitution may be done by dialyzing against 3 changes of 300 ml lyophilization buffer (50 mM phosphate or Tris, 500 mM sucrose, 200 mM mannitol, pH 7.4) aliquot and freezing in the gaseous phase of liquid nitrogen. The freeze-drying can be done under standard conditions, preferably at −40° C. and vacuum at 75 mTorr for 60 minutes, followed by increasing temperature during 5 hours to −10° C. and another 60 minutes at −10° C. at the same vacuum levels. As final step, temperature is preferably increased to 25° C. during 10 hours. Samples are reconstituted by the addition of water.

In another preferred embodiment, a nucleic acid molecule as defined herein comprises in addition to the above identified first, second and third nucleotide sequences at least one duplicate identical or heterologous first, second and/or third nucleotide sequence. Preferably, a nucleic acid molecule as defined herein comprises in addition to said first, second and third nucleotide sequences, a duplicate identical first nucleotide sequence. We showed here that duplication of the first nucleotide sequence as defined herein encoding a cell wall-binding domain results in a polypeptide preferably as encoded by SEQ ID NO: 20 which exposes at least 5, 10, 20, 30, 20 or 40% increased lytic activity as compared to a lytic activity of a reference polypeptide encoded by a nucleic acid molecule lacking such duplicate first domain or as compared to a lytic activity of S. aureus bacteriophage Φ2638a endolysin encoded by SEQ ID NO:1 as assessed in an assay as identified herein, more specifically using equimolar amount of a polypeptide and a modified PBS buffer containing 200, 300, 400, or 1000 nM NaCl. This embodiment also encompasses a heterologous nucleic acid molecule in which said first, second and third nucleotide sequences originate form the same source being S. aureus bacteriophage Φ2638a, said nucleic acid molecule comprising a sequence that has 80, 81, 82, 83, 84, 85, 86, 87, 88, 89, 90, 91, 92, 93, 94, 95, 96, 97, 98, 99 or 100% sequence identity with SEQ ID NO:1 and an additional duplicate identical or heterologous first, second and/or third nucleotide sequence. Also preferred is a nucleic acid molecule as defined herein comprising a nucleotide sequence that has 80, 81, 82, 83, 84, 85, 86, 87, 88, 89, 90, 91, 92, 93, 94, 95, 96, 97, 98, 99 or 100% sequence identity with SEQ ID NO: 6 and 20.

In another preferred embodiment, a nucleic acid molecule as defined herein comprises a fourth nucleotide sequence encoding a CHAP (cysteine, histidine-dependent amidohydrolases/peptidases) domain. More preferably, said fourth nucleotide sequences originates from S. aureus bacteriophage Φ11 or S. aureus bacteriophage Φ☐Twort endolysin. Even more preferably, said fourth nucleotide sequence has 80, 81, 82, 83, 84, 85, 86, 87, 88, 89, 90, 91, 92, 93, 94, 95, 96, 97, 98, 99 or 100% sequence identity with SEQ ID NO: 18 or SEQ ID NO: 19. Preferably, a nucleic acid molecule as defined herein comprises a nucleotide sequence that has 80, 81, 82, 83, 84, 85, 86, 87, 88, 89, 90, 91, 92, 93, 94, 95, 96, 97, 98, 99 or 100% sequence identity with SEQ ID NO: 5 or 7. We showed here that a molecule comprising said first, second, third and fourth nucleotide sequences as defined by SEQ ID NO: 5 encodes for a polypeptide exhibiting an increased lytic activity and/or a shifted, preferably decreased pH optimum as compared to a polypeptide encoded by a construct lacking said fourth domain and/or compared to S. aureus bacteriophage Φ2638a endolysin encoded by SEQ ID NO:1. Lytic activity was assessed spectrophotometrically and under the conditions as earlier defined herein. Preferably, said polypeptide exhibits an increase in a lytic activity of at least 0.7, 0.8, 0.9, 1.0, 1.1, 1.2, 1.3, 1.4, 1.5, 1.6, 1.7, 1.8, 1.9, or 2 fold as compared to a lytic activity of a polypeptide encoded by a reference polypeptide differing from said polypeptide only in lacking said fourth domain or as compared to a lytic activity of S. aureus bacteriophage Φ2638a endolysin encoded by SEQ ID NO:1. Even more preferably, said polypeptide exhibits an increase in a lytic activity of at least 2.5 fold as compared to the defined reference polypeptide or a polypeptide encoded by SEQ ID NO:1.

A shifted or decreased pH optimum is defined herein as a shift or decrease in optimal lytic activity to a lower pH value, where ionic strength is kept constant. Lytic activity is preferably assessed spectrophotometrically as defined herein. Preferably, the pH optimum of a lytic activity is decreased 0.5-1 pH unit as compared to a lytic activity of a polypeptide encoded by a reference polypeptide differing from said polypeptide only in lacking said fourth domain or as compared to a lytic activity of S. aureus bacteriophage Φ2638a endolysin encoded by SEQ ID NO:1.

The invention preferably relates to a nucleic acid molecule comprising a first, second, third and optionally fourth nucleotide sequences as identified herein encoding a polypeptide which has the same lytic activity and/or the same pH optimum or which has an increased lytic activity and/or a decreased pH optimum as compared to a lytic activity of S. aureus bacteriophage Φ2638a endolysin encoded by SEQ ID NO:1. The same being identified herein as no detectable difference when using the assay as identified herein or a method well known by the artisan. The current invention also relates to a nucleic acid molecule comprising a first, second, and fourth nucleotide sequence as identified herein encoding a polypeptide which has the same lytic activity and/or the same pH optimum or which has an increased lytic activity and/or a decreased pH optimum as compared to a lytic activity of S. aureus bacteriophage Φ2638a endolysin encoded by SEQ ID NO:1. The current invention also relates to a nucleic acid molecule comprising a first, third, and fourth nucleotide sequence as identified herein encoding a polypeptide which has the same lytic activity and/or the same pH optimum or which has an increased lytic activity and/or a decreased pH optimum as compared to a lytic activity of S. aureus bacteriophage Φ2638a endolysin encoded by SEQ ID NO:1. Each of the nucleotide sequences identified herein, i.e. first, second, third, fourth nucleotide sequences, encoding the individual domain of a polypeptide defined herein can be assembled by any usual method known for constructing and assembling nucleic acid fragments which are well known to those skilled in the art and widely described in the literature (Sambrook, Maniatis et al. (1989) and illustrated experimental part of the disclosure. In a preferred embodiment, a first, second, third and/or fourth nucleotide sequences are operably linked together.

Accordingly, a nucleic acid molecule of the invention encodes a polypeptide, preferably a polypeptide as identified herein which is able to bind Staphylococcus genera via the cell wall-binding domain encoded by a first nucleotide sequence as defined herein and/or lyse said bacteria via an endopeptidase and/or amidase domain and optionally a CHAP domain encoded by a second, third and fourth nucleotide sequence, respectively, as defined herein.

In a preferred embodiment, a nucleic acid molecule of the invention as defined herein optionally comprises a sequence encoding a tag for ease of purification. Preferably, said tag is selected from, but is not limited to, the group consisting of a FLAG-tag, poly(His)-tag, HA-tag and Myc-tag. More preferably said tag is a 6×His-tag. Even more preferably, said tag is an N-terminal 6×His-tag identical to SEQ ID NO: 43.

Polypeptide

In a further aspect, there is provided a polypeptide encoded by a nucleic acid molecule as earlier identified herein. This polypeptide comprises a cell wall-binding domain and preferably an endopeptidase domain and/or an amidase domain as defined in the previous section.

A polypeptide domain encompassed by the current invention preferably has 80, 81, 82, 83, 84, 85, 86, 87, 88, 89, 90, 91, 92, 93, 94, 95, 96, 97, 98, 99 or 100% sequence identity with SEQ ID NO: 35, 36, 37, 38, 39, 40, 41 and/or 42. Preferably, a polypeptide domain encompassed by the current invention preferably comprises one ore more putative linkers and has 80, 81, 82, 83, 84, 85, 86, 87, 88, 89, 90, 91, 92, 93, 94, 95, 96, 97, 98, 99 or 100% sequence identity with SEQ ID NO: 51, 52, 53, 54, 55, 56, 57 and/or 58.

A polypeptide encompassed by the current invention preferably has 80, 81, 82, 83, 84, 85, 86, 87, 88, 89, 90, 91, 92, 93, 94, 95, 96, 97, 98, 99 or 100% sequence identity with SEQ ID NO: 21, 25, 26, 27, 29 and/or 32. More preferably, a polypeptide encompassed by the current invention preferably has 80, 81, 82, 83, 84, 85, 86, 87, 88, 89, 90, 91, 92, 93, 94, 95, 96, 97, 98, 99 or 100% sequence identity with SEQ ID NO: 25, 26, 27, 29 and/or 32 with SEQ ID NO: 25, 26, 27, 29 and/or 32.

In an embodiment of the current invention, a polypeptide preferably has at least 80% sequence identity with SEQ ID NO: 21, 25, 26, 27, 29, 32, 35, 36, 37, 38, 39, 40, 41, and/or 42 encoded by a nucleic acid construct with at least 80% identity with SEQ ID NO: 1, 5, 6, 7, 9, 20, 12, 13, 14, 15, 16, 17, 18 and/or 19, respectively. More preferably, a polypeptide of the current invention has at least 80% sequence identity with SEQ ID NO: 25, 26, 27, 29, 32, 35, 36, 37, 38, 39, 40, 41, and/or 42 encoded by a nucleic acid construct with at least 80% identity with SEQ ID NO: 5, 6, 7, 9, 20, 12, 13, 14, 15, 16, 17, 18 and/or 19, respectively.

A polypeptide according to the invention may have a length of at least 94, 95, 96, 100, 110 or 120 amino acids, preferably 127 amino acids and/or at most 1500, 1400, 1300 or 1200 amino acids. Preferably, said polypeptide has a length of at least 400, 410, 420, 430, 440, 450, 460, 470, 480, 490, 500, 510 or 520 amino acids and/or at most 1500, 1400, 1300 or 1200 amino acids. Also preferred is a polypeptide according to the invention with a length of at least 630, 640, 650, 660, 670, 680, 690, 700, 710 or 720 amino acids and/or at most 1500, 1400, 1300 or 1200 amino acids.

An amino acid or nucleotide sequence, encompassed by the present invention, may be derived from one of the sequences as identified herein by substituting, inserting, deleting, or adding one, 2, 3, 4, 5, 6, 7, 8, 9, 10, 12, 14, 16, 18, 20 or more nucleotides or amino acids, respectively. An amino acid sequence, encompassed by the present invention, may be derived from one of the sequences as identified herein by adding an additional N- or C-terminal amino acids or chemical moieties to increase stability, solubility and activity An embodiment of the invention encompasses a variant polypeptide. A variant polypeptide may be a non-naturally occurring form of the polypeptide. A polypeptide variant may differ in some engineered way from the polypeptide isolated from its native source. A variant may be made by site-directed mutagenesis starting from the nucleotide sequence of SEQ ID NO: 1, 5, 6, 7, 9, 12, 13, 14, 15, 16, 17, 18, 19 and/or 20. Preferably, a polypeptide variant contains mutations that do not alter the biological function of the encoded polypeptide. According to a preferred embodiment, a polypeptide variant exhibits *Staphylococcus* peptidoglycan cell wall-binding and/or a lytic activity which is the same or enhanced as compared to the *Staphylococcus* peptidoglycan cell-wall binding and/or lytic activity of *S. aureus* bacteriophage Φ2638a endolysin encoded by SEQ ID NO:1. A polypeptide variant of the invention preferably is a variant of SEQ ID NO: 21, 25, 26, 27, 29, 32, 35, 36, 37, 38, 39, 40, 41 and/or 42. A polypeptide variant with the same or an enhanced *Staphylococcus* peptidoglycan cell-wall binding and/or lytic activity is a polypeptide exhibiting a *Staphylococcus aureus* peptidoglycan cell-wall binding and/or lytic activity, which is the same or increased compared to the *Staphylococcus* peptidoglycan cell-wall binding and/or lytic activity of *S. aureus* bacteriophage Φ2638a endolysin encoded by SEQ ID NO:1 measured in an assay as earlier identified herein.

According to another preferred embodiment, a nucleotide sequence of the invention is a variant of the nucleotide sequences of SEQ ID NO: 1, 5, 6, 7, 9, 12, 13, 14, 15, 16, 17, 18, 19 and/or 20. Nucleotide sequence variants may be used for preparing a polypeptide variant as defined earlier. A nucleic acid variant may be a fragment of any of the nucleotide sequences as defined above. A nucleic acid variant may also be a nucleotide sequence that differs from SEQ ID NO: 1, 5, 6, 7, 9, 12, 13, 14, 15, 16, 17, 18, 19 and/or 20 by virtue of the degeneracy of the genetic code. A nucleic acid variant may also be an allelic variant of SEQ ID NO: 1, 5, 6, 7, 9, 12,13, 14, 15, 16, 17, 18, 19 and/or 20. An allelic variant denotes any of two or more alternative forms of a gene occupying the same chromosome locus. A preferred nucleic acid variant is a nucleotide sequence, which contains silent mutation(s). Alternatively or in combination, a nucleic acid variant may also be obtained by introduction of nucleotide substitutions, which do not give rise to another amino acid sequence of the polypeptide encoded by the nucleotide sequence, but which corresponds to the codon usage of the host organism intended for production of the polypeptide of the invention. According to a preferred embodiment, a nucleic acid variant encodes a polypeptide still exhibiting its biological function. More preferably, a nucleotide sequence variant encodes a polypeptide exhibiting *Staphylococcus* peptidoglycan cell wall-binding and/or a lytic activity. Even more preferably, a nucleic acid variant encodes a polypeptide with enhanced *Stahpylococcus* peptidoglycan cell wall-binding and/or lytic activity as defined earlier. Nucleic acids encoding a polypeptide exhibiting S *Stahpylococcus* peptidoglycan cell wall-binding and/or lytic activity may be isolated from any microorganism.

All these variants can be obtained using techniques known to the skilled person, such as screening of library by hybridisation (southern blotting procedures) under low to medium to high hybridisation conditions with for the nucleotide sequence SEQ ID NO: 1, 5, 6, 7, 9, 12, 13, 14, 15, 16, 17, 18, 19 and/or 20 or a variant thereof which can be used to design a probe. Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

The sequence information as provided herein should not be so narrowly construed as to require inclusion of erroneously identified bases. The skilled person is capable of identifying such erroneously identified bases and knows how to correct for such errors.

Nucleic Acid Construct

In a further aspect, there is provided a nucleic acid construct comprising a nucleic acid molecule as identified in the previous section. This nucleic acid construct may comprise a first nucleic acid sequence encoding a polypeptide comprising a cell wall-binding domain, possibly further comprising a second and third and optionally fourth nucleic acid sequence as defined in the previous section.

The invention also relates to an expression vector comprising a nucleic acid construct of the invention. Preferably, an expression vector comprises a nucleotide sequence of the invention, which is operably linked to one or more control sequences, which direct the production or expression of the encoded polypeptide in a cell, a subject, or a cell-free expression system.

An expression vector may be seen as a recombinant expression vector. This vector can be constituted by a plasmid, a cosmid, a bacteriophage or a virus which is transformed by introducing a nucleic acid molecule according to the invention. Such transformation vectors according to the host organism to be transformed are well known to those skilled in the art and widely described in the literature.

A further subject of the invention is a process for the transformation of host organisms, by integrating a least one nucleic acid molecule of the invention, which transformation may be carried out by any suitable known means which have been widely described in the specialist literature and in particular in the references cited in the present application, more particularly by the vector according to the invention.

Cell

In a further aspect, the present invention relates to a cell, which comprises a nucleic acid construct or an expression vector of the invention as defined herein. A cell may be any microbial, prokaryotic or eukaryotic cell, which is suitable for expression of the polypeptide of the invention. In a preferred embodiment, said cell is an *E. Coli*. In an even more preferred embodiment, said cell is *E. coli* CL1blue MRF.

Method

In a further aspect, there is provided a method for producing, optionally purifying and optionally freeze-drying a polypeptide as defined in the previous section. Said method comprising the steps of:
  i) producing said polypeptide in a cell comprising a nucleic acid construct as defined in the previous section, optionally
  ii) purifying said polypeptide, and optionally
  iii) freeze-drying said purified polypeptide.

In a preferred embodiment, an *E. Coli* is used in step i) for producing a polypeptide using recombinant technologies. More preferably an *E. coli* XL1blueMRF is used in step i) for producing a polypeptide using recombinant technologies Preferably, in step ii), IMAC and Econo-Pac Chromatography columns (Biorad) packed with 5 mL low density Nickel chelating agarose beads (ABT beads) in combination with gravity flow is used to purify said (6×His-tagged recombinant) polypeptides. The eluted polypeptide can be dialyzed for 2, 4, and 12 hours against 3×11 lyophilization buffer, said buffer preferably comprising 50 mM phosphate, 500 mM sucrose, 200 mM mannitol, 0.005% polysorbate20, pH 7.4.

Method

In a further aspect, the invention also relates to a method for producing a polypeptide with an enhanced lytic activity by treating a polypeptide as defined in the previous section or as obtainable by the method described above. Said treatment comprises substituting a divalent metal ion for increasing a lytic activity as compared to an untreated polypeptide, preferably said method comprising the steps of:
  i) dialyzing said polypeptide against a buffer comprising a chelating compound;
  ii) dialyzing said polypeptide against a divalent metal ion-containing buffer, preferably said divalent metal ion being selected from the group consisting of $Mn^{2+}$, $Co^{2+}$, $Cu^{2+}$, and $Zn^{2+}$.

A "chelating compound" being defined herein as a compound that binds a metal ion. Well known chelating compounds are ethylene diamine tetraacetic acid (EDTA) and ethylene glycol tetraacetic acid (EGTA). Preferably EDTA is used in step i) of the method of the invention.

Preferably, the divalent metal ion of step ii) is selected from the group consisting $Mn^{2+}$, $Co^{2+}$, $Cu^{2+}$, more preferably, said divalent metal ion is selected from the group consisting of $Mn^{2+}$ and $Co^{2+}$, even more preferably said divalent metal ion is $Mn^{2+}$.

We showed that substituting a divalent metal ion by any of the above defined resulted in an increase of a lytic activity of Ply2638 of 2-2.5 fold. Lytic activity was assessed spectrophotometrically as defined herein. Preferably, said method leads to an increase in a lytic activity of at least 1.1, 1.2, 1.3, 1.4, 1.5, 1.6, 1.7, 1.8, 1.9 or 2 fold as compared to an untreated polypeptide. Even more preferably, the method leads to an increase in a lytic activity of at least 2.5 fold. Preferably, the treated polypeptide exhibits a 0.7, 0.8, 0.9, 1.0, 1.1, 1.2, 1.3, 1.4, 1.5, 1.6, 1.7, 1.8, 1.9 to 2 fold increase in lytic activity as compared to the untreated polypeptide encoded by SEQ ID NO: 1.

Composition

In a further aspect, there is provided a composition comprising a nucleic acid molecule or a nucleic acid construct or a polypeptide or a vector or a cell as identified herein or obtainable by a method described herein. Preferably, the invention relates to a composition exhibiting a lytic activity as defined herein. More preferably, said composition is for use as a medicament. This medicament is preferably for treating, preventing and/or delaying an infectious disease. The invention also relates to a pharmaceutical or medical composition. Even more preferably, the invention relates to a pharmaceutical or medical composition for the treatment of an infectious disease. Preferably, the invention relates to a pharmaceutical or medical composition for the treatment of an infectious disease caused by a bacterium, preferably a bacterium of the genus *Staphylococcus*, more preferably a bacterium of the species *S. aureus*. Preferably, said infectious disease is a skin infection, mastitis, pneumonia, meningitis, endocarditis, Toxic Shock Syndrome (TSS), sepsis, septicemia, bacteremia, or osteomyelitis. Preferably, said skin infection is selected from the group of pimples, impetigo, boils, furuncles, cellulitis folliculitis, carbuncles, scaled skin syndrome and abscesses.

A composition as defined herein may comprise a mixture of different nucleic acid molecules, and/or nucleic acid constructs and/or polypeptides an/or vectors and/or cells as identified herein or obtainable by a method described herein.

A composition as defined herein may comprise one or more additional active ingredients. Active preferably being defined herein as showing a lytic activity as defined herein. Preferably, said one or more additional active ingredients are selected from the group consisting of a bacteriophage or phage and antibiotic. A phage encompassed herein can be any phage known in literature. Preferably, a phage encompassed by the present invention belongs, but is not limited, to a family of the list consisting of Myoviridae, Siphoviridae and Podoviridae. A phage encompassed by the present invention may also belong to a family of the list consisting of Tectiviridae, Corticoviridae, Lipothrixviridae, Plasmaviridae, Rudiviridae, Fuselloviridae, Inoviridae, Microviridae, Leviviridae and Cystoviridae. More preferably, said one or more active ingredients comprise and/or consist of lysostaphin, preferably *S. Simulans* lysostaphin having 80, 81, 82, 83, 84, 85, 86, 87, 88, 89, 90, 91, 92, 93, 94, 95, 96, 97, 98, 99 or 100% sequence identity with SEQ ID NO: 34, more preferably *S. Simulans* lysostaphin of SEQ ID NO: 34.). Even more preferably, said one or more active ingredients comprise and/or consist of both one or more different bacteriophages and lysostaphin, preferably, one or more different phages and *S. Simulans* lysostaphin (SEQ ID NO: 34). Within the context of this invention, a combination of active ingredients as defined herein can be administered sequentially and/or simultaneously.

A composition as defined herein may further comprise a pharmaceutically acceptable carrier. Such composition is preferably for use as a medicine or as a medicament. Preferably the medicament is used in the treatment of infectious diseases. A composition may be in the liquid, solid or semi-liquid or semi-solid form.

A composition of the invention can be used to treat animals, including humans, infected with *S. aureus*. Any suitable route of administration can be used to administer said composition including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges.

A composition comprising a nucleic acid molecule or a nucleic acid construct or a polypeptide or a vector or a cell as identified herein or obtainable by a method described herein is preferably said to be active, functional or therapeutically active or able to treat, prevent and/or delay an infectious disease when it decreases the amount of a *Staphylococcus* genera present in a patient or in a cell of said patient or in a cell line or in a cell free in vitro system and preferably means that 99%, 90%, 80%, 70%, 60%, 50%, 40%, 30%, 20%, 10%, 5% or less of the initial amount of a *Staphylococcus* genera, is still detectable. Preferably no *Staphylococcus* genera is detectable. In this paragraph, the expression "amount of *Staphylococcus* genera" preferably means alive *Staphylococcus* genera. *Staphylococcus* genera may be detected using standard techniques known by the artisan such as immunohistochemical techniques using *Staphylococcus* specific antibodies, tube coagulase tests that detect staphylocoagulase or "free coagulase", detection of surface proteins such as clumping factor (slide coagulase test) and/or protein A (commercial latex tests). Alive *Staphylococcus* genera may be detected using standard techniques known by the artisan such as microbiological bacterial culture techniques and/or real-time quantitative reverse transcription polymerase chain reaction to assay for bacterial mRNA.

Said decrease is preferably assessed in a tissue or in a cell of an individual or a patient by comparison to the amount present in said individual or patient before treatment with said composition or polypeptide of the invention. Alternatively, the comparison can be made with a tissue or cell of said individual or patient which has not yet been treated with said composition or polypeptide in case the treatment is local.

A composition comprising a nucleic acid molecule or a nucleic acid construct or a polypeptide or a vector or a cell as identified herein or obtainable by a method described herein may be administered to a patient or of a cell, tissue or organ or said patient at least one week, one month, six month, one year or more.

In another embodiment, the invention relates to a non-medical composition exhibiting a binding and/or lytic activity as defined herein. Preferably the invention relates to an antimicrobial. Preferably, the invention relates to an antimicrobial for lysing a bacterium, preferably a bacterium of the genus *Staphylococcus*, more preferably a bacterium of the species *S. aureus*. Preferably the invention relates to an antimicrobial as food preservative or disinfectant.

Use

In a further aspect, the invention relates to the use of a polypeptide comprising domains encoded by a first, second, third and optionally fourth nucleic acid sequence as defined herein, a nucleic acid molecule encoding such polypeptide, a construct comprising such nucleic acid molecule, a vector comprising such construct, a cell comprising such vector and/or a composition comprising any of the above, preferably as antimicrobial. Preferably, the invention relates the use as an antimicrobial for lysing a bacterium, preferably a bacterium of the genus *Staphylococcus*, more preferably a bacterium of the species *S. aureus*. Preferably the invention relates to an antimicrobial as food preservative or disinfectant. Possibly, such food preservatives or disinfectants are used together with other antimicrobial agents. Preferably, such food preservatives or disinfectants are used in combination with one or more additional active ingredients as defined herein. Preferably, said one or more additional active ingredients are selected from the group consisting of a bacteriophage or phage and antibiotic as defined herein.

The above-referenced polypeptide, nucleic acid molecule, construct, vector, cell and/or composition can be applied on or into food products, and/or into various physical sites to be disinfected, by a number of means including, but not limited to, admixing said polypeptide and/or cell containing polypeptide of the invention into the food products, spraying said polypeptide and/or cell containing the polypeptide of the invention onto the foodstuffs or physical sites to be disinfected.

A polypeptide of the invention can be isolated from a cell or a cell containing said polypeptide of the invention can be directly applied or administered without isolation of said polypeptide. For example, a cell which produces a polypeptide of the invention could be administered to a subject (human or animal) or applied to a surface where the polypeptide of the invention would be secreted into food, onto a surface or into the subject's gut. The polypeptide of the invention can then bind and optionally lyse bacterial cells, preferably a bacterium of the genus *Staphylococcus*, more preferably a bacterium of the species *S. aureus*, present in this environment.

Further encompassed is the use of a polypeptide comprising a domain encoded by a first nucleic acid sequence as defined herein, a nucleic acid molecule encoding such polypeptide, a construct comprising such nucleic acid molecule, a vector comprising such construct, a cell comprising such vector and/or a composition comprising any of the above, preferably for detecting bacteria, more preferably for detecting bacteria of the genus *Staphylococcus*, more preferably a bacterium of the species *S. aureus*. Preferably, said polypeptide, nucleic acid molecule, construct, vector, cell and/or composition is used in a diagnostic application. Possibly said polypeptide, nucleic acid molecule, a construct, a vector, cell and/or a composition is used together with other detection agents.

Method

The invention further relates in a further aspect to a method for treating, delaying and/or preventing an infectious disease by administering a composition as earlier defined herein. All features of this method have already been defined herein.

Definitions

Sequence Identity

"Sequence identity" is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. "Similarity" between two amino acid sequences is determined by comparing the amino acid sequence and its conserved amino acid substitutes of one peptide or polypeptide to the sequence of a second peptide or polypeptide. In a preferred embodiment, identity or similarity is calculated over the whole SEQ ID NO as identified herein. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Nucleic Acid Construct, Transformation, Expression Vector, Operably Linked, Expression, Control Sequences, Polypeptide Construct A nucleic acid molecule is represented by a nucleotide sequence. A polypeptide is represented by an amino acid sequence. A nucleic acid construct is defined as a nucleic acid molecule which is isolated from a naturally occurring gene or which has been modified to contain segments of nucleic acids which are combined or juxtaposed in a manner which would not otherwise exist in nature. A nucleic acid molecule is represented by a nucleotide sequence. Optionally, a nucleotide sequence present in a nucleic acid construct is operably linked to one or more control sequences, which direct the production or expression of said peptide or polypeptide in a cell or in a subject.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject.

Expression will be understood to include any step involved in the production of the peptide or polypeptide including, but not limited to, transcription, post-transcriptional modification, translation, post-translational modification and secretion.

Control sequence is defined herein to include all components which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a peptide or polypeptide as identified herein.

The term "transformation" refers to a permanent or transient genetic change induced in a cell following the incorporation of new DNA (i.e. DNA exogenous to the cell). When the cell is a bacterial cell, as is intended in the current invention, the term usually refers to an extrachromosomal, self-replicating vector which harbors a selectable antibiotic resistance.

An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene. It is related to the binding site identified by the presence of a binding site for DNA-dependent RNA polymerase, transcription initiation sites, and any other DNA sequences, including, but not limited to, transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product or a composition or a nucleic acid molecule or a peptide or polypeptide of a nucleic acid construct or vector or cell as defined herein may comprise additional component(s) than the ones specifically identified; said additional component(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Figure 1:
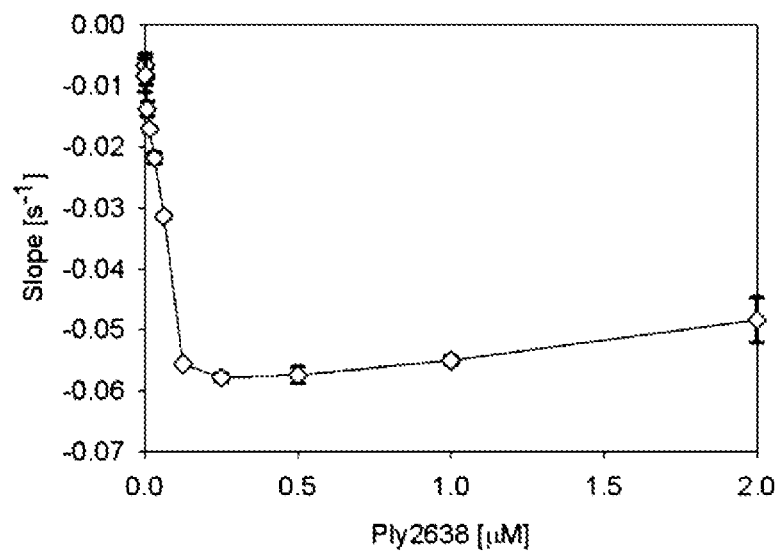
FIG. 1. Linear relationship of Ply2638 (SEQ ID NO: 21 encoded by SEQ ID NO: 44) activity against *S. aureus* SA2638/2854 cells in dependency of endolysin concentration. Assays were performed under standard conditions (PBS buffer pH 7.4, 120 mM sodium chloride) in photometric lysis assays. Maximum activity was determined from the first derivative of regression fits from sigmoidal lysis curves, calculated with SigmaPlot software. Error bars represent standard deviation calculated from technical triplicate experiments FIG. 2. Influence of divalent cations on lytic activity of Ply2638 (SEQ ID NO: 21, encoded by SEQ ID NO: 44). The enzyme was EDTA treated with subsequent substitution of metal ions by dialysis against MOPS buffer containing $MgCl_2$, $CaCl_2$, $ZnCl_2$, $CuCl_2$, $CoCl_2$, or $MnSO_4$. Ply2638 dialyzed against MOPS buffer omitting EDTA treatment served as reference. Error bars represent standard deviation, calculated from technical triplicate experiments.
Figure 2:
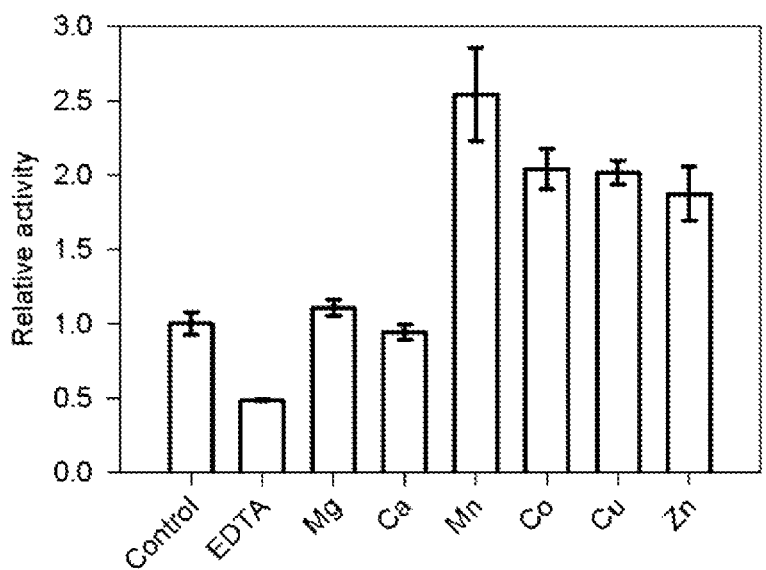
Figure 3:
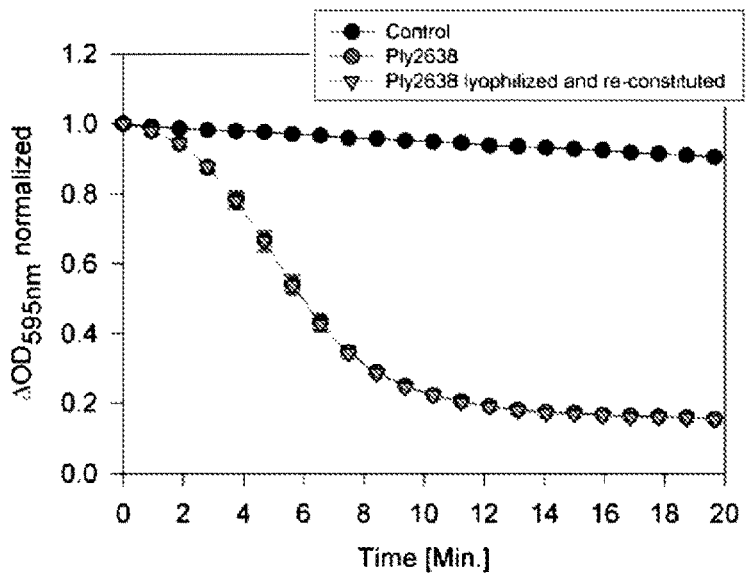
FIG. 3. Lytic activity of 50 nM Ply2638 (SEQ ID NO: 21, encoded by SEQ ID NO: 44) on *S. aureus* SA2638/2854 cells after lyophilization and reconstitution. Activity was measured in a turbidity reduction assay under standard conditions. Lyophilization buffer was taken as a control. The triple domain enzyme recovers full lytic activity after freeze-drying.
Figure 4:
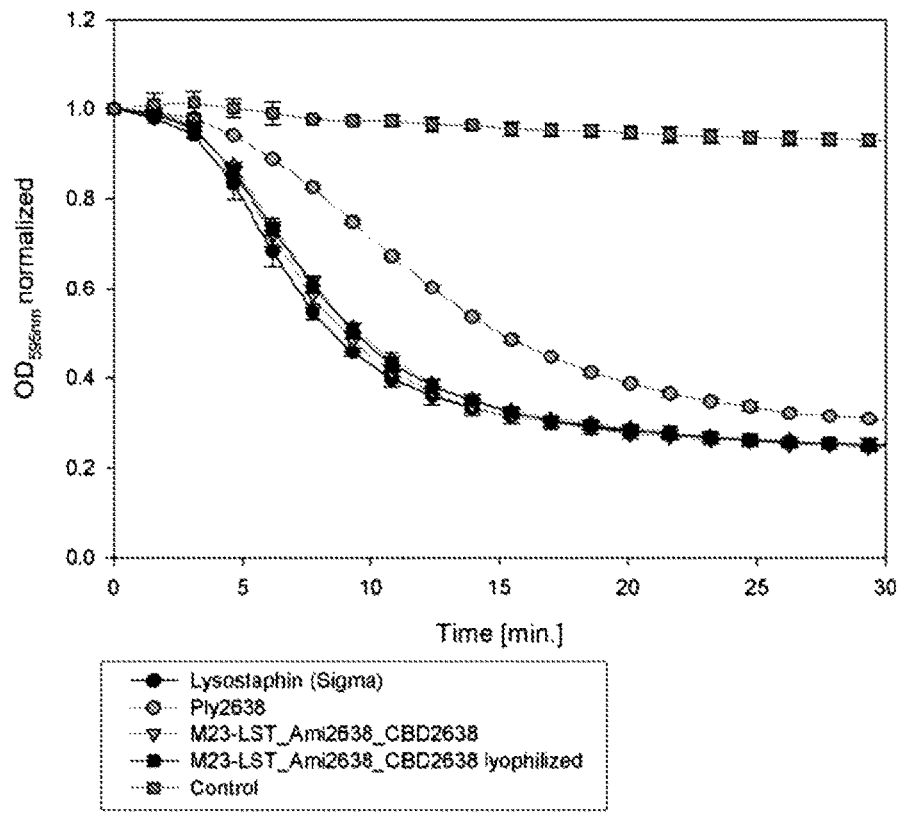
FIG. 4. Lytic activity of 50 nM M23-LST_Ami2638_CBD2638 (SEQ ID NO: 29, encoded by SEQ ID NO: 48) on *S. aureus* SA2638/2854 cells after lyophilization and reconstitution (indicated as lyophilized) as compared to freshly prepared M23-LST_Ami2638_CBD2638 (SEQ ID NO: 29, encoded by SEQ ID NO: 48) and Ply2638 (SEQ ID NO: 21, encoded by SEQ ID NO: 44). Lyophilization buffer was taken as a control. Activity was measured in a turbidity reduction assay under standard conditions. The triple domain enzyme recovers full lytic activity after freeze-drying.
Figure 5:
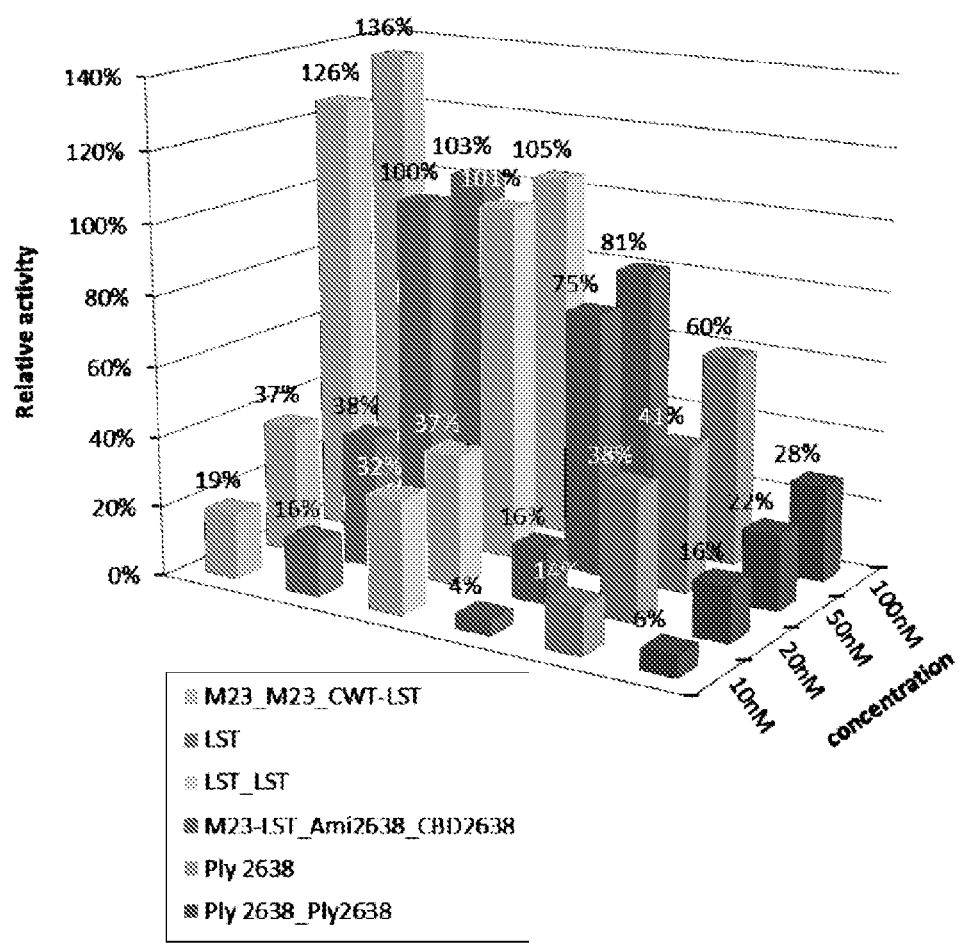
FIG. 5. Relative activity of Lysostaphin (LST; SEQ ID NO: 34, encoded by SEQ ID NO: 33) and Ply2638 derivatives (SEQ ID NO: 31, 30, 29, 21 and 24, encoded by SEQ ID NO: 11, 10, 48, 44 and 4, respectively) in dependency of the concentration. The activity of LST at 50 nM was set as reference. All assays were done under standard conditions (37° C., pH 7.4 and 120 mM sodium chloride concentration) using *S. aureus* SA2638/2854 substrate cells from frozen stock.
Figure 6A:
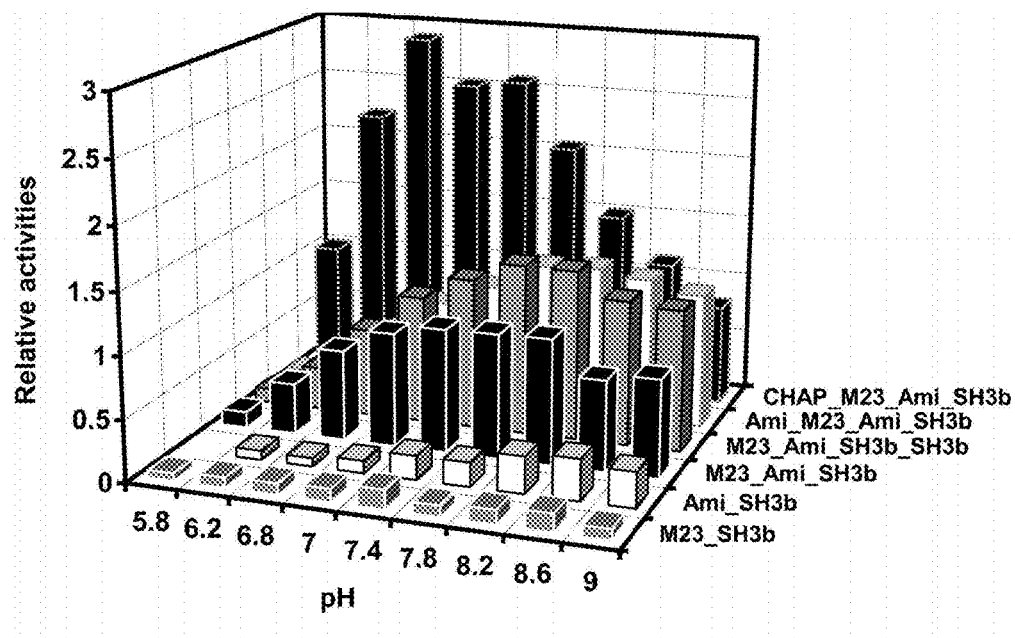
FIG. 6A. Relative activities at various pH values of truncated and (with PlyTw domains) retrofitted Ply2638 variants determined in turbidity reduction assays. Truncation of the enzyme by one of the two catalytic domains resulted in impaired activities. Duplication of the CBD (M23_Ami_SH3b_SH3b; SEQ ID NO: 32, encoded by SEQ ID NO; 49) accelerates lysis at basic pH values and elevated salt concentrations. Retrofitting of Ply2638 with CHAP11 domain results in an enzyme which is presumed to attack three different bonds in the peptidoglycan layer of *Staphylococcus*. It shifted pH optima to slight acidic conditions and improved antibacterial activity. However, protein stability of the chimeric enzymes remains a challenge. Maximum lysis velocity of Ply2638 at standard conditions (pH 7.4 and 120 mM sodium chloride concentration) was set as reference. Bars represent mean of triplicate assays, standard deviation is not shown. (CHAP_M23_Ami_SH3b=SEQ ID NO: 25, encoded by SEQ ID NO: 45; Ami_M23_Ami_SH3b=SEQ ID NO: 26, encoded by SEQ ID NO: 46; M23_Ami_SH3b_SH3b=SEQ ID NO: 32, encoded by SEQ ID NO: 49; M23_Ami_SH3b=SEQ ID NO: 21, encoded by SEQ ID NO: 44; Ami_SH3b=SEQ ID NO: 22, encoded by SEQ ID NO: 2; M23_SH3b=SEQ ID NO: 23, encoded by SEQ ID NO: 3).
Figure 6B:
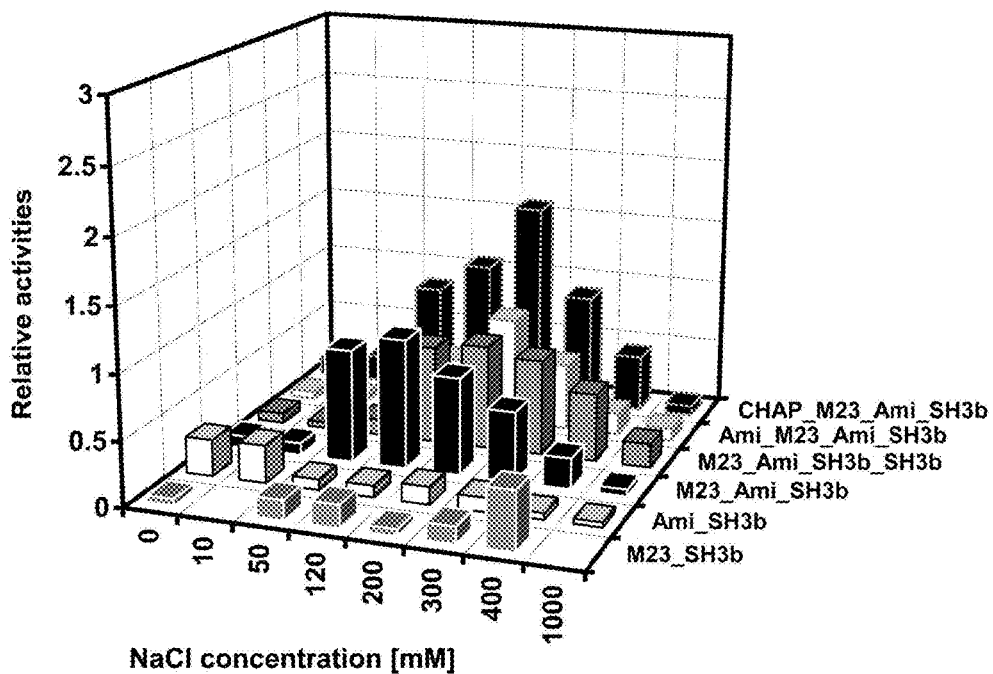
FIG. 6B. Relative activities at various sodium chloride concentrations of truncated and (with PlyTw domains) retrofitted Ply2638 variants determined in turbidity reduction assays. Truncation of the enzyme by one of the two catalytic domains resulted in impaired activities. Duplication of the CBD (M23_Ami_SH3b_SH3b; SEQ ID NO: 32, encoded by SEQ ID NO; 49) accelerates lysis at basic pH values and elevated salt concentrations. Retrofitting of Ply2638 with CHAP11 domain results in an enzyme which is presumed to attack three different bonds in the peptidoglycan layer of Staphylococcus. It shifted pH optima to slight acidic conditions and improved antibacterial activity. However, protein stability of the chimeric enzymes remains a challenge. Maximum lysis velocity of Ply2638 at standard conditions (pH 7.4 and 120 mM sodium chloride concentration) was set as reference. Bars represent mean of triplicate assays, standard deviation is not shown. (CHAP_M23_Ami_SH3b=SEQ ID NO: 25, encoded by SEQ ID NO: 45; Ami_M23_Ami_SH3b=SEQ ID NO: 26, encoded by SEQ ID NO: 46; M23_Ami_SH3b_SH3b=SEQ ID NO: 32, encoded by SEQ ID NO: 49; M23_Ami_SH3b=SEQ ID NO: 21, encoded by SEQ ID NO: 44; Ami_SH3b=SEQ ID NO: 22, encoded by SEQ ID NO: 2; M23_SH3b=SEQ ID NO: 23, encoded by SEQ ID NO: 3).
Figure 7:
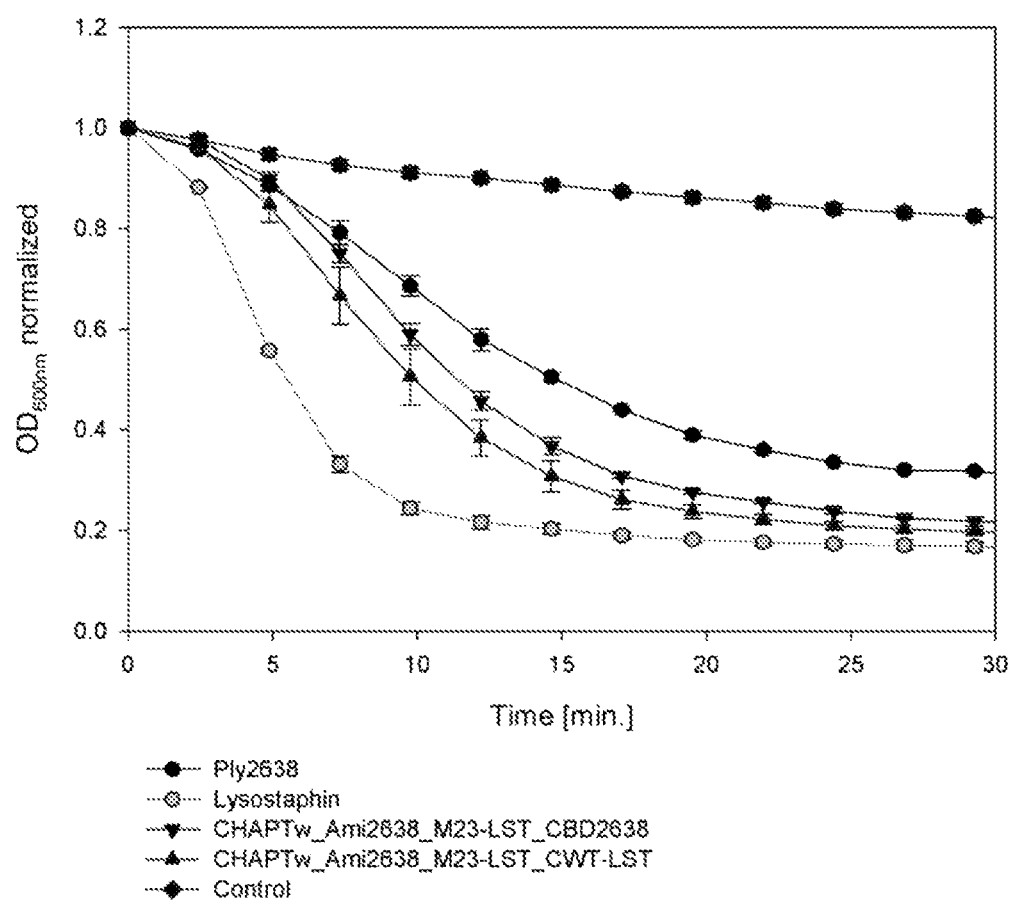
FIG. 7. Activity of 50 nM quadruple domain enzymes (SEQ ID NO: 27 and 28, encoded by SEQ ID NO: 47 and 8, respectively), Ply2638 (SEQ ID NO: 21, encoded by SEQ ID NO: 44), and Lyosotaphin (SEQ ID NO: 34, encoded by SEQ ID NO: 33) against using S. aureus SA2638/2854 substrate cells under standard conditions. Lyophilization buffer was taken as a control. Quadruple domain enzymes were constructed by combining domains of Ply2638, PlyTw, and Lysostaphin.

Materials and Methods
Bacterial Strains, Culture Conditions, Phages and Plasmids
E. coli XL1BlueMRF' and E. coli Sure was used for the over-expression of 6x-His-tagged (SEQ ID NO: 43) fusion proteins. Both strains were cultured in LB-PE medium at 30° C. with 100 µg/ml ampicillin and 30 µg/ml tetracycline for plasmid selection. Phage 2638A lysate were used as template for the amplification of Ply2638A gene or domain coding regions thereof. CHAPTw domain (SEQ ID NO: 19) was amplified from Phage Twort lysate. Cystein-Histidine dependent amidase/peptidase (CHAP) domain and amidase domain from phage 11 (SEQ ID NO 18 and 17, respectively; Donovan, et al., 2006 and 2008; Navarre et al., 1999; Sass and Bierbaum 2007) were amplified from a pet21a vector containing phi11 autolysin gene, a kindly gift from Donovan, D. M. Plasmid LT1215 containing the sequence of mature Lysostaphin (SEQ ID NO: 33) was used as template for domain amplification M23-LST (SEQ ID NO: 15) and CWT-LST (SEQ ID NO: 13).

pQE-30 vector (catalogues number: 32915, Qiagen, Hilden, Germany; SEQ ID NO: 50) was used as cloning and expression vector for the production of 6x-His tagged recombinant fusion proteins in E. coli XL1BlueMRF' or E. coli Sure respectively.

DNA Techniques and Cloning Procedures
Standard techniques according to Sambrook, Maniatis et al. (1989) were employed for cloning of single genes and the creation of fusion proteins. High Fidelity PCR Enzyme mix (Fermentas) was used in PCR reactions. DNA concentrations were determined with a spectrophotometer (NanoDrop ND-1000 Spectrophotometer).

pHP12638 is constructed by insertion of Ply2638 (SEQ ID NO: 1) encoding sequence Met1-Lys486 into pQE30 (SEQ ID NO: 50) sites BamHI-SalI. pHP12638-P12638 construct has the same sequence consecutively inserted into BamHI-SacI-SalI sites. CHAP11 (SEQ ID NO: 18), Ami11 (SEQ ID NO: 17) and CHAP_Ami11 were N-terminal introduced into BamHI digested pHPL2638A. Prior to ligation reaction, the vector was dephosphorylated using shrimp alkaline phosphatase (SAP, Fermentas). pHM23_CBD2638 (SEQ ID NO: 3), and pHM23-2638_Ami2638_CBD2638_CBD2638 (SEQ ID NO: 49) were constructed by a replacement of GFP coding region from pHGFP_CBD2638A_c vector (SEQ ID NO: 59) with the respective inserts using BamHI and SacI restriction sites. pHM23-LST_Ami2638_CBD2638 (SEQ ID NO: 48) has a pQE-30 backbone with mature lysostaphin (SEQ ID NO: 33) coding sequence Ala1-Gly154 inserted into BamHI and SacI and Ply2638 partial sequence encoding Leu138-Lys486 in SacI and SalI sites. pHM23-LST_M23-LST_CWT-LST (SEQ ID NO: 11) has mature Lysostaphin (SEQ ID NO: 33) sequences Ala1-Gly154 inserted into BamHI and SacI and Ala1-Lys246 into SacI and SalI sites of pQE30. pHLST-LST (SEQ ID NO: 10) is constructed the same way having Ala1-Lys246 repeatedly in BamHI-SacI and SacI-SalI sites. In plasmids encoding quadruple domain constructs pHCHAPTw_Ami2638_M23-LST_CBD2638 (SEQ ID NO: 47) and pHCHAPTw_Ami2638_M23-LST_CWT-LST (SEQ ID NO: 8) the domains are directly fused via splicing overlap extension PCR (SOE) and inserted into pQE30 BamHI and SalI sites. In both constructs, boarder regions of individual domains (CHAPTw, SEQ ID NO: 19: Met1-Ile140, Ami2638, SEQ ID NO: 16: Lys141-Gly358 of SEQ ID NO: 1, CBD2638, SEQ ID NO: 12: Trp393-Lys486 of SEQ ID NO: 1, M23-LST, SEQ ID NO: 15: Ala1-Gly154 of SEQ ID NO: 33, CWT-LST, SEQ ID NO: 13: Trp155-Lys246 of SEQ ID NO: 33) were determined with bioinformatics (unpublished data). Plasmids with repetitive sequences were transferred into E. coli Sure strain, all other plasmids into E. coli XL1BlueMRF'.

Expression and Purification of Recombinant Fusion Proteins
Protein overexpression and partial purification was essentially done as previously described by others (Loessner et al., 1996, Schmelcher et al., 2010). In brief, plasmid bearing E. coli were grown in 250 ml modified LB medium (15 g/l tryptose, 8 g/l yeast extract, 5 g/l NaCl, pH 7.8) to an optical density at 600 nm (OD600 nm) of 0.4 to 0.6 and induced with 1 mM IPTG. Cells were further incubated for 4 hours at 30° C., or 18 hours at 20° C., cooled to 4° C., and harvested by centrifugation. Cell pellets were suspended in 5 ml immobilization buffer (50 mM $NaH_2PO_4$, 500 mM NaCl, 5 mM imidazole, 0.1% polysorbate20, pH 7.4). Cytosolic E. coli contents containing soluble recombinant proteins were liberated by a double passage through a French Pressure Cell Press (1200 psi, SLM Aminco, Urbana, Ill., U.S.) operated at 1200 psi. Other downstream processing steps included removal of insoluble cell debris by centrifugation, filter sterilization (0.2 µm PES membrane, Millipore), and Immobilized Metal Affinity Chromatography (IMAC) purification using MicroBiospin (Bio-Rad, Hercules, Calif., U.S.) columns packet with low density Ni-NTA Superflow resin (Chemie Brunschwig AG, Basel, Switzerland). Ni-NTA immobilized proteins were on-column gravity flow washed with 5-10 column volumes immobilization buffer. Protein fractions were then eluted with elution buffer (50 mM $NaH_2PO_4$, 500 mM NaCl, 125 mM imidazole, 0.1% polysorbate20, pH 7.4) and dialyzed against two changes of dialysis buffer (50 mM NaH$_2$PO$_4$, 100 mM NaCl, 0.1% polysorbate20, pH 7.4). Protein concentrations were defined in a NanoDrop ND-1000 spectrophotmeter, corrected for specific absorbance at 280 nm as calculated from the primary amino acid sequence with Vector NTI software (Invitrogen, Carlsbad, Calif., U.S.) and estimated for purity by SDS-PAGE. Aliquots were stored at −20° C. mixed with 50% glycerol.

Lyophilization of Recombinant Proteins

IMAC purified proteins were dialyzed against 3 changes of 300 ml lyophilization buffer (50 mM phosphate or Tris, 500 mM sucrose, 200 mM mannitol, pH 7.4) aliquot and frozen in the gaseous phase of liquid nitrogen. The freeze-drying was done at −40° C. and vacuum at 75 mTorr for 60 minutes, followed by increasing temperature during 5 hours to −10° C. and another 60 minutes at −10° C. at the same vacuum levels. As final step, temperature was increased to 25° C. during 10 hours. Samples were reconstituted prior to testing in lysis assays by the addition of water.

Cell Wall-Binding Assay

As a standard assay to determine the ability of a CBD to direct a GFP fusion to the bacterial surface and mediate tight binding to the cell wall ligand, the following conditions is used: bacteria, preferably *S. aureus* BB255, from late log phase are harvested by centrifugation, resuspended in 1/10th volume of PBS-T (50 mM NaH$_2$PO$_4$, 120 mM NaCl [pH 8.0], 0.01% polysorbate 20) and stored on ice. GFP-CBD proteins, preferably SEQ ID NO: 64, encoded by SEQ ID NO: 60, are diluted in the same buffer to a concentration of 400 nM (2×GFP-CBD) and also stored on ice. In a 1.5 ml microcentrifuge cup, 100 µl cells and 100 µl of 2×GFP-CBD are mixed and incubated at room temperature for 5 min. Cells are then removed from the supernatant by centrifugation in a microfuge (16000 g, 60 s). The supernatant was discarded and cells were washed twice in 500 µl of PBS-T buffer. For fluorescence microscopy the pellet was finally resuspended in 50 µl of buffer. For fluorometer assays, the pellet is finally resuspended in 200 µl of PBS-T and transferred to a microplate well. Quantitative fluorescence assays can be performed using a multi label counter device (Victor$^3$, Perkin Elmer, Mass., U.S.) with sterile, untreated, black 96-well polystyrene microplates (Nunc, Roskilde, Denmark). As a negative control GFP can be used.

Quantitative Fluorescence Assays

Dependency of pH and salt on CBD2638 to *S. aureus* BB255 cell surface ligand interaction is investigated by incubation of cells from 1 ml volume set to an OD$_{600nm}$ 1+/−0.05 (~4×10$^9$ cells) with 7.5 µg GFP-CBDS2638 fusion protein, SEQ ID NO: 64, encoded by SEQ ID NO: 60. This cell to protein ratio is close to saturation point as determined in previous experiments and enables detection of variations in binding efficiencies. Varying pH is tested using citrate buffers pH 4.5 to 6.5 and phosphate buffers pH 6 to 9. After incubation with GFP-CBD2638 protein in pH buffer, cells are washed with respective pH buffer followed by standard PBS-T (pH 8) washing. Finally, cells are adjusted to an OD$_{595nm}$=0.3 to detect fluorescence from 200 µl suspensions thereof with a Victor$^3$ multi label counter. Similar experiments are performed using buffers prepared with increasing sodium chloride concentrations (10 mM NaH$_2$PO$_4$, 0-1000 mM NaCl, 0.1% polysorbate 20, pH 6).

Quantification of CBD binding capacity of *Staphylococcus* strains with altered cell surface properties is tested by recording relative fluorescence units (RFU) of washed and heat killed cells previously incubated with excessive GFP-CBD2638 protein. Fluorescence of equal volumes (200 µl) of GFP-CBD2638 labeled cells, adjusted to an OD$_{595nm}$=0.3, are measured using appropriate filter sets in a multi label counter device. Comparison and quantification of absorption levels of GFP-CBD2638 (SEQ ID NO: 64, encoded by SEQ ID NO: 60), GFP-CBD2638-CBD2638 (SEQ ID NO 65 and/or 66, encoded by SEQ ID NO: 61 and 62, respectively), and GFP-CBD2638-CBD2638-CBD2638 (SEQ ID NO: 67, encoded SEQ ID NO: 63) on *S. aureus* BB255 cells and SDS treated cells is done the same way.

Lysis Assays

Substrate cell for lytic activity assays were grown to an optical density at 600 nm (OD600) of 0.4, washed twice with PBST pH 7.4 and re-suspended in 15% glycerol containing PBS buffer pH 7.4 concentrating it at the same time 100 fold. The cells were stored at −20° C. For further use in binding or lytic activity assays the cells were thaw, washed with PBS pH 7.4 and diluted to an OD600 of 1±0.05. In standard lytic activity assays protein samples were diluted to equimolar amounts and distributed in transparent 96-well tissue culture test plates (SPL life sciences, Pocheon, Korea). Substrate cells were added to a final volume and drop in optical density at 595 nm (OD595 nm) were recorded for about 1 hour at 37° C.

Lytic activity of retrofitted and deletion constructs of Ply2638 were tested against Phage 2638A propagation strain *S. aureus* SA2638/2854 from frozen stock in lysis assays. We tested the activity at various buffer conditions. pH values from 4.6 to 9 in 0.4 increments were tested using Citrate/Phosphate buffers (25 mM Citrate, 25 mM Phosphate, 120 mM NaCl, pH 4.6-6.6) and Tris/Phosphate buffers (25 mM Tris, 25 mM Phosphate, 120 mM NaCl). The activity of Ply2638A derivatives at salt concentrations ranging from 0 to 1000 mM Sodium chloride (in 10 mM phosphate buffer pH 7.4) was tested. The Ply2638A derivatives were diluted to 10 µM final concentration with MQ prior to its application in lysis assays. Here, 4 µl of 10 µM Ply2638A derivatives were applied to 196 µl substrate cell suspensions using a multichannel pipette, resulting in an assay concentration of 200 nM protein. The substrate cell suspensions were prepared from frozen stocks, diluting it with pH or salt buffers and standardizing it spectrophotemetrically (Libra S22, Biochrom) to an initial OD600 of 1±0.05. Decrease in optical density at 595 nm (OD595) was measured using a Victor3 1420 Multilabel Counter instrument (Perkin Elmer) during 1 hour. Plates were shaken vigorously for 1 second (double orbit, 0.1 mm diameter) after every single read out. As positive control served N-terminal 6×His tagged Lysostaphin (HLST), commercially available Lysostaphin (recombinant, *E. coli* originated, Sigma).

As negative control we applied MilliQ water.

Influence of Divalent Metal Ions on the Activity of Ply2638

Partially purified Ply2638 (SEQ ID NO: 21) was dialyzed for 2 hours against EDTA containing buffer (50 mM MOPS, 100 mM sodium chloride, 0.005% polysorbate20, 10 mM EDTA) followed by dialysis against buffer containing the respective divalent metal ions (50 mM MOPS, 100 mM sodium chloride, 0.005% polysorbate20, and 10 mM CaCl2, 10 mM MgCl$_2$, 1 mM CoCl$_2$, 1 mM CuCl$_2$, 1 mM MnSO$_4$, or 1 mM ZnCl$_2$ respectively). Cells used as substrate were SDS treated and EDTA washed prior to its application in standard lysis assays.

Tabel 1

| | SEQ ID NO identification | | | |
|---|---|---|---|---|
| enzyme/domain/construct/vector | nucleic acid sequence | amino acid sequence | amino acid sequence of domain with putative linker | nucleic acid sequence of His-tagged construct |
| Mature enzyme | | | | |
| Ply2638 | SEQ ID NO: 1 | SEQ ID NO: 21 | | SEQ ID NO: 44 |
| LST | SEQ ID NO: 33 | SEQ ID NO: 34 | | |
| Domain | | | | |
| CBD-2638 | SEQ ID NO: 12 | SEQ ID NO: 35 | SEQ ID NO: 51 | |
| CWT-LST | SEQ ID NO: 13 | SEQ ID NO: 36 | SEQ ID NO: 52 | |
| M23-2638 | SEQ ID NO: 14 | SEQ ID NO: 37 | SEQ ID NO: 53 | |
| M23-LST | SEQ ID NO: 15 | SEQ ID NO: 38 | SEQ ID NO: 54 | |
| Ami-2638 | SEQ ID NO: 16 | SEQ ID NO: 39 | SEQ ID NO: 55 | |
| Ami-φ11 | SEQ ID NO: 17 | SEQ ID NO: 40 | SEQ ID NO: 56 | |
| CHAP-φ11 | SEQ ID NO: 18 | SEQ ID NO: 41 | SEQ ID NO: 57 | |
| CHAP-φTwort | SEQ ID NO: 19 | SEQ ID NO: 42 | SEQ ID NO: 58 | |
| Retrofitted construct | | | | |
| CHAP11_M23-2638_Ami2638_CBD2638 | SEQ ID NO: 5 | SEQ ID NO: 25 | | SEQ ID NO: 45 |
| Ami11_M23-2638_Ami2638_CBD2638 | SEQ ID NO: 6 | SEQ ID NO: 26 | | SEQ ID NO: 46 |
| CHAPTw_Ami2638_M23-LST_CBD2638 | SEQ ID NO: 7 | SEQ ID NO: 27 | | SEQ ID NO: 47 |
| M23-LST_Ami2638_CBD2638 | SEQ ID NO: 9 | SEQ ID NO: 29 | | SEQ ID NO: 48 |
| M23-2638_Ami2638_CBD2638_CBD2638 | SEQ ID NO: 20 | SEQ ID NO: 32 | | SEQ ID NO: 49 |
| Ami2638_CBD2638 | | SEQ ID NO: 22 | | SEQ ID NO: 2 |
| M23-2638_CBD2638 | | SEQ ID NO: 23 | | SEQ ID NO: 3 |
| Ply2638-Ply2638 | | SEQ ID NO: 24 | | SEQ ID NO: 4 |
| CHAPTw_Ami2638_M23-LST_CWT-LST | | SEQ ID NO: 28 | | SEQ ID NO: 8 |
| LST_LST | | SEQ ID NO: 30 | | SEQ ID NO: 10 |
| M23-LST_M23-LST_CWT-LST | | SEQ ID NO: 31 | | SEQ ID NO: 11 |
| GFP_CBD2638 | | SEQ ID NO: 64 | | SEQ ID NO: 60 |
| GFP_CBD2638_ CBD2638 var.1 | | SEQ ID NO: 65 | | SEQ ID NO: 61 |
| GFP_CBD2638_ CBD2638 var. 2 | | SEQ ID NO: 66 | | SEQ ID NO: 62 |
| GFP_CBD2638_ CBD2638_ CBD2638 | | SEQ ID NO: 67 | | SEQ ID NO: 63 |
| Tag | | | | |
| 6xHis-tag | | SEQ ID NO: 43 | | |
| Vector | | | | |
| pQE-30 vector | SEQ ID NO: 50 | | | |
| pHGFP_CBD2638_c vector | SEQ ID NO: 59 | | | |

---

The invention claimed is:

1. A nucleic acid molecule comprising a first nucleotide sequence, wherein said first nucleotide sequence encodes a cell wall-binding domain binding the peptidoglycan cell wall of *Staphylococcus* genera and wherein said first nucleotide sequence has at least 90% sequence identity with SEQ ID NO: 12 and wherein said nucleic acid molecule further comprises a heterologous nucleotide sequence encoding a lytic domain, wherein said lytic domain is a second and third nucleotide sequences, and wherein said second nucleotide sequence encodes an M23 endopeptidase domain and said third nucleotide sequences encodes an amidase domain.

2. The nucleic acid molecule according to claim 1, wherein said first nucleotide sequence originates from *S. aureus* bacteriophage Φ2638a endolysin.

3. The nucleic acid molecule according to claim 1, wherein said second and third nucleotide sequences originate from a gene encoding for an enzyme selected from the group consisting of *S. aureus* bacteriophage Φ2638a endolysin, *S. aureus* bacteriophage Φ11 endolysin, *S. aureus* bacteriophage Φ Twort endolysin and *S. Simulans* lysostaphin.

4. The nucleic acid molecule according to claim 3, wherein said second nucleotide sequence has at least 80% sequence identity with SEQ ID:14 or 15 and said third nucleotide sequences has at least 80% sequence identity with SEQ ID NO: 16 or 17.

5. The nucleic acid molecule according to claim 4, wherein said nucleotide molecule has at least 80% sequence identity with SEQ ID NO: 9.

6. The nucleic acid molecule according to claim 1, further comprising a fourth nucleotide sequence encoding a CHAP (cysteine, histidine-dependent amidohydrolases/peptidases) domain.

7. The nucleic acid molecule according to claim 6, wherein said fourth nucleotide sequences originates from *S. aureus* bacteriophage Φ11 or *S. aureus* bacteriophage Φ Twort endolysin.

8. The nucleic acid molecule according to claim 7, wherein said fourth nucleotide sequences has at least 80% sequence identity with SEQ ID NO: 18 or SEQ ID NO: 19.

9. The nucleic acid molecule according to claim 1, encoding a polypeptide which has the same or an increased lytic activity and/or the same or a decreased pH optimum as compared to *S. aureus* bacteriophage Φ2638a endolysin encoded by SEQ ID NO: 1.

10. A polypeptide encoded by a nucleic acid molecule as identified in claim 1.

11. A nucleic acid construct comprising a nucleic acid molecule as identified in claim 1.

12. An expression vector comprising a nucleic acid construct as defined in claim 11 operably linked to one or more control sequences, which direct the production or expression of the encoded polypeptide in a cell, a subject, or a cell-free expression system.

13. A cell comprising the nucleic acid construct as identified in claim 11, said cell being a microbial, prokaryotic or eukaryotic cell.

14. A method for producing, optionally purifying and optionally freeze-drying a polypeptide, said method comprising the steps of:
   i) producing said polypeptide in a cell comprising a nucleic acid construct as defined in claim 11, optionally
   ii) purifying said polypeptide, and optionally
   iii) freeze-drying said purified polypeptide.

15. A method for producing a polypeptide with an enhanced lytic activity comprising treating a polypeptide as obtainable by the method of claim 14 by
i) dialyzing said polypeptide against a buffer comprising a chelating compound,
ii) dialyzing said polypeptide against a divalent metal ion-containing buffer, preferably said divalent metal ion being selected from the group consisting of $Co^{2+}$, $Cu^{2+}$, $Mn^{2+}$ and $Zn^{2+}$.

16. A composition comprising a polypeptide as obtainable by a method as identified in claim 14.

17. The composition according to claim 16, comprising one or more additional active ingredients, preferably selected from the group consisting of a bacteriophage and antibiotic.

18. The composition according to claim 16 for use as a medicament.

19. The composition according to claim 18 for use as a medicament in the treatment of an infectious disease.

20. A method of adding the polypeptide of claim 10 as food additive or disinfectant to prevent growth of Staphylococci microorganisms.

21. A diagnostic method for detecting *Staphylococcus* infection comprising hybridization with the nucleic acid molecule according to claim 1 or where the method comprises an immunological detection comprising the polypeptide encoded by the nucleic acid of claim 1.

22. A method for treating, delaying and/or preventing an infectious disease by administering a composition as defined in claim 16.

23. The nucleic acid molecule according to claim 1, wherein said nucleic acid molecule has at least 80% sequence identity with SEQ ID NO: 1.

24. A cell comprising the expression vector as identified in claim 12, said cell being a microbial, prokaryotic or eukaryotic cell.

25. The nucleic acid molecule according to claim 1, wherein said first nucleotide sequence has at least 95% sequence identity with SEQ ID NO: 12.

26. The nucleic acid molecule according to claim 1, wherein said first nucleotide sequence has at least 98% sequence identity with SEQ ID NO: 12.

27. The nucleic acid molecule according to claim 1, wherein said first nucleotide sequence has 100% sequence identity with SEQ ID NO: 12.

* * * * *

SEQUENCE LISTING

<160> NUMBER OF SEQ ID NOS: 67

<210> SEQ ID NO 1
<211> LENGTH: 1461
<212> TYPE: DNA
<213> ORGANISM: Staphylococcus aureus bacteriophage 2638a

<400> SEQUENCE: 1

```
atgctaactg ctattgacta tcttacgaaa aaaggttgga aaatatcatc tgaccctcgc      60
acttacgatg ttaccctaa  aaactacggc tacagaaatt accatgaaaa cggcattaat     120
tatgatgagt tttgtggtgg ttatcataga gcttttgatg tttacagtaa cgaaactaac     180
gacgtgcctg ctgttactag cggaacagtt attgaagcaa acgattacgg taatttttggt     240 ggtacattcg ttattagaga cgctaacgat aacgattgga tatatgggca tctacaacgt     300
ggctcaatgc gatttgttgt aggcgacaaa gtcaatcaag gtgacattat tggtttacaa     360
ggtaatagca actattacga caatcctatg agtgtacatt tacatttaca attacgccct     420
aaagacgcaa agaaagatga aaaatcacaa gtatgtagtg gtttggctat ggaaaaatat     480
gacattacaa atttaaatgc taaacaagat aaatcaaaga atgggagcgt gaaagagttg     540
aaacatatct attcaaacca tattaaaggt aacaagatta cagcaccaaa acctagtatt     600
```

| | |
|---|---|
| caaggtgtgg tcatccacaa tgattatggt agtatgacac ctagtcaata cttaccatgg | 660 |
| ttatatgcac gtgagaataa cggtacacac gttaacggtt gggctagtgt ttatgcaaat | 720 |
| agaaacgaag tgctttggta tcatccgaca gactacgtag agtggcattg tggtaatcaa | 780 |
| tgggcaaatg ctaacttaat cggatttgaa gtgtgtgagt cgtatcctgg tagaatctcg | 840 |
| gacaaattat tcttagaaaa tgaagaagcg acattgaaag tagctgcgga tgtgatgaag | 900 |
| tcgtacggat taccagttaa tcgcaacact gtacgtctgc ataacgaatt cttcggaact | 960 |
| tcttgtccac atcgttcgtg ggacttgcat gttggcaaag gtgagcctta cacaactact | 1020 |
| aatattaata aaatgaaaga ctacttcatc aaacgcatca acattatta tgacggtgga | 1080 |
| aagctagaag taagcaaagc agcaactatc aaacaatctg acgttaagca agaagttaaa | 1140 |
| aagcaagaag caaacaaat tgtgaaagca acagattgga aacagaataa agatggcatt | 1200 |
| tggtataaag ctgaacatgc ttcgttcaca gtgacagcac cagagggaat tatcacaaga | 1260 |
| tacaaaggtc cttggactgg tcacccacaa gctggtgtat tacaaaaagg tcaaacgatt | 1320 |
| aaatatgatg aggttcaaaa atttgacggt catgtttggg tatcgtggga aacgtttgag | 1380 |
| ggcgaaactg tatacatgcc ggtacgcaca tgggacgcta aaactggtaa agttggtaag | 1440 |
| ttgtggggcg aaattaaata a | 1461 |

<210> SEQ ID NO 2
<211> LENGTH: 1086
<212> TYPE: DNA
<213> ORGANISM: artificial
<220> FEATURE:
<223> OTHER INFORMATION: His-tagged Ami2638_CBD2368

<400> SEQUENCE: 2

| | |
|---|---|
| atgagaggat cgcatcacca tcaccatcac ggatccttac gccctaaaga cgcaaagaaa | 60 |
| gatgaaaaat cacaagtatg tagtggtttg gctatggaaa aatatgacat tacaaattta | 120 |
| aatgctaaac aagataaatc aaagaatggg agcgtgaaag agttgaaaca tatctattca | 180 |
| aaccatatta aaggtaacaa gattacagca ccaaaaccta gtattcaagg tgtggtcatc | 240 |
| cacaatgatt atggtagtat gacacctagt caatacttac catggttata tgcacgtgag | 300 |
| aataacggta cacacgttaa cggttgggct agtgtttatg caaatagaaa cgaagtgctt | 360 |
| tggtatcatc cgacagacta cgtagagtgg cattgtggta atcaatgggc aaatgctaac | 420 |
| ttaatcggat ttgaagtgtg tgagtcgtat cctggtagaa tctcggacaa attattctta | 480 |
| gaaaatgaag aagcgacatt gaagtagct gcggatgtga tgaagtcgta cggattacca | 540 |
| gttaatcgca acactgtacg tctgcataac gaattcttcg gaacttcttg tccacatcgt | 600 |
| tcgtgggact tgcatgttgg caaaggtgag ccttacacaa ctactaatat taataaaatg | 660 |
| aaagactact tcatcaaacg catcaaacat tattatgacg gtggaaagct agaagtaagc | 720 |
| aaagcagcaa ctatcaaaca atctgacgtt aagcaagaag ttaaaaagca agaagcaaaa | 780 |
| caaattgtga aagcaacaga ttggaaacag aataaagatg gcatttggta taaagctgaa | 840 |
| catgcttcgt tcacagtgac agcaccagag ggaattatca agatacaa aggtccttgg | 900 |
| actggtcacc cacaagctgg tgtattacaa aaaggtcaaa cgattaaata tgatgaggtt | 960 |
| caaaaatttg acggtcatgt ttgggtatcg tgggaaacgt ttgagggcga aactgtatac | 1020 |
| atgccggtac gcacatggga cgctaaaact ggtaaagttg gtaagttgtg gggcgaaatt | 1080 |
| aaataa | 1086 |

<210> SEQ ID NO 3
<211> LENGTH: 1035
<212> TYPE: DNA
<213> ORGANISM: artificial
<220> FEATURE:
<223> OTHER INFORMATION: His-tagged M23-2638_CBD2638

<400> SEQUENCE: 3

| | | | | | |
|---|---|---|---|---|---|
| atgagaggat | cgcatcacca | tcaccatcac | ggatccatgc | taactgctat | tgactatctt | 60 |
| acgaaaaaag | gttggaaaat | atcatctgac | cctcgcactt | acgatggtta | ccctaaaaac | 120 |
| tacggctaca | gaaattacca | tgaaaacggc | attaattatg | atgagttttg | tggtggttat | 180 |
| catagagctt | ttgatgttta | cagtaacgaa | actaacgacg | tgcctgctgt | tactagcgga | 240 |
| acagttattg | aagcaaacga | ttacggtaat | tttggtggta | cattcgttat | tagagacgct | 300 |
| aacgataacg | attggatata | tgggcatcta | caacgtggct | caatgcgatt | tgttgtaggc | 360 |
| gacaaagtca | tcaaggtga | cattattggt | ttacaaggta | atagcaacta | ttacgacaat | 420 |
| cctatgagtg | tacatttaca | tttacaatta | cgccctaaag | acgcaaagaa | agatgaaaaa | 480 |
| tcacaagtat | gtagtggttt | ggctatggaa | aaatatgaca | ttacaaattt | aaatgctaaa | 540 |
| caagataaat | caaagaatgg | gagcgtgaaa | gagttgaaac | atatctattc | aaaccatatt | 600 |
| aaaggtaaca | agattacagc | accaaaacct | agtattcaag | gtgagctcgg | tggaaagcta | 660 |
| gaagtaagca | aagcagcaac | tatcaaacaa | tctgacgtta | agcaagaagt | taaaaagcaa | 720 |
| gaagcaaaac | aaattgtgaa | agcaacagat | tggaaacaga | ataaagatgg | catttggtat | 780 |
| aaagctgaac | atgcttcgtt | cacagtgaca | gcaccagagg | gaattatcac | aagatacaaa | 840 |
| ggtccttgga | ctggtcaccc | acaagctggt | gtattacaaa | aggtcaaac | gattaaatat | 900 |
| gatgaggttc | aaaaatttga | cggtcatgtt | tgggtatcgt | gggaaacgtt | tgagggcgaa | 960 |
| actgtataca | tgccggtacg | cacatgggac | gctaaaactg | gtaaagttgg | taagttgtgg | 1020 |
| ggcgaaatta | aataa | | | | | 1035 |

<210> SEQ ID NO 4
<211> LENGTH: 2961
<212> TYPE: DNA
<213> ORGANISM: artificial
<220> FEATURE:
<223> OTHER INFORMATION: His-tagged Ply2638_Ply2638

<400> SEQUENCE: 4

| | | | | | |
|---|---|---|---|---|---|
| atgagaggat | cgcatcacca | tcaccatcac | ggatccatgc | taactgctat | tgactatctt | 60 |
| acgaaaaaag | gttggaaaat | atcatctgac | cctcgcactt | acgatggtta | ccctaaaaac | 120 |
| tacggctaca | gaaattacca | tgaaaacggc | attaattatg | atgagttttg | tggtggttat | 180 |
| catagagctt | ttgatgttta | cagtaacgaa | actaacgacg | tgcctgctgt | tactagcgga | 240 |
| acagttattg | aagcaaacga | ttacggtaat | tttggtggta | cattcgttat | tagagacgct | 300 |
| aacgataacg | attggatata | tgggcatcta | caacgtggct | caatgcgatt | tgttgtaggc | 360 |
| gacaaagtca | tcaaggtga | cattattggt | ttacaaggta | atagcaacta | ttacgacaat | 420 |
| cctatgagtg | tacatttaca | tttacaatta | cgccctaaag | acgcaaagaa | agatgaaaaa | 480 |
| tcacaagtat | gtagtggttt | ggctatggaa | aaatatgaca | ttacaaattt | aaatgctaaa | 540 |
| caagataaat | caaagaatgg | gagcgtgaaa | gagttgaaac | atatctattc | aaaccatatt | 600 |
| aaaggtaaca | agattacagc | accaaaacct | agtattcaag | gtgtggtcat | ccacaatgat | 660 |
| tatggtagta | tgacacctag | tcaatactta | ccatggttat | atgcacgtga | gaataacggt | 720 |

```
acacacgtta acggttgggc tagtgtttat gcaaatagaa acgaagtgct tggtatcat    780
ccgacagact acgtagagtg gcattgtggt aatcaatggg caaatgctaa cttaatcgga   840
tttgaagtgt gtgagtcgta tcctggtaga atctcggaca aattattctt agaaaatgaa   900
gaagcgacat tgaaagtagc tgcggatgtg atgaagtcgt acggattacc agttaatcgc   960
aacactgtac gtctgcataa cgaattcttc ggaacttctt gtccacatcg ttcgtgggac   1020
ttgcatgttg gcaaaggtga gccttacaca actactaata ttaataaaat gaaagactac   1080
ttcatcaaac gcatcaaaca ttattatgac ggtggaaagc tagaagtaag caaagcagca   1140
actatcaaac aatctgacgt taagcaagaa gttaaaaagc aagaagcaaa acaaattgtg   1200
aaagcaacag attggaaaca gaataaagat ggcatttggt ataaagctga acatgcttcg   1260
ttcacagtga cagcaccaga gggaattatc acaagataca aaggtccttg gactggtcac   1320
ccacaagctg gtgtattaca aaaaggtcaa acgattaaat atgatgaggt tcaaaaattt   1380
gacggtcatg tttgggtatc gtgggaaacg tttgagggcg aaactgtata catgccggta   1440
cgcacatggg acgctaaaac tggtaaagtt ggtaagttgt ggggcgaaat taaagagctc   1500
atgctaactc ctattgacta tcttacgaaa aaaggttgga aaatatcatc tgaccctcgc   1560
acttacgatg gttaccctaa aaactacggc tacagaaatt accatgaaaa cggcattaat   1620
tatgatgagt tttgtggtgg ttatcataga gcttttgatg tttacagtaa cgaaactaac   1680
gacgtgcctg ctgttactag cggaacagtt attgaagcaa acgattacgg taattttggt   1740
ggtacattcg ttattagaga cgctaacgat aacgattgga tatatgggca tctacaacgt   1800
ggctcaatgc gatttgttgt aggcgacaaa gtcaatcaag gtgacattat tggtttacaa   1860
ggtaatagca actattacga caatcctatg agtgtacatt tacatttaca attacgccct   1920
aaagacgcaa agaaagatga aaatcacaa gtatgtagtg gtttggctat ggaaaaatat   1980
gacattacaa atttaaatgc taaacaagat aaatcaaaga atgggagcgt gaaagagttg   2040
aaacatatct attcaaacca tattaaaggt aacaagatta cagcaccaaa acctagtatt   2100
caaggtgtgg tcatccacaa tgattatggt agtatgacac ctagtcaata cttaccatgg   2160
ttatatgcac gtgagaataa cggtacacac gttaacggtt gggctagtgt ttatgcaaat   2220
agaaacgaag tgctttggta tcatccgaca gactacgtag agtggcattg tggtaatcaa   2280
tgggcaaatg ctaacttaat cggatttgaa gtgtgtgagt cgtatcctgg tagaatctcg   2340
gacaaattat tcttagaaaa tgaagaagcg acattgaaag tagctgcgga tgtgatgaag   2400
tcgtacggat taccagttaa tcgcaacact gtacgtctgc ataacgaatt cttcggaact   2460
tcttgtccac atcgttcgtg ggacttgcat gttggcaaag gtgagcctta cacaactact   2520
aatattaata aaatgaaaga ctacttcatc aaacgcatca aacattatta tgacggtgga   2580
aagctagaag taagcaaagc agcaactatc aaacaatctg acgttaagca agaagttaaa   2640
aagcaagaag caaaacaaat tgtgaaagca acagattgga aacagaataa agatggcatt   2700
tggtataaag ctgaacatgc ttcgttcaca gtgacagcac cagagggaat tatcacaaga   2760
tacaaaggtc cttggactgg tcacccacaa gctggtgtat acaaaaagg tcaaacgatt   2820
aaatatgatg aggttcaaaa atttgacggt catgtttggg tatcgtggga aacgtttgag   2880
ggcgaaactg tatacatgcc ggtacgcaca tgggacgcta aaactggtaa agttggtaag   2940
ttgtggggcg aaattaaata a                                             2961
```

<210> SEQ ID NO 5

<211> LENGTH: 1983
<212> TYPE: DNA
<213> ORGANISM: artificial
<220> FEATURE:
<223> OTHER INFORMATION: CHAP11_M23-2638_Ami2638_CBD2638

<400> SEQUENCE: 5

```
atgcaagcaa aattaactaa aaatgagttt atagagtggt tgaaaacttc tgagggaaaa      60
caattcaatg tggacttatg gtatggattt caatgctttg attatgccaa tgctggttgg     120
aaagttttgt ttggattact tctaaaaggt ttaggtgcaa agatattcc gttcgctaac      180
aacttcgacg gattagctac tgtataccaa aatacaccgg acttcttagc acaacctggc     240
gacatggtgg tattcggtag caactacggt gctggatatg gtcacgttgc atgggtaatt     300
gaagcaactt tagattacat cattgtatat gagcagaatt ggctaggcgg tggctggact     360
gacggaatcg aacaacccgg ctggggttgg gaaaaagtta agacgaca catgcttat        420
gatttcccta tgtggtttat ccgtccgaat tttaaaagtg agacagccgc acgatcagtt     480
caatctccta cacaagcacc taaaaaagaa acagctggat ccatgctaac tgctattgac     540
tatcttacga aaaaggttg gaaaatatca tctgaccctc gcacttacga tggttaccct     600
aaaaactacg gctacagaaa ttaccatgaa acggcatta attatgatga gttttgtggt      660
ggttatcata gagcttttga tgtttacagt aacgaaacta cgacgtgcc tgctgttact     720
agcggaacag ttattgaagc aaacgattac ggtaattttg gtggtacatt cgttattaga     780
gacgctaacg ataacgattg gatatatggg catctacaac gtggctcaat gcgatttgtt     840
gtaggcgaca aagtcaatca aggtgacatt attggtttac aaggtaatag caactattac     900
gacaatccta tgagtgtaca tttacattta caattcgcc ctaaagacgc aaagaaagat     960
gaaaaatcac aagtatgtag tggtttggct atggaaaaat atgacattac aaattttaaat   1020
gctaaacaag ataaatcaaa gaatgggagc gtgaaagagt tgaaacatat ctattcaaac   1080
catattaaag gtaacaagat tacagcacca aaacctagta ttcaaggtgt ggtcatccac   1140
aatgattatg gtagtatgac acctagtcaa tacttaccat ggttatatgc acgtgagaat   1200
aacggtacac acgttaacgg ttgggctagt gtttatgcaa atagaaacga agtgctttgg   1260
tatcatccga cagactacgt agagtggcat tgtggtaatc aatgggcaaa tgctaactta   1320
atcggatttg aagtgtgtga gtcgtatcct ggtagaatct cggacaaatt attcttagaa   1380
aatgaagaag cgacattgaa agtagctgcg gatgtgatga agtcgtacgg attaccagtt   1440
aatcgcaaca ctgtacgtct gcataacgaa ttcttcggaa cttcttgtcc acatcgttcg   1500
tgggacttgc atgttggcaa aggtgagcct tacacaacta ctaatattaa taaaatgaaa   1560
gactacttca tcaaacgcat caaacattat tatgacggtg gaaagctaga agtaagcaaa   1620
gcagcaacta tcaaacaatc tgacgttaag caagaagtta aaaagcaaga agcaaaacaa   1680
attgtgaaag caacgattg gaaacagaat aaagatggca tttggtataa agctgaacat   1740
gcttcgttca cagtgacagc accagaggga attatcacaa gatacaaagg tccttggact   1800
ggtcacccac aagctggtgt attacaaaaa ggtcaaacga ttaaatatga tgaggttcaa   1860
aaatttgacg gtcatgtttg ggtatcgtgg gaaacgtttg agggcgaaac tgtatacatg   1920
ccggtacgca catgggacgc taaaactggt aaagttggta agttgtgggg cgaaattaaa   1980
taa                                                                  1983
```

<210> SEQ ID NO 6
<211> LENGTH: 2109

<210> TYPE: DNA
<213> ORGANISM: artificial
<220> FEATURE:
<223> OTHER INFORMATION: Ami11_M23-2638_Ami2638_CBD2638

<400> SEQUENCE: 6

```
aagccacaac ctaaagcagt agaacttaaa atcatcaaag atgtggttaa aggttatgac      60
ctacctaagc gtggtagtaa ccctaaaggt atagttatac acaacgacgc agggagcaaa     120
ggggcgactg ctgaagcata tcgtaacgga ttagtaaatg cacctttatc aagattagaa     180
gcgggcattg cgcatagtta cgtatcaggc aacacagttt ggcaagcctt agatgaatca     240
caagtaggtt ggcataccgc taatcaaata ggtaataaat attattacgg tattgaagta     300
tgtcaatcaa tgggcgcaga taacgcgaca ttcttaaaaa atgaacaggc aactttccaa     360
gaatgcgcta gattgttgaa aaaatgggga ttaccagcaa acagaaatac aatcagattg     420
cacaatgaat ttacttcaac atcatgccct catagaagtt cggttttaca cactggtttt     480
gacccagtaa ctcgcggtct attgccagaa gacaagcgt  tgcaacttaa agactacttt     540
atcaagcaga ttagggcgta catggatggt aaaataccgg ttgccactgt ctctaatgag     600
tcaagcgctt caagtaatac agttaaacca gttgcaagtg caggatccat gctaactgct     660
attgactatc ttacgaaaaa aggttggaaa atatcatctg accctcgcac ttacgatggt     720
taccctaaaa actacggcta cagaaattac catgaaaacg gcattaatta tgatgagttt     780
tgtggtggtt atcatagagc ttttgatgtt tacagtaacg aaactaacga cgtgcctgct     840
gttactagcg aacagttat  tgaagcaaac gattacggta attttggtgg tacattcgtt     900
attagagacg ctaacgataa cgattggata tatgggcatc tacaacgtgg ctcaatgcga     960
tttgttgtag cgacaaagt  caatcaaggt gacattattg gtttacaagg taatagcaac    1020
tattacgaca atcctatgag tgtacattta catttacaat tacgccctaa agacgcaaag    1080
aaagatgaaa aatcacaagt atgtagtggt ttggctatgg aaaaatatga cattacaaat    1140
ttaaatgcta acaagataa  atcaaagaat gggagcgtga aagagttgaa acatatctat    1200
tcaaaccata ttaaaggtaa caagattaca gcaccaaaac ctagtattca aggtgtggtc    1260
atccacaatg attatggtag tatgacacct agtcaatact taccatggtt atatgcacgt    1320
gagaataacg gtacacacgt taacggttgg gctagtgttt atgcaaatag aaacgaagtg    1380
ctttggtatc atccgacaga ctacgtagag tggcattgtg gtaatcaatg gcaaatgct     1440
aacttaatcg gatttgaagt gtgtgagtcg tatcctggta gaatctcgga caaattattc    1500
ttagaaaatg aagaagcgac attgaaagta gctgcggatg tgatgaagtc gtacggatta    1560
ccagttaatc gcaacactgt acgtctgcat aacgaattct tcggaacttc ttgtccacat    1620
cgttcgtggg acttgcatgt tggcaaaggt gagccttaca caactactaa tattaataaa    1680
atgaaagact acttcatcaa acgcatcaaa cattattatg acggtggaaa gctagaagta    1740
agcaaagcag caactatcaa acaatctgac gttaagcaag aagttaaaaa gcaagaagca    1800
aaacaaattg tgaaagcaac agattggaaa cagaataaag atggcatttg gtataaagct    1860
gaacatgctt cgttcacagt gacagcacca gagggaatta tcacaagata caaaggtcct    1920
tggactggtc acccacaagc tggtgtatta caaaaaggtc aaacgattaa atatgatgag    1980
gttcaaaaat ttgacggtca tgtttgggta tcgtgggaaa cgtttgaggg cgaaactgta    2040
tacatgccgg tacgcacatg ggacgctaaa actggtaaag ttggtaagtt gtggggcgaa    2100
attaaataa                                                            2109
```

<210> SEQ ID NO 7
<211> LENGTH: 1923
<212> TYPE: DNA
<213> ORGANISM: artificial
<220> FEATURE:
<223> OTHER INFORMATION: CHAPTw_Ami2638_M23-LST_CBD2638

<400> SEQUENCE: 7

| | | | | | | |
|---|---|---|---|---|---|---|
| atgaaaccc | tgaaacaagc | agagtcctac | attaagagta | aagtaaatac | aggaactgat | 60 |
| tttgatggtt | tatatgggta | tcagtgtatg | gacttagcag | tagattatat | ttaccatgta | 120 |
| acagatggta | aaataagaat | gtggggtaat | gctaaggatg | cgataaataa | ctcttttggt | 180 |
| ggtactgcta | cggtatataa | aaactaccct | gcttttagac | ctaagtacgg | tgatgtagtc | 240 |
| gtatggacta | ctggtaattt | tgcaacttat | ggtcatatcg | caatagttac | taaccctgac | 300 |
| ccttatggag | accttcaata | tgttacagtt | cttgaacaaa | actggaacgg | taacgggatt | 360 |
| tataaaaccg | agttagctac | aatcagaaca | cacgattaca | caggaattac | acattttatt | 420 |
| aaagacgcaa | agaaagatga | aaaatcacaa | gtatgtagtg | gtttggctat | ggaaaaatat | 480 |
| gacattacaa | atttaaatgc | taaacaagat | aaatcaaaga | atgggagcgt | gaaagagttg | 540 |
| aaacatatct | attcaaacca | tattaaaggt | aacaagatta | cagcaccaaa | acctagtatt | 600 |
| caaggtgtgg | tcatccacaa | tgattatggt | agtatgacac | ctagtcaata | cttaccatgg | 660 |
| ttatatgcac | gtgagaataa | cggtacacac | gttaacggtt | gggctagtgt | ttatgcaaat | 720 |
| agaaacgaag | tgctttggta | tcatccgaca | gactacgtag | agtggcattg | tggtaatcaa | 780 |
| tgggcaaatg | ctaacttaat | cggatttgaa | gtgtgtgagt | cgtatcctgg | tagaatctcg | 840 |
| gacaaattat | tcttagaaaa | tgaagaagcg | acattgaaag | tagctgcgga | tgtgatgaag | 900 |
| tcgtacggat | taccagttaa | tcgcaacact | gtacgtctgc | ataacgaatt | cttcggaact | 960 |
| tcttgtccac | atcgttcgtg | ggacttgcat | gttggcaaag | gtgagcctta | cacaactact | 1020 |
| aatattaata | aaatgaaaga | ctacttcatc | aaacgcatca | acattatta | tgacggtgga | 1080 |
| aagctagaag | taagcaaagc | agcaactatc | aaacaatctg | acgttaagca | agaagttaaa | 1140 |
| aagcaagaag | caaacaaat | tgtgaaagca | acagatgctg | caacacatga | acattcagca | 1200 |
| caatggttga | ataattacaa | aaaaggatat | ggttacggtc | cttatccatt | aggtataaat | 1260 |
| ggcggtatgc | actacggagt | tgattttttt | atgaatattg | gaacaccagt | aaaagctatt | 1320 |
| tcaagcggaa | aaatagttga | agctggttgg | agtaattacg | gaggaggtaa | tcaaataggt | 1380 |
| cttattgaaa | atgatggagt | gcatagacaa | tggtatatgc | atctaagtaa | atataatgtt | 1440 |
| aaagtaggag | attatgtcaa | agctggtcaa | ataatcggtt | ggtctggaag | cactggttat | 1500 |
| tctacagcac | cacatttaca | cttccaaaga | atggttaatt | cattttcaaa | ttcaactgcc | 1560 |
| caagatccaa | tgcctttctt | aaagagcgca | ggatatggaa | aagcaggtgg | tacagtaact | 1620 |
| ccaacgccga | atacaggttg | gaaacagaat | aaagatggca | tttggtataa | agctgaacat | 1680 |
| gcttcgttca | cagtgacagc | accagaggga | attatcacaa | gatacaaagg | tccttggact | 1740 |
| ggtcacccac | aagctggtgt | attacaaaaa | ggtcaaacga | ttaaatatga | tgaggttcaa | 1800 |
| aaatttgacg | gtcatgtttg | ggtatcgtgg | gaaacgtttg | agggcgaaac | tgtatacatg | 1860 |
| ccggtacgca | catgggacgc | taaaactggt | aaagttggta | agttgtgggg | cgaaattaaa | 1920 |
| taa | | | | | | 1923 |

<210> SEQ ID NO 8
<211> LENGTH: 1953

```
<212> TYPE: DNA
<213> ORGANISM: artificial
<220> FEATURE:
<223> OTHER INFORMATION: His-tagged CHAPTw_Ami2638_M23-LST_CWT-LST

<400> SEQUENCE: 8
atgagaggat cgcatcacca tcaccatcac ggatccatga aaaccctgaa acaagcagag      60
tcctacatta agagtaaagt aaatacagga actgattttg atggtttata tgggtatcag     120
tgtatggact tagcagtaga ttatatttac catgtaacag atggtaaaat aagaatgtgg     180
ggtaatgcta aggatgcgat aaataactct tttggtggta ctgctacggt atataaaaac     240
taccctgctt tagacctaa gtacggtgat gtagtcgtat ggactactgg taattttgca      300
acttatggtc atatcgcaat agttactaac cctgacccct atggagacct tcaatatgtt     360
acagttcttg aacaaaactg gaacggtaac gggatttata aaccgagtt agctacaatc      420
agaacacacg attacacagg aattacacat tttattaaag acgcaaagaa agatgaaaaa     480
tcacaagtat gtagtggttt ggctatggaa aaatatgaca ttacaaattt aaatgctaaa     540
caagataaat caagaatgg gagcgtgaaa gagttgaaac atatctattc aaaccatatt      600
aaaggtaaca agattacagc accaaaacct agtattcaag gtgtggtcat ccacaatgat     660
tatggtagta tgacacctag tcaatactta ccatggttat atgcacgtga gaataacggt     720
acacacgtta acggttgggc tagtgtttat gcaaatagaa acgaagtgct ttggtatcat     780
ccgacagact acgtagagtg gcattgtggt aatcaatggg caaatgctaa cttaatcgga     840
tttgaagtgt gtgagtcgta tcctggtaga atctcggaca aattattctt agaaaatgaa     900
gaagcgacat tgaaagtagc tgcggatgtg atgaagtcgt acggattacc agttaatcgc     960
aacactgtac gtctgcataa cgaattcttc ggaacttctt gtccacatcg ttcgtgggac    1020
ttgcatgttg gcaaaggtga gccttacaca actactaata ttaataaaat gaaagactac    1080
ttcatcaaac gcatcaaaca ttattatgac ggtggaaagc tagaagtaag caaagcagca    1140
actatcaaac aatctgacgt taagcaagaa gttaaaaagc aagaagcaaa acaaattgtg    1200
aaagcaacag atgctgcaac acatgaacat tcagcacaat ggttgaataa ttacaaaaaa    1260
ggatatggtt acgtccctta tccattaggt ataaatggcg gtatgcacta cggagttgat    1320
tttttttatga atattggaac accagtaaaa gctatttcaa gcggaaaaat agttgaagct    1380
ggttggagta attacggagg aggtaatcaa ataggtctta ttgaaaatga tggagtgcat    1440
agacaatggt atatgcatct aagtaaatat aatgttaaag taggagatta tgtcaaagct    1500
ggtcaaataa tcggttggtc tggaagcact ggttattcta cagcaccaca tttacacttc    1560
caaagaatgg ttaattcatt ttcaaattca actgcccaag atccaatgcc tttcttaaag    1620
agcgcaggat atgaaaaagc aggtggtaca gtaactccaa cgccgaatac aggttggaaa    1680
acaaacaaat atggcacact atataaatca gagtcagcta gcttcacacc taatacagat    1740
ataataacaa gaacgactgg tccatttaga agcatgccgc agtcaggagt cttaaaagca    1800
ggtcaaacaa ttcattatga tgaagtgatg aaacaagacg gtcatgtttg ggtaggttat    1860
acaggtaaca gtggccaacg tatttacttg cctgtaagaa catggaataa atctactaat    1920
actttaggtg ttctttgggg aactataaag taa                                  1953

<210> SEQ ID NO 9
<211> LENGTH: 1518
<212> TYPE: DNA
<213> ORGANISM: artificial
<220> FEATURE:
```

<223> OTHER INFORMATION: M23-LST_Ami2638_CBD2638

<400> SEQUENCE: 9

```
gctgcaacac atgaacattc agcacaatgg ttgaataatt acaaaaaagg atatggttac    60
ggtccttatc cattaggtat aaatggcggt atgcactacg gagttgattt ttttatgaat   120
attggaacac cagtaaaagc tatttcaagc ggaaaaatag ttgaagctgg ttggagtaat   180
tacggaggag gtaatcaaat aggtcttatt gaaaatgatg gagtgcatag acaatggtat   240
atgcatctaa gtaaatataa tgttaaagta ggagattatg tcaaagctgg tcaaataatc   300
ggttggtctg gaagcactgg ttattctaca gcaccacatt tacacttcca agaatggtt    360
aattcatttt caaattcaac tgcccaagat ccaatgcctt tcttaaagag cgcaggatat   420
ggaaaagcag gtggtacagt aactccaacg ccgaatacag gtgagctctt acgccctaaa   480
gacgcaaaga aagatgaaaa atcacaagta tgtagtggtt tggctatgga aaaatatgac   540
attacaaatt taaatgctaa acaagataaa tcaagaatg ggagcgtgaa agagttgaaa    600
catatctatt caaaccatat taaaggtaac aagattacag caccaaaacc tagtattcaa   660
ggtgtggtca tccacaatga ttatggtagt atgacaccta gtcaatactt accatggtta   720
tatgcacgtg agaataacgg tacacacgtt aacggttggg ctagtgttta tgcaaataga   780
aacgaagtgc tttggtatca tccgacagac tacgtagagt ggcattgtgg taatcaatgg   840
gcaaatgcta acttaatcgg atttgaagtg tgtgagtcgt atcctggtag aatctcggac   900
aaattattct tagaaaatga agaagcgaca ttgaaagtag ctgcggatgt gatgaagtcg   960
tacgattac cagttaatcg caacactgta cgtctgcata cgaattctt cggaacttct    1020
tgtccacatc gttcgtggga cttgcatgtt ggcaaaggtg agccttacac aactactaat  1080
attaataaaa tgaaagacta cttcatcaaa cgcatcaaac attattatga cggtggaaag  1140
ctagaagtaa gcaaagcagc aactatcaaa caatctgacg ttaagcaaga agttaaaaag  1200
caagaagcaa aacaaattgt gaaagcaaca gattggaaac agaataaaga tggcatttgg  1260
tataaagctg aacatgcttc gttcacagtg acagcaccag agggaattat cacaagatac  1320
aaaggtcctt ggactggtca cccacaagct ggtgtattac aaaaaggtca acgattaaa   1380
tatgatgagg ttcaaaaatt tgacggtcat gtttgggtat cgtgggaaac gtttgagggc  1440
gaaactgtat acatgccggt acgcacatgg gacgctaaaa ctggtaaagt tggtaagttg  1500
tgggcgaaa ttaaataa                                                  1518
```

<210> SEQ ID NO 10
<211> LENGTH: 1521
<212> TYPE: DNA
<213> ORGANISM: artificial
<220> FEATURE:
<223> OTHER INFORMATION: His-tagged LST_LST

<400> SEQUENCE: 10

```
atgagaggat cgcatcacca tcaccatcac ggatccgctg caacacatga acattcagca    60
caatggttga ataattacaa aaaaggatat ggttacggtc cttatccatt aggtataaat   120
ggcggtatgc actacggagt tgattttttt atgaatattg aacaccagt aaaagctatt    180
tcaagcggaa aaatagttga agctggttgg agtaattacg gaggaggtaa tcaaataggt   240
cttattgaaa atgatggagt gcatagacaa tggtatatgc atctaagtaa atataatgtt   300
aaagtaggag attatgtcaa agctggtcaa ataatcggtt ggtctggaag cactggttat   360
tctacagcac cacatttaca cttccaaaga atggttaatt cattttcaaa ttcaactgcc   420
```

```
caagatccaa tgccttctt aaagagcgca ggatatggaa aagcaggtgg tacagtaact      480
ccaacgccga atacaggttg aaaacaaac aaatatggca cactatataa atcgagtca      540 gctagcttca cacctaatac agatataata acaagaacga ctggtccatt tagaagcatg      600
ccgcagtcag gagtcttaaa agcaggtcaa acaattcatt atgatgaagt gatgaaacaa      660
gacggtcatg tttgggtagg ttatacaggt aacagtggcc aacgtattta cttgcctgta      720
agaacatgga ataaatctac taatacttta ggtgttcttt ggggaactat aaaggagctc      780
gctgcaacac atgaacattc agcacaatgg ttgaataatt acaaaaaagg atatggttac      840
ggtccttatc cattaggtat aaatggcggt atgcactacg gagttgattt ttttatgaat      900
attggaacac cagtaaaagc tatttcaagc ggaaaaatag ttgaagctgg ttggagtaat      960
tacggaggag gtaatcaaat aggtcttatt gaaaatgatg gagtgcatag acaatggtat     1020
atgcatctaa gtaaatataa tgttaaagta ggagattatg tcaaagctgg tcaaataatc     1080
ggttggtctg gaagcactgg ttattctaca gcaccacatt tacacttcca agaatggtt     1140 aattcatttt caaattcaac tgcccaagat ccaatgcctt tcttaaagag cgcaggatat     1200
ggaaaagcag gtggtacagt aactccaacg ccgaatacag gttggaaaac aaacaaatat     1260
ggcacactat ataaatcaga gtcagctagc ttcacaccta atacagatat aataacaaga     1320
acgactggtc catttagaag catgccgcag tcaggagtct aaaagcagg tcaaacaatt     1380 cattatgatg aagtgatgaa acaagacggt catgtttggg taggttatac aggtaacagt     1440
ggccaacgta tttacttgcc tgtaagaaca tggaataaat ctactaatac tttaggtgtt     1500
ctttggggaa ctataaagtg a                                             1521
```

<210> SEQ ID NO 11
<211> LENGTH: 1245
<212> TYPE: DNA
<213> ORGANISM: artificial
<220> FEATURE:
<223> OTHER INFORMATION: His-tagged M23-LST_M23_LST-CWT-LST

<400> SEQUENCE: 11

```
atgagaggat cgcatcacca tcaccatcac ggatccgctg caacacatga acattcagca       60
caatggttga ataattacaa aaaaggatat ggttacggtc cttatccatt aggtataaat      120
ggcggtatgc actacggagt tgattttttt atgaatattg gaacaccagt aaaagctatt      180
tcaagcggaa aaatagttga agctggttgg agtaattacg gaggaggtaa tcaaataggt      240
cttattgaaa atgatggagt gcatagacaa tggtatatgc atctaagtaa atataatgtt      300
aaagtaggag attatgtcaa agctggtcaa ataatcggtt ggtctggaag cactggttat      360
tctacagcac acatttaca cttccaaaga atggttaatt cattttcaaa ttcaactgcc      420
caagatccaa tgccttctt aaagagcgca ggatatggaa aagcaggtgg tacagtaact      480
ccaacgccga atacaggtga gctcgctgca acacatgaac attcagcaca atggttgaat      540
aattacaaaa aaggatatgg ttacggtcct tatccattag gtataaatgg cggtatgcac      600
tacggagttg attttttat gaatattgga acaccagtaa aagctatttc aagcggaaaa      660
atagttgaag ctggttggag taattacgga ggaggtaatc aaataggtct tattgaaaat      720
gatggagtgc atagacaatg gtatatgcat ctaagtaaat ataatgttaa agtaggagat      780
tatgtcaaag ctggtcaaat aatcggttgg tctggaagca ctggttattc tacagcacca      840
catttacact tccaaagaat ggttaattca ttttcaaatt caactgccca agatccaatg      900
```

```
ccttttctta agagcgcagg atatggaaaa gcaggtggta cagtaactcc aacgccgaat    960
acaggttgga aaacaaacaa atatggcaca ctatataaat cagagtcagc tagcttcaca   1020
cctaatacag atataataac aagaacgact ggtccattta gaagcatgcc gcagtcagga   1080
gtcttaaaag caggtcaaac aattcattat gatgaagtga tgaaacaaga cggtcatgtt   1140
tgggtaggtt atacaggtaa cagtggccaa cgtatttact tgcctgtaag aacatggaat   1200
aaatctacta atactttagg tgttctttgg ggaactataa agtga                   1245
```

<210> SEQ ID NO 12
<211> LENGTH: 285
<212> TYPE: DNA
<213> ORGANISM: Staphylococcus aureus bacteriophage 2638a

<400> SEQUENCE: 12

```
tggaaacaga ataagatgg catttggtat aaagctgaac atgcttcgtt cacagtgaca     60
gcaccagagg gaattatcac aagatacaaa ggtccttgga ctggtcaccc acaagctggt   120
gtattacaaa aaggtcaaac gattaaatat gatgaggttc aaaaatttga cggtcatgtt   180
tgggtatcgt gggaaacgtt tgagggcgaa actgtataca tgccggtacg cacatgggac   240
gctaaaactg gtaaagttgg taagttgtgg ggcgaaatta aataa                   285
```

<210> SEQ ID NO 13
<211> LENGTH: 279
<212> TYPE: DNA
<213> ORGANISM: Staphylococcus simulans

<400> SEQUENCE: 13

```
tggaaaacaa acaaatatgg cacactatat aaatcagagt cagctagctt cacacctaat    60
acagatataa taacaagaac gactggtcca tttagaagca tgccgcagtc aggagtctta   120
aaagcaggtc aaacaattca ttatgatgaa gtgatgaaac aagacggtca tgtttgggta   180
ggttatacag gtaacagtgg ccaacgtatt tacttgcctg taagaacatg gaataaatct   240
actaatactt taggtgttct ttggggaact ataaagtga                          279
```

<210> SEQ ID NO 14
<211> LENGTH: 438
<212> TYPE: DNA
<213> ORGANISM: Staphylococcus aureus bacteriophage 2638a

<400> SEQUENCE: 14

```
atgctaactg ctattgacta tcttacgaaa aaaggttgga aatatcatc tgaccctcgc     60 acttacgatg gttaccctaa aaactacggc tacagaaatt accatgaaaa cggcattaat   120
tatgatgagt tttgtggtgg ttatcataga gcttttgatg tttacagtaa cgaaactaac   180
gacgtgcctg ctgttactag cggaacagtt attgaagcaa acgattacgg taattttggt   240
ggtacattcg ttattagaga cgctaacgat aacgattgga tatatgggca tctacaacgt   300
ggctcaatgc gatttgttgt aggcgacaaa gtcaatcaag gtgacattat tggtttacaa   360
ggtaatagca actattacga caatcctatg agtgtacatt tacatttaca attacgccct   420
aaagacgcaa agaaagat                                                 438
```

<210> SEQ ID NO 15
<211> LENGTH: 420
<212> TYPE: DNA
<213> ORGANISM: Staphylococcus simulans

<400> SEQUENCE: 15

```
gctgcaacac atgaacattc agcacaatgg ttgaataatt acaaaaaagg atatggttac    60
ggtccttatc cattaggtat aaatggcggt atgcactacg gagttgattt ttttatgaat   120
attggaacac cagtaaaagc tatttcaagc ggaaaaatag ttgaagctgg ttggagtaat   180
tacggaggag gtaatcaaat aggtcttatt gaaaatgatg gagtgcatag acaatggtat   240
atgcatctaa gtaaatataa tgttaaagta ggagattatg tcaaagctgg tcaaataatc   300
ggttggtctg gaagcactgg ttattctaca gcaccacatt tacacttcca agaatggtt    360 aattcatttt caaattcaac tgcccaagat ccaatgcctt tcttaaagag cgcaggatat   420
```

<210> SEQ ID NO 16
<211> LENGTH: 510
<212> TYPE: DNA
<213> ORGANISM: Staphylococcus aureus bacteriophage 2638a

<400> SEQUENCE: 16

```
ggtaacaaga ttacagcacc aaaacctagt attcaaggtg tggtcatcca caatgattat    60
ggtagtatga cacctagtca atacttacca tggttatatg cacgtgagaa taacggtaca   120
cacgttaacg gttgggctag tgtttatgca aatagaaacg aagtgctttg gtatcatccg   180
acagactacg tagagtggca ttgtggtaat caatgggcaa atgctaactt aatcggattt   240
gaagtgtgtg agtcgtatcc tggtagaatc tcggacaaat tattcttaga aaatgaagaa   300
gcgacattga aagtagctgc ggatgtgatg aagtcgtacg gattaccagt taatcgcaac   360
actgtacgtc tgcataacga attcttcgga acttcttgtc cacatcgttc gtgggacttg   420
catgttggca aaggtgagcc ttacacaact actaatatta ataaaatgaa agactacttc   480
atcaaacgca tcaaacatta ttatgacggt                                     510
```

<210> SEQ ID NO 17
<211> LENGTH: 642
<212> TYPE: DNA
<213> ORGANISM: Staphylococcus aureus phage phi 11

<400> SEQUENCE: 17

```
aagccacaac ctaaagcagt agaacttaaa atcatcaaag atgtggttaa aggttatgac    60
ctacctaagc gtggtagtaa ccctaaaggt atagttatac acaacgacgc agggagcaaa   120
ggggcgactc tgaagcata tcgtaacgga ttagtaaatg caccttttatc aagattagaa   180 gcgggcattg cgcatagtta cgtatcaggc aacacagttt ggcaagcctt agatgaatca   240
caagtaggtt ggcataccgc taatcaaata ggtaataaat attattacgg tattgaagta   300
tgtcaatcaa tgggcgcaga taacgcgaca ttcttaaaaa atgaacaggc aactttccaa   360
gaatgcgcta gattgttgaa aaaatgggga ttaccagcaa acagaaatac aatcagattg   420
cacaatgaat ttacttcaac atcatgccct catagaagtt cggttttaca cactggtttt   480
gacccagtaa ctcgcggtct attgccagaa gacaagcgt tgcaacttaa agactacttt   540
atcaagcaga ttagggcgta catggatggt aaaataccgg ttgccactgt ctctaatgag   600
tcaagcgctt caagtaatac agttaaacca gttgcaagtg ca                     642
```

<210> SEQ ID NO 18
<211> LENGTH: 516
<212> TYPE: DNA
<213> ORGANISM: Staphylococcus aureus phage phi 11

<400> SEQUENCE: 18

```
atgcaagcaa aattaactaa aaatgagttt atagagtggt tgaaaacttc tgagggaaaa    60
caattcaatg tggacttatg gtatggattt caatgctttg attatgccaa tgctggttgg   120
aaagttttgt ttggattact tctaaaaggt ttaggtgcaa agatattcc gttcgctaac    180 aacttcgacg gattagctac tgtataccaa aatacaccgg acttcttagc acaacctggc   240
gacatggtgg tattcggtag caactacggt gctggatatg gtcacgttgc atgggtaatt   300
gaagcaactt tagattacat cattgtatat gagcagaatt ggctaggcgg tggctggact   360
gacggaatcg aacaacccgg ctggggttgg gaaaaagtta caagacgaca acatgcttat   420
gatttcccta tgtggtttat ccgtccgaat tttaaaagtg agacagcgcc acgatcagtt   480
caatctccta cacaagcacc taaaaaagaa acagct                              516
```

<210> SEQ ID NO 19
<211> LENGTH: 420
<212> TYPE: DNA
<213> ORGANISM: Staphylococcus phage Twort

<400> SEQUENCE: 19

```
atgaaaaccc tgaaacaagc agagtcctac attaagagta aagtaaatac aggaactgat    60
tttgatggtt tatatgggta tcagtgtatg gacttagcag tagattatat ttaccatgta   120
acagatggta aataagaat gtggggtaat gctaaggatg cgataaataa ctcttttggt    180
ggtactgcta cggtatataa aaactaccct gcttttagac ctaagtacgg tgatgtagtc   240
gtatggacta ctggtaattt tgcaacttat ggtcatatcg caatagttac taaccctgac   300
ccttatggag accttcaata tgttacagtt cttgaacaaa actggaacgg taacgggatt   360
tataaaaccg agttagctac aatcagaaca cacgattaca caggaattac acattttatt   420
```

<210> SEQ ID NO 20
<211> LENGTH: 1851
<212> TYPE: DNA
<213> ORGANISM: artificial
<220> FEATURE:
<223> OTHER INFORMATION: M23-2638_Ami2638_CBD2638_CBD2638

<400> SEQUENCE: 20

```
atgctaactg ctattgacta tcttacgaaa aaaggttgga aaatatcatc tgaccctcgc    60
acttacgatg gttaccctaa aaactacggc tacagaaatt accatgaaaa cggcattaat   120
tatgatgagt tttgtggtgg ttatcataga gcttttgatg tttacagtaa cgaaactaac   180
gacgtgcctg ctgttactag cggaacagtt attgaagcaa acgattacgg taattttggt   240
ggtacattcg ttattagaga cgctaacgat aacgattgga tatatgggca tctacaacgt   300
ggctcaatgc gatttgttgt aggcgacaaa gtcaatcaag gtgacattat tggtttacaa   360
ggtaatagca actattacga caatcctatg agtgtacatt tacatttaca attacgccct   420
aaagacgcaa agaagatga aaatcacaa gtatgtagtg gtttggctat ggaaaaatat    480
gacattacaa atttaaatgc taaacaagat aaatcaaaga atgggagcgt gaaagagttg   540
aaacatatct attcaaacca tattaaaggt aacaagatta cagcaccaaa acctagtatt   600
caaggtgtgg tcatccacaa tgattatggt agtatgacac ctagtcaata cttaccatgg   660
ttatatgcac gtgagaataa cggtacacac gttaacggtt gggctagtgt ttatgcaaat   720
agaaacgaag tgctttggta tcatccgaca gactacgtag agtggcattg tggtaatcaa   780
tgggcaaatg ctaacttaat cggatttgaa gtgtgtgagt cgtatcctgg tagaatctcg   840
gacaaattat tcttagaaaa tgaagaagcg acattgaaag tagctgcgga tgtgatgaag   900
```

-continued

```
tcgtacggat taccagttaa tcgcaacact gtacgtctgc ataacgaatt cttcggaact    960
tcttgtccac atcgttcgtg ggacttgcat gttggcaaag gtgagcctta cacaactact   1020
aatattaata aaatgaaaga ctacttcatc aaacgcatca acattatta tgacggtgga    1080 aagctagaag taagcaaagc agcaactatc aaacaatctg acgttaagca agaagttaaa   1140
aagcaagaag caaaacaaat tgtgaaagca acagattgga aacagaataa agatggcatt   1200
tggtataaag ctgaacatgc ttcgttcaca gtgacagcac cagagggaat tatcacaaga   1260
tacaaaggtc cttggactgg tcacccacaa gctggtgtat tacaaaaagg tcaaacgatt   1320
aaatatgatg aggttcaaaa atttgacggt catgtttggg tatcgtggga aacgtttgag   1380
ggcgaaactg tatacatgcc ggtacgcaca tgggacgcta aaactggtaa agttggtaag   1440
ttgtggggcg aaattaaaga gctcggtgga aagctagaag taagcaaagc agcaactatc   1500
aaacaatctg acgttaagca agaagttaaa aagcaagaag caaaacaaat tgtgaaagca   1560
acagattgga aacagaataa agatggcatt tggtataaag ctgaacatgc ttcgttcaca   1620
gtgacagcac cagagggaat tatcacaaga tacaaaggtc cttggactgg tcacccacaa   1680
gctggtgtat tacaaaaagg tcaaacgatt aaatatgatg aggttcaaaa atttgacggt   1740
catgtttggg tatcgtggga aacgtttgag ggcgaaactg tatacatgcc ggtacgcaca   1800
tgggacgcta aaactggtaa agttggtaag ttgtggggcg aaattaaata a            1851
```

```
<210> SEQ ID NO 21
<211> LENGTH: 498
<212> TYPE: PRT
<213> ORGANISM: artificial
<220> FEATURE:
<223> OTHER INFORMATION: His-tagged Ply2638

<400> SEQUENCE: 21

Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Tyr Gly Tyr Arg Asn Tyr His Glu
        35                  40                  45

Asn Gly Ile Asn Tyr Asp Glu Phe Cys Gly Gly Tyr His Arg Ala Phe
    50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
    130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190
```

```
Lys His Ile Tyr Ser Asn His Ile Lys Gly Asn Lys Ile Thr Ala Pro
            195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln
370                 375                 380

Ser Asp Val Lys Gln Glu Val Lys Lys Gln Glu Ala Lys Gln Ile Val
385                 390                 395                 400

Lys Ala Thr Asp Trp Lys Gln Asn Lys Asp Gly Ile Trp Tyr Lys Ala
                405                 410                 415

Glu His Ala Ser Phe Thr Val Thr Ala Pro Glu Gly Ile Ile Thr Arg
            420                 425                 430

Tyr Lys Gly Pro Trp Thr Gly His Pro Gln Ala Gly Val Leu Gln Lys
        435                 440                 445

Gly Gln Thr Ile Lys Tyr Asp Glu Val Gln Lys Phe Asp Gly His Val
450                 455                 460

Trp Val Ser Trp Glu Thr Phe Glu Gly Glu Thr Val Tyr Met Pro Val
465                 470                 475                 480

Arg Thr Trp Asp Ala Lys Thr Gly Lys Val Gly Lys Leu Trp Gly Glu
                485                 490                 495

Ile Lys

<210> SEQ ID NO 22
<211> LENGTH: 361
<212> TYPE: PRT
<213> ORGANISM: artificial
<220> FEATURE:
<223> OTHER INFORMATION: His-tagged Ami2638_CBD2638

<400> SEQUENCE: 22

Met Arg Gly Ser His His His His His His Gly Ser Leu Arg Pro Lys
1               5                   10                  15

Asp Ala Lys Lys Asp Glu Lys Ser Gln Val Cys Ser Gly Leu Ala Met
            20                  25                  30

Glu Lys Tyr Asp Ile Thr Asn Leu Asn Ala Lys Gln Asp Lys Ser Lys
        35                  40                  45

Asn Gly Ser Val Lys Glu Leu Lys His Ile Tyr Ser Asn His Ile Lys
```

```
                    50                  55                  60
Gly Asn Lys Ile Thr Ala Pro Lys Pro Ser Ile Gln Gly Val Val Ile
 65                  70                  75                  80

His Asn Asp Tyr Gly Ser Met Thr Pro Ser Gln Tyr Leu Pro Trp Leu
                 85                  90                  95

Tyr Ala Arg Glu Asn Asn Gly Thr His Val Asn Gly Trp Ala Ser Val
                100                 105                 110

Tyr Ala Asn Arg Asn Glu Val Leu Trp Tyr His Pro Thr Asp Tyr Val
                115                 120                 125

Glu Trp His Cys Gly Asn Gln Trp Ala Asn Ala Asn Leu Ile Gly Phe
        130                 135                 140

Glu Val Cys Glu Ser Tyr Pro Gly Arg Ile Ser Asp Lys Leu Phe Leu
145                 150                 155                 160

Glu Asn Glu Glu Ala Thr Leu Lys Val Ala Ala Asp Val Met Lys Ser
                165                 170                 175

Tyr Gly Leu Pro Val Asn Arg Asn Thr Val Arg Leu His Asn Glu Phe
                180                 185                 190

Phe Gly Thr Ser Cys Pro His Arg Ser Trp Asp Leu His Val Gly Lys
        195                 200                 205

Gly Glu Pro Tyr Thr Thr Thr Asn Ile Asn Lys Met Lys Asp Tyr Phe
210                 215                 220

Ile Lys Arg Ile Lys His Tyr Tyr Asp Gly Gly Lys Leu Glu Val Ser
225                 230                 235                 240

Lys Ala Ala Thr Ile Lys Gln Ser Asp Val Lys Gln Glu Val Lys Lys
                245                 250                 255

Gln Glu Ala Lys Gln Ile Val Lys Ala Thr Asp Trp Lys Gln Asn Lys
        260                 265                 270

Asp Gly Ile Trp Tyr Lys Ala Glu His Ala Ser Phe Thr Val Thr Ala
                275                 280                 285

Pro Glu Gly Ile Ile Thr Arg Tyr Lys Gly Pro Trp Thr Gly His Pro
        290                 295                 300

Gln Ala Gly Val Leu Gln Lys Gly Gln Thr Ile Lys Tyr Asp Glu Val
305                 310                 315                 320

Gln Lys Phe Asp Gly His Val Trp Val Ser Trp Glu Thr Phe Glu Gly
                325                 330                 335

Glu Thr Val Tyr Met Pro Val Arg Thr Trp Asp Ala Lys Thr Gly Lys
                340                 345                 350

Val Gly Lys Leu Trp Gly Glu Ile Lys
        355                 360

<210> SEQ ID NO 23
<211> LENGTH: 344
<212> TYPE: PRT
<213> ORGANISM: artificial
<220> FEATURE:
<223> OTHER INFORMATION: His-tagged M23-2638_CBD2638

<400> SEQUENCE: 23

Met Arg Gly Ser His His His His His His Gly Ser Met Leu Thr Ala
 1               5                  10                  15

Ile Asp Tyr Leu Thr Lys Lys Gly Trp Lys Ile Ser Ser Asp Pro Arg
                 20                  25                  30

Thr Tyr Asp Gly Tyr Pro Lys Asn Gly Tyr Arg Asn Tyr His Glu
             35                  40                  45

Asn Gly Ile Asn Tyr Asp Glu Phe Cys Gly Gly Tyr His Arg Ala Phe
```

```
                  50                  55                  60
Asp Val Tyr Ser Asn Glu Thr Asn Asp Val Pro Ala Val Thr Ser Gly
 65                  70                  75                  80

Thr Val Ile Glu Ala Asn Asp Tyr Gly Asn Phe Gly Gly Thr Phe Val
                     85                  90                  95

Ile Arg Asp Ala Asn Asp Asn Asp Trp Ile Tyr Gly His Leu Gln Arg
                    100                 105                 110

Gly Ser Met Arg Phe Val Val Gly Asp Lys Val Asn Gln Gly Asp Ile
                115                 120                 125

Ile Gly Leu Gln Gly Asn Ser Asn Tyr Tyr Asp Asn Pro Met Ser Val
                130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
                180                 185                 190

Lys His Ile Tyr Ser Asn His Ile Lys Gly Asn Lys Ile Thr Ala Pro
            195                 200                 205

Lys Pro Ser Ile Gln Gly Glu Leu Gly Gly Lys Leu Glu Val Ser Lys
210                 215                 220

Ala Ala Thr Ile Lys Gln Ser Asp Val Lys Gln Glu Val Lys Lys Gln
225                 230                 235                 240

Glu Ala Lys Gln Ile Val Lys Ala Thr Asp Trp Lys Gln Asn Lys Asp
                245                 250                 255

Gly Ile Trp Tyr Lys Ala Glu His Ala Ser Phe Thr Val Thr Ala Pro
                260                 265                 270

Glu Gly Ile Ile Thr Arg Tyr Lys Gly Pro Trp Thr Gly His Pro Gln
                275                 280                 285

Ala Gly Val Leu Gln Lys Gly Gln Thr Ile Lys Tyr Asp Glu Val Gln
                290                 295                 300

Lys Phe Asp Gly His Val Trp Val Ser Trp Glu Thr Phe Glu Gly Glu
305                 310                 315                 320

Thr Val Tyr Met Pro Val Arg Thr Trp Asp Ala Lys Thr Gly Lys Val
                325                 330                 335

Gly Lys Leu Trp Gly Glu Ile Lys
                340

<210> SEQ ID NO 24
<211> LENGTH: 986
<212> TYPE: PRT
<213> ORGANISM: artificial
<220> FEATURE:
<223> OTHER INFORMATION: His-tagged Ply2638_Ply2638

<400> SEQUENCE: 24

Met Arg Gly Ser His His His His His His Gly Ser Met Leu Thr Ala
  1               5                  10                  15

Ile Asp Tyr Leu Thr Lys Lys Gly Trp Lys Ile Ser Ser Asp Pro Arg
                 20                  25                  30

Thr Tyr Asp Gly Tyr Pro Lys Asn Tyr Gly Tyr Arg Asn Tyr His Glu
             35                  40                  45

Asn Gly Ile Asn Tyr Asp Glu Phe Cys Gly Gly Tyr His Arg Ala Phe
         50                  55                  60

Asp Val Tyr Ser Asn Glu Thr Asn Asp Val Pro Ala Val Thr Ser Gly
```

```
                65                  70                  75                  80
        Thr Val Ile Glu Ala Asn Asp Tyr Gly Asn Phe Gly Gly Thr Phe Val
                            85                  90                  95
        Ile Arg Asp Ala Asn Asp Asn Asp Trp Ile Tyr Gly His Leu Gln Arg
                           100                 105                 110
        Gly Ser Met Arg Phe Val Val Gly Asp Lys Val Asn Gln Gly Asp Ile
                           115                 120                 125
        Ile Gly Leu Gln Gly Asn Ser Asn Tyr Tyr Asp Asn Pro Met Ser Val
                130                 135                 140
        His Leu His Leu Gln Leu Arg Pro Lys Asp Ala Lys Lys Asp Glu Lys
        145                 150                 155                 160
        Ser Gln Val Cys Ser Gly Leu Ala Met Glu Lys Tyr Asp Ile Thr Asn
                            165                 170                 175
        Leu Asn Ala Lys Gln Asp Lys Ser Lys Asn Gly Ser Val Lys Glu Leu
                        180                 185                 190
        Lys His Ile Tyr Ser Asn His Ile Lys Gly Asn Lys Ile Thr Ala Pro
                    195                 200                 205
        Lys Pro Ser Ile Gln Gly Val Val Ile His Asn Asp Tyr Gly Ser Met
        210                 215                 220
        Thr Pro Ser Gln Tyr Leu Pro Trp Leu Tyr Ala Arg Glu Asn Asn Gly
        225                 230                 235                 240
        Thr His Val Asn Gly Trp Ala Ser Val Tyr Ala Asn Arg Asn Glu Val
                            245                 250                 255
        Leu Trp Tyr His Pro Thr Asp Tyr Val Glu Trp His Cys Gly Asn Gln
                        260                 265                 270
        Trp Ala Asn Ala Asn Leu Ile Gly Phe Glu Val Cys Glu Ser Tyr Pro
                    275                 280                 285
        Gly Arg Ile Ser Asp Lys Leu Phe Leu Glu Asn Glu Glu Ala Thr Leu
                290                 295                 300
        Lys Val Ala Ala Asp Val Met Lys Ser Tyr Gly Leu Pro Val Asn Arg
        305                 310                 315                 320
        Asn Thr Val Arg Leu His Asn Glu Phe Phe Gly Thr Ser Cys Pro His
                            325                 330                 335
        Arg Ser Trp Asp Leu His Val Gly Lys Gly Glu Pro Tyr Thr Thr Thr
                        340                 345                 350
        Asn Ile Asn Lys Met Lys Asp Tyr Phe Ile Lys Arg Ile Lys His Tyr
                    355                 360                 365
        Tyr Asp Gly Gly Lys Leu Glu Val Ser Lys Ala Ala Thr Ile Lys Gln
        370                 375                 380
        Ser Asp Val Lys Gln Glu Val Lys Lys Gln Glu Ala Lys Gln Ile Val
        385                 390                 395                 400
        Lys Ala Thr Asp Trp Lys Gln Asn Lys Asp Gly Ile Trp Tyr Lys Ala
                            405                 410                 415
        Glu His Ala Ser Phe Thr Val Thr Ala Pro Glu Gly Ile Ile Thr Arg
                        420                 425                 430
        Tyr Lys Gly Pro Trp Thr Gly His Pro Gln Ala Gly Val Leu Gln Lys
                    435                 440                 445
        Gly Gln Thr Ile Lys Tyr Asp Glu Val Gln Lys Phe Asp Gly His Val
                450                 455                 460
        Trp Val Ser Trp Glu Thr Phe Glu Gly Glu Thr Val Tyr Met Pro Val
        465                 470                 475                 480
        Arg Thr Trp Asp Ala Lys Thr Gly Lys Val Gly Lys Leu Trp Gly Glu
                            485                 490                 495
```

-continued

Ile Lys Glu Leu Met Leu Thr Ala Ile Asp Tyr Leu Thr Lys Lys Gly
            500                 505                 510

Trp Lys Ile Ser Ser Asp Pro Arg Thr Tyr Asp Gly Tyr Pro Lys Asn
            515                 520                 525

Tyr Gly Tyr Arg Asn Tyr His Glu Asn Gly Ile Asn Tyr Asp Glu Phe
            530                 535                 540

Cys Gly Gly Tyr His Arg Ala Phe Asp Val Tyr Ser Asn Glu Thr Asn
545                 550                 555                 560

Asp Val Pro Ala Val Thr Ser Gly Thr Val Ile Glu Ala Asn Asp Tyr
                565                 570                 575

Gly Asn Phe Gly Gly Thr Phe Val Ile Arg Asp Ala Asn Asp Asn
            580                 585                 590

Trp Ile Tyr Gly His Leu Gln Arg Gly Ser Met Arg Phe Val Val Gly
            595                 600                 605

Asp Lys Val Asn Gln Gly Asp Ile Ile Gly Leu Gln Gly Asn Ser Asn
            610                 615                 620

Tyr Tyr Asp Asn Pro Met Ser Val His Leu His Leu Gln Leu Arg Pro
625                 630                 635                 640

Lys Asp Ala Lys Lys Asp Glu Lys Ser Gln Val Cys Ser Gly Leu Ala
                645                 650                 655

Met Glu Lys Tyr Asp Ile Thr Asn Leu Asn Ala Lys Gln Asp Lys Ser
            660                 665                 670

Lys Asn Gly Ser Val Lys Glu Leu Lys His Ile Tyr Ser Asn His Ile
            675                 680                 685

Lys Gly Asn Lys Ile Thr Ala Pro Lys Pro Ser Ile Gln Gly Val Val
            690                 695                 700

Ile His Asn Asp Tyr Gly Ser Met Thr Pro Ser Gln Tyr Leu Pro Trp
705                 710                 715                 720

Leu Tyr Ala Arg Glu Asn Asn Gly Thr His Val Asn Gly Trp Ala Ser
                725                 730                 735

Val Tyr Ala Asn Arg Asn Glu Val Leu Trp Tyr His Pro Thr Asp Tyr
            740                 745                 750

Val Glu Trp His Cys Gly Asn Gln Trp Ala Asn Ala Asn Leu Ile Gly
            755                 760                 765

Phe Glu Val Cys Glu Ser Tyr Pro Gly Arg Ile Ser Asp Lys Leu Phe
770                 775                 780

Leu Glu Asn Glu Glu Ala Thr Leu Lys Val Ala Ala Asp Val Met Lys
785                 790                 795                 800

Ser Tyr Gly Leu Pro Val Asn Arg Asn Thr Val Arg Leu His Asn Glu
                805                 810                 815

Phe Phe Gly Thr Ser Cys Pro His Arg Ser Trp Asp Leu His Val Gly
            820                 825                 830

Lys Gly Glu Pro Tyr Thr Thr Thr Asn Ile Asn Lys Met Lys Asp Tyr
            835                 840                 845

Phe Ile Lys Arg Ile Lys His Tyr Tyr Asp Gly Gly Lys Leu Glu Val
            850                 855                 860

Ser Lys Ala Ala Thr Ile Lys Gln Ser Asp Val Lys Gln Glu Val Lys
865                 870                 875                 880

Lys Gln Glu Ala Lys Gln Ile Val Lys Ala Thr Asp Trp Lys Gln Asn
                885                 890                 895

Lys Asp Gly Ile Trp Tyr Lys Ala Glu His Ala Ser Phe Thr Val Thr
            900                 905                 910

```
Ala Pro Glu Gly Ile Ile Thr Arg Tyr Lys Gly Pro Trp Thr Gly His
            915                 920                 925

Pro Gln Ala Gly Val Leu Gln Lys Gly Gln Thr Ile Lys Tyr Asp Glu
        930                 935                 940

Val Gln Lys Phe Asp Gly His Val Trp Val Ser Trp Glu Thr Phe Glu
945                 950                 955                 960

Gly Glu Thr Val Tyr Met Pro Val Arg Thr Trp Asp Ala Lys Thr Gly
                965                 970                 975

Lys Val Gly Lys Leu Trp Gly Glu Ile Lys
            980                 985

<210> SEQ ID NO 25
<211> LENGTH: 672
<212> TYPE: PRT
<213> ORGANISM: artificial
<220> FEATURE:
<223> OTHER INFORMATION: His-tagged CHAP11_M23-2638_Ami2638_CBD2638

<400> SEQUENCE: 25

Met Arg Gly Ser His His His His His His Gly Ser Met Gln Ala Lys
1               5                   10                  15

Leu Thr Lys Asn Glu Phe Ile Glu Trp Leu Lys Thr Ser Glu Gly Lys
            20                  25                  30

Gln Phe Asn Val Asp Leu Trp Tyr Gly Phe Gln Cys Phe Asp Tyr Ala
        35                  40                  45

Asn Ala Gly Trp Lys Val Leu Phe Gly Leu Leu Leu Lys Gly Leu Gly
    50                  55                  60

Ala Lys Asp Ile Pro Phe Ala Asn Asn Phe Asp Gly Leu Ala Thr Val
65                  70                  75                  80

Tyr Gln Asn Thr Pro Asp Phe Leu Ala Gln Pro Gly Asp Met Val Val
                85                  90                  95

Phe Gly Ser Asn Tyr Gly Ala Gly Tyr Gly His Val Ala Trp Val Ile
            100                 105                 110

Glu Ala Thr Leu Asp Tyr Ile Ile Val Tyr Glu Gln Asn Trp Leu Gly
        115                 120                 125

Gly Gly Trp Thr Asp Gly Ile Glu Gln Pro Gly Trp Gly Trp Glu Lys
    130                 135                 140

Val Thr Arg Arg Gln His Ala Tyr Asp Phe Pro Met Trp Phe Ile Arg
145                 150                 155                 160

Pro Asn Phe Lys Ser Glu Thr Ala Pro Arg Ser Val Gln Ser Pro Thr
                165                 170                 175

Gln Ala Pro Lys Lys Glu Thr Ala Gly Ser Met Leu Thr Ala Ile Asp
            180                 185                 190

Tyr Leu Thr Lys Lys Gly Trp Lys Ile Ser Ser Asp Pro Arg Thr Tyr
        195                 200                 205

Asp Gly Tyr Pro Lys Asn Tyr Gly Tyr Arg Asn Tyr His Glu Asn Gly
    210                 215                 220

Ile Asn Tyr Asp Glu Phe Cys Gly Gly Tyr His Arg Ala Phe Asp Val
225                 230                 235                 240

Tyr Ser Asn Glu Thr Asn Asp Val Pro Ala Val Thr Ser Gly Thr Val
                245                 250                 255

Ile Glu Ala Asn Asp Tyr Gly Asn Phe Gly Gly Thr Phe Val Ile Arg
            260                 265                 270

Asp Ala Asn Asp Asn Asp Trp Ile Tyr Gly His Leu Gln Arg Gly Ser
        275                 280                 285
```

Met Arg Phe Val Val Gly Asp Lys Val Asn Gln Gly Asp Ile Ile Gly
290                 295                 300

Leu Gln Gly Asn Ser Asn Tyr Tyr Asp Asn Pro Met Ser Val His Leu
305                 310                 315                 320

His Leu Gln Leu Arg Pro Lys Asp Ala Lys Asp Glu Lys Ser Gln
            325                 330                 335

Val Cys Ser Gly Leu Ala Met Glu Lys Tyr Asp Ile Thr Asn Leu Asn
                340                 345                 350

Ala Lys Gln Asp Lys Ser Lys Asn Gly Ser Val Lys Glu Leu Lys His
            355                 360                 365

Ile Tyr Ser Asn His Ile Lys Gly Asn Lys Ile Thr Ala Pro Lys Pro
370                 375                 380

Ser Ile Gln Gly Val Val Ile His Asn Asp Tyr Gly Ser Met Thr Pro
385                 390                 395                 400

Ser Gln Tyr Leu Pro Trp Leu Tyr Ala Arg Glu Asn Asn Gly Thr His
                405                 410                 415

Val Asn Gly Trp Ala Ser Val Tyr Ala Asn Arg Asn Glu Val Leu Trp
                420                 425                 430

Tyr His Pro Thr Asp Tyr Val Glu Trp His Cys Gly Asn Gln Trp Ala
            435                 440                 445

Asn Ala Asn Leu Ile Gly Phe Glu Val Cys Glu Ser Tyr Pro Gly Arg
450                 455                 460

Ile Ser Asp Lys Leu Phe Leu Glu Asn Glu Ala Thr Leu Lys Val
465                 470                 475                 480

Ala Ala Asp Val Met Lys Ser Tyr Gly Leu Pro Val Asn Arg Asn Thr
                485                 490                 495

Val Arg Leu His Asn Glu Phe Phe Gly Thr Ser Cys Pro His Arg Ser
            500                 505                 510

Trp Asp Leu His Val Gly Lys Gly Glu Pro Tyr Thr Thr Asn Ile
            515                 520                 525

Asn Lys Met Lys Asp Tyr Phe Ile Lys Arg Ile Lys His Tyr Tyr Asp
530                 535                 540

Gly Gly Lys Leu Glu Val Ser Lys Ala Ala Thr Ile Lys Gln Ser Asp
545                 550                 555                 560

Val Lys Gln Glu Val Lys Gln Glu Ala Lys Gln Ile Val Lys Ala
            565                 570                 575

Thr Asp Trp Lys Gln Asn Lys Asp Gly Ile Trp Tyr Lys Ala Glu His
            580                 585                 590

Ala Ser Phe Thr Val Thr Ala Pro Glu Gly Ile Ile Thr Arg Tyr Lys
            595                 600                 605

Gly Pro Trp Thr Gly His Pro Gln Ala Gly Val Leu Gln Lys Gly Gln
610                 615                 620

Thr Ile Lys Tyr Asp Glu Val Gln Lys Phe Asp Gly His Val Trp Val
625                 630                 635                 640

Ser Trp Glu Thr Phe Glu Gly Thr Val Tyr Met Pro Val Arg Thr
            645                 650                 655

Trp Asp Ala Lys Thr Gly Lys Val Gly Lys Leu Trp Gly Glu Ile Lys
            660                 665                 670

<210> SEQ ID NO 26
<211> LENGTH: 714
<212> TYPE: PRT
<213> ORGANISM: artificial
<220> FEATURE:
<223> OTHER INFORMATION: His-tagged Ami11_M23-2638_Ami2638_CBD2638

<400> SEQUENCE: 26

```
Met Arg Gly Ser His His His His His Gly Ser Lys Pro Gln Pro
1               5                   10                  15

Lys Ala Val Glu Leu Lys Ile Ile Lys Asp Val Val Lys Gly Tyr Asp
            20                  25                  30

Leu Pro Lys Arg Gly Ser Asn Pro Lys Gly Ile Val Ile His Asn Asp
        35                  40                  45

Ala Gly Ser Lys Gly Ala Thr Ala Glu Ala Tyr Arg Asn Gly Leu Val
    50                  55                  60

Asn Ala Pro Leu Ser Arg Leu Glu Ala Gly Ile Ala His Ser Tyr Val
65                  70                  75                  80

Ser Gly Asn Thr Val Trp Gln Ala Leu Asp Glu Ser Gln Val Gly Trp
                85                  90                  95

His Thr Ala Asn Gln Ile Gly Asn Lys Tyr Tyr Gly Ile Glu Val
                100                 105                 110

Cys Gln Ser Met Gly Ala Asp Asn Ala Thr Phe Leu Lys Asn Glu Gln
            115                 120                 125

Ala Thr Phe Gln Glu Cys Ala Arg Leu Leu Lys Lys Trp Gly Leu Pro
        130                 135                 140

Ala Asn Arg Asn Thr Ile Arg Leu His Asn Glu Phe Thr Ser Thr Ser
145                 150                 155                 160

Cys Pro His Arg Ser Ser Val Leu His Thr Gly Phe Asp Pro Val Thr
                165                 170                 175

Arg Gly Leu Leu Pro Glu Asp Lys Arg Leu Gln Leu Lys Asp Tyr Phe
            180                 185                 190

Ile Lys Gln Ile Arg Ala Tyr Met Asp Gly Lys Ile Pro Val Ala Thr
        195                 200                 205

Val Ser Asn Glu Ser Ser Ala Ser Ser Asn Thr Val Lys Pro Val Ala
210                 215                 220

Ser Ala Gly Ser Met Leu Thr Ala Ile Asp Tyr Leu Thr Lys Lys Gly
225                 230                 235                 240

Trp Lys Ile Ser Ser Asp Pro Arg Thr Tyr Asp Gly Tyr Pro Lys Asn
                245                 250                 255

Tyr Gly Tyr Arg Asn Tyr His Glu Asn Gly Ile Asn Tyr Asp Glu Phe
            260                 265                 270

Cys Gly Gly Tyr His Arg Ala Phe Asp Val Tyr Ser Asn Glu Thr Asn
        275                 280                 285

Asp Val Pro Ala Val Thr Ser Gly Thr Val Ile Glu Ala Asn Asp Tyr
290                 295                 300

Gly Asn Phe Gly Gly Thr Phe Val Ile Arg Asp Ala Asn Asp Asn Asp
305                 310                 315                 320

Trp Ile Tyr Gly His Leu Gln Arg Gly Ser Met Arg Phe Val Val Gly
                325                 330                 335

Asp Lys Val Asn Gln Gly Asp Ile Ile Gly Leu Gln Gly Asn Ser Asn
            340                 345                 350

Tyr Tyr Asp Asn Pro Met Ser Val His Leu His Leu Gln Leu Arg Pro
        355                 360                 365

Lys Asp Ala Lys Lys Asp Glu Lys Ser Gln Val Cys Ser Gly Leu Ala
370                 375                 380

Met Glu Lys Tyr Asp Ile Thr Asn Leu Asn Ala Lys Gln Asp Lys Ser
385                 390                 395                 400

Lys Asn Gly Ser Val Lys Glu Leu Lys His Ile Tyr Ser Asn His Ile
```

```
            405                 410                 415
Lys Gly Asn Lys Ile Thr Ala Pro Lys Pro Ser Ile Gln Gly Val Val
            420                 425                 430

Ile His Asn Asp Tyr Gly Ser Met Thr Pro Ser Gln Tyr Leu Pro Trp
            435                 440                 445

Leu Tyr Ala Arg Glu Asn Asn Gly Thr His Val Asn Gly Trp Ala Ser
            450                 455                 460

Val Tyr Ala Asn Arg Asn Glu Val Leu Trp Tyr His Pro Thr Asp Tyr
465                 470                 475                 480

Val Glu Trp His Cys Gly Asn Gln Trp Ala Asn Ala Asn Leu Ile Gly
                485                 490                 495

Phe Glu Val Cys Glu Ser Tyr Pro Gly Arg Ile Ser Asp Lys Leu Phe
                500                 505                 510

Leu Glu Asn Glu Glu Ala Thr Leu Lys Val Ala Ala Asp Val Met Lys
                515                 520                 525

Ser Tyr Gly Leu Pro Val Asn Arg Asn Thr Val Arg Leu His Asn Glu
            530                 535                 540

Phe Phe Gly Thr Ser Cys Pro His Arg Ser Trp Asp Leu His Val Gly
545                 550                 555                 560

Lys Gly Glu Pro Tyr Thr Thr Thr Asn Ile Asn Lys Met Lys Asp Tyr
                565                 570                 575

Phe Ile Lys Arg Ile Lys His Tyr Tyr Asp Gly Gly Lys Leu Glu Val
                580                 585                 590

Ser Lys Ala Ala Thr Ile Lys Gln Ser Asp Val Lys Gln Glu Val Lys
                595                 600                 605

Lys Gln Glu Ala Lys Gln Ile Val Lys Ala Thr Asp Trp Lys Gln Asn
            610                 615                 620

Lys Asp Gly Ile Trp Tyr Lys Ala Glu His Ala Ser Phe Thr Val Thr
625                 630                 635                 640

Ala Pro Glu Gly Ile Ile Thr Arg Tyr Lys Gly Pro Trp Thr His Ala
                645                 650                 655

Pro Gln Ala Gly Val Leu Gln Lys Gly Gln Thr Ile Lys Tyr Asp Glu
                660                 665                 670

Val Gln Lys Phe Asp Gly His Val Trp Val Ser Trp Glu Thr Phe Glu
            675                 680                 685

Gly Glu Thr Val Tyr Met Pro Val Arg Thr Trp Asp Ala Lys Thr Gly
            690                 695                 700

Lys Val Gly Lys Leu Trp Gly Glu Ile Lys
705                 710

<210> SEQ ID NO 27
<211> LENGTH: 652
<212> TYPE: PRT
<213> ORGANISM: artificial
<220> FEATURE:
<223> OTHER INFORMATION: His-tagged CHAPTw_Ami2638_M23-LST_CBD2638

<400> SEQUENCE: 27

Met Arg Gly Ser His His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
        35                  40                  45

Ile Tyr His Val Thr Asp Gly Lys Ile Arg Met Trp Gly Asn Ala Lys
```

```
                50                  55                  60
Asp Ala Ile Asn Asn Ser Phe Gly Gly Thr Ala Thr Val Tyr Lys Asn
 65                  70                  75                  80

Tyr Pro Ala Phe Arg Pro Lys Tyr Gly Asp Val Val Trp Thr Thr
                 85                  90                  95

Gly Asn Phe Ala Thr Tyr Gly His Ile Ala Ile Val Thr Asn Pro Asp
                100                 105                 110

Pro Tyr Gly Asp Leu Gln Tyr Val Thr Val Leu Glu Gln Asn Trp Asn
                115                 120                 125

Gly Asn Gly Ile Tyr Lys Thr Glu Leu Ala Thr Ile Arg Thr His Asp
130                 135                 140

Tyr Thr Gly Ile Thr His Phe Ile Lys Asp Ala Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
                180                 185                 190

Lys His Ile Tyr Ser Asn His Ile Lys Gly Asn Lys Ile Thr Ala Pro
                195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
                260                 265                 270

Trp Ala Asn Ala Asn Leu Ile Gly Phe Glu Val Cys Glu Ser Tyr Pro
                275                 280                 285

Gly Arg Ile Ser Asp Lys Leu Phe Leu Glu Asn Glu Glu Ala Thr Leu
                290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
                340                 345                 350

Asn Ile Asn Lys Met Lys Asp Tyr Phe Ile Lys Arg Ile Lys His Tyr
                355                 360                 365

Tyr Asp Gly Gly Lys Leu Glu Val Ser Lys Ala Thr Ile Lys Gln
                370                 375                 380

Ser Asp Val Lys Gln Glu Val Lys Gln Ala Lys Gln Ile Val
385                 390                 395                 400

Lys Ala Thr Asp Ala Ala Thr His Glu His Ser Ala Gln Trp Leu Asn
                405                 410                 415

Asn Tyr Lys Lys Gly Tyr Gly Tyr Gly Pro Tyr Pro Leu Gly Ile Asn
                420                 425                 430

Gly Gly Met His Tyr Gly Val Asp Phe Phe Met Asn Ile Gly Thr Pro
                435                 440                 445

Val Lys Ala Ile Ser Ser Gly Lys Ile Val Glu Ala Gly Trp Ser Asn
                450                 455                 460

Tyr Gly Gly Gly Asn Gln Ile Gly Leu Ile Glu Asn Asp Gly Val His
465                 470                 475                 480
```

```
Arg Gln Trp Tyr Met His Leu Ser Lys Tyr Asn Val Lys Val Gly Asp
                485                 490                 495

Tyr Val Lys Ala Gly Gln Ile Ile Gly Trp Ser Gly Ser Thr Gly Tyr
            500                 505                 510

Ser Thr Ala Pro His Leu His Phe Gln Arg Met Val Asn Ser Phe Ser
        515                 520                 525

Asn Ser Thr Ala Gln Asp Pro Met Pro Phe Leu Lys Ser Ala Gly Tyr
    530                 535                 540

Gly Lys Ala Gly Gly Thr Val Thr Pro Thr Pro Asn Thr Gly Trp Lys
545                 550                 555                 560

Gln Asn Lys Asp Gly Ile Trp Tyr Lys Ala Glu His Ala Ser Phe Thr
                565                 570                 575

Val Thr Ala Pro Glu Gly Ile Ile Thr Arg Tyr Lys Gly Pro Trp Thr
            580                 585                 590

Gly His Pro Gln Ala Gly Val Leu Gln Lys Gly Gln Thr Ile Lys Tyr
        595                 600                 605

Asp Glu Val Gln Lys Phe Asp Gly His Val Trp Val Ser Trp Glu Thr
    610                 615                 620

Phe Glu Gly Glu Thr Val Tyr Met Pro Val Arg Thr Trp Asp Ala Lys
625                 630                 635                 640

Thr Gly Lys Val Gly Lys Leu Trp Gly Glu Ile Lys
                645                 650

<210> SEQ ID NO 28
<211> LENGTH: 650
<212> TYPE: PRT
<213> ORGANISM: artificial
<220> FEATURE:
<223> OTHER INFORMATION: His-tagged CHAPTw_Ami2638_M23-LST_CWT-LST

<400> SEQUENCE: 28

Met Arg Gly Ser His His His His His Gly Ser Met Lys Thr Leu
1               5                   10                  15

Lys Gln Ala Glu Ser Tyr Ile Lys Ser Lys Val Asn Thr Gly Thr Asp
            20                  25                  30

Phe Asp Gly Leu Tyr Gly Tyr Gln Cys Met Asp Leu Ala Val Asp Tyr
        35                  40                  45

Ile Tyr His Val Thr Asp Gly Lys Ile Arg Met Trp Gly Asn Ala Lys
    50                  55                  60

Asp Ala Ile Asn Asn Ser Phe Gly Gly Thr Ala Thr Val Tyr Lys Asn
65                  70                  75                  80

Tyr Pro Ala Phe Arg Pro Lys Tyr Gly Asp Val Val Trp Thr Thr
                85                  90                  95

Gly Asn Phe Ala Thr Tyr Gly His Ile Ala Ile Val Thr Asn Pro Asp
            100                 105                 110

Pro Tyr Gly Asp Leu Gln Tyr Val Thr Val Leu Glu Gln Asn Trp Asn
        115                 120                 125

Gly Asn Gly Ile Tyr Lys Thr Glu Leu Ala Thr Ile Arg Thr His Asp
    130                 135                 140

Tyr Thr Gly Ile Thr His Phe Ile Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190
```

-continued

Lys His Ile Tyr Ser Asn His Ile Lys Gly Asn Lys Ile Thr Ala Pro
            195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
            245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
            275                 280                 285

Gly Arg Ile Ser Asp Lys Leu Phe Leu Glu Asn Glu Glu Ala Thr Leu
            290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
            325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
            355                 360                 365

Tyr Asp Gly Gly Lys Leu Glu Val Ser Lys Ala Ala Thr Ile Lys Gln
            370                 375                 380

Ser Asp Val Lys Gln Glu Val Lys Gln Glu Ala Lys Gln Ile Val
385                 390                 395                 400

Lys Ala Thr Asp Ala Ala Thr His Glu His Ser Ala Gln Trp Leu Asn
            405                 410                 415

Asn Tyr Lys Lys Gly Tyr Gly Tyr Gly Pro Tyr Pro Leu Gly Ile Asn
            420                 425                 430

Gly Gly Met His Tyr Gly Val Asp Phe Phe Met Asn Ile Gly Thr Pro
            435                 440                 445

Val Lys Ala Ile Ser Ser Gly Lys Ile Val Glu Ala Gly Trp Ser Asn
            450                 455                 460

Tyr Gly Gly Asn Gln Ile Gly Leu Ile Glu Asn Asp Gly Val His
465                 470                 475                 480

Arg Gln Trp Tyr Met His Leu Ser Lys Tyr Asn Val Lys Val Gly Asp
            485                 490                 495

Tyr Val Lys Ala Gly Gln Ile Ile Gly Trp Ser Gly Ser Thr Gly Tyr
            500                 505                 510

Ser Thr Ala Pro His Leu His Phe Gln Arg Met Val Asn Ser Phe Ser
            515                 520                 525

Asn Ser Thr Ala Gln Asp Pro Met Pro Phe Leu Lys Ser Ala Gly Tyr
            530                 535                 540

Gly Lys Ala Gly Gly Thr Val Thr Pro Thr Pro Asn Thr Gly Trp Lys
545                 550                 555                 560

Thr Asn Lys Tyr Gly Thr Leu Tyr Lys Ser Glu Ser Ala Ser Phe Thr
            565                 570                 575

Pro Asn Thr Asp Ile Ile Thr Arg Thr Thr Gly Pro Phe Arg Ser Met
            580                 585                 590

Pro Gln Ser Gly Val Leu Lys Ala Gly Gln Thr Ile His Tyr Asp Glu
            595                 600                 605

```
Val Met Lys Gln Asp Gly His Val Trp Val Gly Tyr Thr Gly Asn Ser
    610                 615                 620
```

```
Gly Gln Arg Ile Tyr Leu Pro Val Arg Thr Trp Asn Lys Ser Thr Asn
625                 630                 635                 640
```

```
Thr Leu Gly Val Leu Trp Gly Thr Ile Lys
                645                 650
```

<210> SEQ ID NO 29
<211> LENGTH: 517
<212> TYPE: PRT
<213> ORGANISM: artificial
<220> FEATURE:
<223> OTHER INFORMATION: His-tagged M23-LST_Ami2638_CBD2638

<400> SEQUENCE: 29

```
Met Arg Gly Ser His His His His His Gly Ser Ala Ala Thr His
1               5                   10                  15
```

```
Glu His Ser Ala Gln Trp Leu Asn Asn Tyr Lys Lys Gly Tyr Gly Tyr
                20                  25                  30
```

```
Gly Pro Tyr Pro Leu Gly Ile Asn Gly Gly Met His Tyr Gly Val Asp
            35                  40                  45
```

```
Phe Phe Met Asn Ile Gly Thr Pro Val Lys Ala Ile Ser Ser Gly Lys
50                  55                  60
```

```
Ile Val Glu Ala Gly Trp Ser Asn Tyr Gly Gly Asn Gln Ile Gly
65                  70                  75                  80
```

```
Leu Ile Glu Asn Asp Gly Val His Arg Gln Trp Tyr Met His Leu Ser
                85                  90                  95
```

```
Lys Tyr Asn Val Lys Val Gly Asp Tyr Val Lys Ala Gly Gln Ile Ile
                100                 105                 110
```

```
Gly Trp Ser Gly Ser Thr Gly Tyr Ser Thr Ala Pro His Leu His Phe
            115                 120                 125
```

```
Gln Arg Met Val Asn Ser Phe Ser Asn Ser Thr Ala Gln Asp Pro Met
130                 135                 140
```

```
Pro Phe Leu Lys Ser Ala Gly Tyr Gly Lys Ala Gly Gly Thr Val Thr
145                 150                 155                 160
```

```
Pro Thr Pro Asn Thr Gly Glu Leu Leu Arg Pro Lys Asp Ala Lys Lys
                165                 170                 175
```

```
Asp Glu Lys Ser Gln Val Cys Ser Gly Leu Ala Met Glu Lys Tyr Asp
                180                 185                 190
```

```
Ile Thr Asn Leu Asn Ala Lys Gln Asp Lys Ser Lys Asn Gly Ser Val
            195                 200                 205
```

```
Lys Glu Leu Lys His Ile Tyr Ser Asn His Ile Lys Gly Asn Lys Ile
210                 215                 220
```

```
Thr Ala Pro Lys Pro Ser Ile Gln Gly Val Val Ile His Asn Asp Tyr
225                 230                 235                 240
```

```
Gly Ser Met Thr Pro Ser Gln Tyr Leu Pro Trp Leu Tyr Ala Arg Glu
                245                 250                 255
```

```
Asn Asn Gly Thr His Val Asn Gly Trp Ala Ser Val Tyr Ala Asn Arg
                260                 265                 270
```

```
Asn Glu Val Leu Trp Tyr His Pro Thr Asp Tyr Val Glu Trp His Cys
            275                 280                 285
```

```
Gly Asn Gln Trp Ala Asn Ala Asn Leu Ile Gly Phe Glu Val Cys Glu
    290                 295                 300
```

```
Ser Tyr Pro Gly Arg Ile Ser Asp Lys Leu Phe Leu Glu Asn Glu Glu
305                 310                 315                 320
```

```
Ala Thr Leu Lys Val Ala Ala Asp Val Met Lys Ser Tyr Gly Leu Pro
            325                 330                 335

Val Asn Arg Asn Thr Val Arg Leu His Asn Glu Phe Phe Gly Thr Ser
        340                 345                 350

Cys Pro His Arg Ser Trp Asp Leu His Val Gly Lys Gly Glu Pro Tyr
            355                 360                 365

Thr Thr Thr Asn Ile Asn Lys Met Lys Asp Tyr Phe Ile Lys Arg Ile
370                 375                 380

Lys His Tyr Tyr Asp Gly Gly Lys Leu Glu Val Ser Lys Ala Ala Thr
385                 390                 395                 400

Ile Lys Gln Ser Asp Val Lys Gln Glu Val Lys Lys Gln Glu Ala Lys
            405                 410                 415

Gln Ile Val Lys Ala Thr Asp Trp Lys Gln Asn Lys Asp Gly Ile Trp
        420                 425                 430

Tyr Lys Ala Glu His Ala Ser Phe Thr Val Thr Ala Pro Glu Gly Ile
            435                 440                 445

Ile Thr Arg Tyr Lys Gly Pro Trp Thr Gly His Pro Gln Ala Gly Val
        450                 455                 460

Leu Gln Lys Gly Gln Thr Ile Lys Tyr Asp Glu Val Gln Lys Phe Asp
465                 470                 475                 480

Gly His Val Trp Val Ser Trp Glu Thr Phe Glu Gly Glu Thr Val Tyr
            485                 490                 495

Met Pro Val Arg Thr Trp Asp Ala Lys Thr Gly Lys Val Gly Lys Leu
        500                 505                 510

Trp Gly Glu Ile Lys
        515

<210> SEQ ID NO 30
<211> LENGTH: 506
<212> TYPE: PRT
<213> ORGANISM: artificial
<220> FEATURE:
<223> OTHER INFORMATION: His-tagged LST_LST

<400> SEQUENCE: 30

Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr
            20                  25                  30

Gly Pro Tyr Pro Leu Gly Ile Asn Gly Met His Tyr Gly Val Asp
        35                  40                  45

Phe Phe Met Asn Ile Gly Thr Pro Val Lys Ala Ile Ser Ser Gly Lys
50                  55                  60

Ile Val Glu Ala Gly Trp Ser Asn Tyr Gly Gly Asn Gln Ile Gly
65                  70                  75                  80

Leu Ile Glu Asn Asp Gly Val His Arg Gln Trp Tyr Met His Leu Ser
            85                  90                  95

Lys Tyr Asn Val Lys Val Gly Asp Tyr Val Lys Ala Gly Gln Ile Ile
            100                 105                 110

Gly Trp Ser Gly Ser Thr Gly Tyr Ser Thr Ala Pro His Leu His Phe
        115                 120                 125

Gln Arg Met Val Asn Ser Phe Ser Asn Ser Thr Ala Gln Asp Pro Met
130                 135                 140

Pro Phe Leu Lys Ser Ala Gly Tyr Gly Lys Ala Gly Gly Thr Val Thr
145                 150                 155                 160
```

Pro Thr Pro Asn Thr Gly Trp Lys Thr Asn Lys Tyr Gly Thr Leu Tyr
              165                 170                 175

Lys Ser Glu Ser Ala Ser Phe Thr Pro Asn Thr Asp Ile Ile Thr Arg
          180                 185                 190

Thr Thr Gly Pro Phe Arg Ser Met Pro Gln Ser Gly Val Leu Lys Ala
      195                 200                 205

Gly Gln Thr Ile His Tyr Asp Glu Val Met Lys Gln Asp Gly His Val
  210                 215                 220

Trp Val Gly Tyr Thr Asn Ser Gly Gln Arg Ile Tyr Leu Pro Val
225                 230                 235                 240

Arg Thr Trp Asn Lys Ser Thr Asn Thr Leu Gly Val Leu Trp Gly Thr
              245                 250                 255

Ile Lys Glu Leu Ala Ala Thr His Glu His Ser Ala Gln Trp Leu Asn
          260                 265                 270

Asn Tyr Lys Lys Gly Tyr Gly Tyr Gly Pro Tyr Pro Leu Gly Ile Asn
      275                 280                 285

Gly Gly Met His Tyr Gly Val Asp Phe Phe Met Asn Ile Gly Thr Pro
  290                 295                 300

Val Lys Ala Ile Ser Ser Gly Lys Ile Val Glu Ala Gly Trp Ser Asn
305                 310                 315                 320

Tyr Gly Gly Gly Asn Gln Ile Gly Leu Ile Glu Asn Asp Gly Val His
              325                 330                 335

Arg Gln Trp Tyr Met His Leu Ser Lys Tyr Asn Val Lys Val Gly Asp
          340                 345                 350

Tyr Val Lys Ala Gly Gln Ile Ile Gly Trp Ser Gly Ser Thr Gly Tyr
      355                 360                 365

Ser Thr Ala Pro His Leu His Phe Gln Arg Met Val Asn Ser Phe Ser
  370                 375                 380

Asn Ser Thr Ala Gln Asp Pro Met Pro Phe Leu Lys Ser Ala Gly Tyr
385                 390                 395                 400

Gly Lys Ala Gly Gly Thr Val Thr Pro Thr Pro Asn Thr Gly Trp Lys
              405                 410                 415

Thr Asn Lys Tyr Gly Thr Leu Tyr Lys Ser Glu Ser Ala Ser Phe Thr
          420                 425                 430

Pro Asn Thr Asp Ile Ile Thr Arg Thr Thr Gly Pro Phe Arg Ser Met
      435                 440                 445

Pro Gln Ser Gly Val Leu Lys Ala Gly Gln Thr Ile His Tyr Asp Glu
  450                 455                 460

Val Met Lys Gln Asp Gly His Val Trp Val Gly Tyr Thr Gly Asn Ser
465                 470                 475                 480

Gly Gln Arg Ile Tyr Leu Pro Val Arg Thr Trp Asn Lys Ser Thr Asn
              485                 490                 495

Thr Leu Gly Val Leu Trp Gly Thr Ile Lys
          500                 505

<210> SEQ ID NO 31
<211> LENGTH: 414
<212> TYPE: PRT
<213> ORGANISM: artificial
<220> FEATURE:
<223> OTHER INFORMATION: His-tagged M23-LST_M23-LST_CWT-LST

<400> SEQUENCE: 31

Met Arg Gly Ser His His His His His His Gly Ser Ala Ala Thr His
1               5                   10                  15

Glu His Ser Ala Gln Trp Leu Asn Asn Tyr Lys Lys Gly Tyr Gly Tyr
                20                  25                  30

Gly Pro Tyr Pro Leu Gly Ile Asn Gly Gly Met His Tyr Gly Val Asp
            35                  40                  45

Phe Phe Met Asn Ile Gly Thr Pro Val Lys Ala Ile Ser Ser Gly Lys
        50                  55                  60

Ile Val Glu Ala Gly Trp Ser Asn Tyr Gly Gly Asn Gln Ile Gly
65                  70                  75                  80

Leu Ile Glu Asn Asp Gly Val His Arg Gln Trp Tyr Met His Leu Ser
                85                  90                  95

Lys Tyr Asn Val Lys Val Gly Asp Tyr Val Lys Ala Gly Gln Ile Ile
            100                 105                 110

Gly Trp Ser Gly Ser Thr Gly Tyr Ser Thr Ala Pro His Leu His Phe
        115                 120                 125

Gln Arg Met Val Asn Ser Phe Ser Asn Ser Thr Ala Gln Asp Pro Met
    130                 135                 140

Pro Phe Leu Lys Ser Ala Gly Tyr Gly Lys Ala Gly Gly Thr Val Thr
145                 150                 155                 160

Pro Thr Pro Asn Thr Gly Glu Leu Ala Ala Thr His Glu His Ser Ala
                165                 170                 175

Gln Trp Leu Asn Asn Tyr Lys Lys Gly Tyr Gly Tyr Gly Pro Tyr Pro
            180                 185                 190

Leu Gly Ile Asn Gly Gly Met His Tyr Gly Val Asp Phe Phe Met Asn
        195                 200                 205

Ile Gly Thr Pro Val Lys Ala Ile Ser Ser Gly Lys Ile Val Glu Ala
    210                 215                 220

Gly Trp Ser Asn Tyr Gly Gly Asn Gln Ile Gly Leu Ile Glu Asn
225                 230                 235                 240

Asp Gly Val His Arg Gln Trp Tyr Met His Leu Ser Lys Tyr Asn Val
                245                 250                 255

Lys Val Gly Asp Tyr Val Lys Ala Gly Gln Ile Ile Gly Trp Ser Gly
            260                 265                 270

Ser Thr Gly Tyr Ser Thr Ala Pro His Leu His Phe Gln Arg Met Val
        275                 280                 285

Asn Ser Phe Ser Asn Ser Thr Ala Gln Asp Pro Met Pro Phe Leu Lys
    290                 295                 300

Ser Ala Gly Tyr Gly Lys Ala Gly Gly Thr Val Thr Pro Thr Pro Asn
305                 310                 315                 320

Thr Gly Trp Lys Thr Asn Lys Tyr Gly Thr Leu Tyr Lys Ser Glu Ser
                325                 330                 335

Ala Ser Phe Thr Pro Asn Thr Asp Ile Ile Thr Arg Thr Thr Gly Pro
            340                 345                 350

Phe Arg Ser Met Pro Gln Ser Gly Val Leu Lys Ala Gly Gln Thr Ile
        355                 360                 365

His Tyr Asp Glu Val Met Lys Gln Asp Gly His Val Trp Val Gly Tyr
    370                 375                 380

Thr Gly Asn Ser Gly Gln Arg Ile Tyr Leu Pro Val Arg Thr Trp Asn
385                 390                 395                 400

Lys Ser Thr Asn Thr Leu Gly Val Leu Trp Gly Thr Ile Lys
                405                 410

<210> SEQ ID NO 32
<211> LENGTH: 628
<212> TYPE: PRT

<213> ORGANISM: artificial
<220> FEATURE:
<223> OTHER INFORMATION: His-tagged M23-2638_Ami2638_CBD2638_CBD2638

<400> SEQUENCE: 32

Met Arg Gly Ser His His His His His His Gly Ser Met Leu Thr Ala
1               5                   10                  15

Ile Asp Tyr Leu Thr Lys Lys Gly Trp Lys Ile Ser Ser Asp Pro Arg
            20                  25                  30

Thr Tyr Asp Gly Tyr Pro Lys Asn Gly Tyr Arg Asn Tyr His Glu
        35                  40                  45

Asn Gly Ile Asn Tyr Asp Glu Phe Cys Gly Gly Tyr His Arg Ala Phe
50                  55                  60

Asp Val Tyr Ser Asn Glu Thr Asn Asp Val Pro Ala Val Thr Ser Gly
65                  70                  75                  80

Thr Val Ile Glu Ala Asn Asp Tyr Gly Asn Phe Gly Thr Phe Val
                85                  90                  95

Ile Arg Asp Ala Asn Asp Asn Asp Trp Ile Tyr Gly His Leu Gln Arg
            100                 105                 110

Gly Ser Met Arg Phe Val Val Gly Asp Lys Val Asn Gln Gly Asp Ile
        115                 120                 125

Ile Gly Leu Gln Gly Asn Ser Asn Tyr Tyr Asp Asn Pro Met Ser Val
130                 135                 140

His Leu His Leu Gln Leu Arg Pro Lys Asp Ala Lys Lys Asp Glu Lys
145                 150                 155                 160

Ser Gln Val Cys Ser Gly Leu Ala Met Glu Lys Tyr Asp Ile Thr Asn
                165                 170                 175

Leu Asn Ala Lys Gln Asp Lys Ser Lys Asn Gly Ser Val Lys Glu Leu
            180                 185                 190

Lys His Ile Tyr Ser Asn His Ile Lys Gly Asn Lys Ile Thr Ala Pro
        195                 200                 205

Lys Pro Ser Ile Gln Gly Val Val Ile His Asn Asp Tyr Gly Ser Met
210                 215                 220

Thr Pro Ser Gln Tyr Leu Pro Trp Leu Tyr Ala Arg Glu Asn Asn Gly
225                 230                 235                 240

Thr His Val Asn Gly Trp Ala Ser Val Tyr Ala Asn Arg Asn Glu Val
                245                 250                 255

Leu Trp Tyr His Pro Thr Asp Tyr Val Glu Trp His Cys Gly Asn Gln
            260                 265                 270

Trp Ala Asn Ala Asn Leu Ile Gly Phe Glu Val Cys Glu Ser Tyr Pro
        275                 280                 285

Gly Arg Ile Ser Asp Lys Leu Phe Leu Glu Asn Glu Glu Ala Thr Leu
290                 295                 300

Lys Val Ala Ala Asp Val Met Lys Ser Tyr Gly Leu Pro Val Asn Arg
305                 310                 315                 320

Asn Thr Val Arg Leu His Asn Glu Phe Phe Gly Thr Ser Cys Pro His
                325                 330                 335

Arg Ser Trp Asp Leu His Val Gly Lys Gly Glu Pro Tyr Thr Thr Thr
            340                 345                 350

Asn Ile Asn Lys Met Lys Asp Tyr Phe Ile Lys Arg Ile Lys His Tyr
        355                 360                 365

Tyr Asp Gly Gly Lys Leu Glu Val Ser Lys Ala Ala Thr Ile Lys Gln
370                 375                 380

Ser Asp Val Lys Gln Glu Val Lys Lys Gln Glu Ala Lys Gln Ile Val

```
                385                 390                 395                 400
Lys Ala Thr Asp Trp Lys Gln Asn Lys Asp Gly Ile Trp Tyr Lys Ala
                    405                 410                 415
Glu His Ala Ser Phe Thr Val Thr Ala Pro Glu Gly Ile Ile Thr Arg
                420                 425                 430
Tyr Lys Gly Pro Trp Thr Gly His Pro Gln Ala Gly Val Leu Gln Lys
            435                 440                 445
Gly Gln Thr Ile Lys Tyr Asp Glu Val Gln Lys Phe Asp Gly His Val
        450                 455                 460
Trp Val Ser Trp Glu Thr Phe Glu Gly Glu Thr Val Tyr Met Pro Val
465                 470                 475                 480
Arg Thr Trp Asp Ala Lys Thr Gly Lys Val Gly Lys Leu Trp Gly Glu
                485                 490                 495
Ile Lys Glu Leu Gly Gly Lys Leu Glu Val Ser Lys Ala Ala Thr Ile
                500                 505                 510
Lys Gln Ser Asp Val Lys Gln Glu Val Lys Lys Gln Glu Ala Lys Gln
            515                 520                 525
Ile Val Lys Ala Thr Asp Trp Lys Gln Asn Lys Asp Gly Ile Trp Tyr
        530                 535                 540
Lys Ala Glu His Ala Ser Phe Thr Val Thr Ala Pro Glu Gly Ile Ile
545                 550                 555                 560
Thr Arg Tyr Lys Gly Pro Trp Thr Gly His Pro Gln Ala Gly Val Leu
                565                 570                 575
Gln Lys Gly Gln Thr Ile Lys Tyr Asp Glu Val Gln Lys Phe Asp Gly
                580                 585                 590
His Val Trp Val Ser Trp Glu Thr Phe Glu Gly Glu Thr Val Tyr Met
            595                 600                 605
Pro Val Arg Thr Trp Asp Ala Lys Thr Gly Lys Val Gly Lys Leu Trp
        610                 615                 620
Gly Glu Ile Lys
625

<210> SEQ ID NO 33
<211> LENGTH: 741
<212> TYPE: DNA
<213> ORGANISM: Staphylococcus simulans

<400> SEQUENCE: 33
gctgcaacac atgaacattc agcacaatgg ttgaataatt acaaaaaagg atatggttac    60
ggtccttatc cattaggtat aaatggcggt atgcactacg agttgatttt ttttatgaat   120
attggaacac cagtaaaagc tatttcaagc ggaaaaatag ttgaagctgg ttggagtaat   180
tacgaggag gtaatcaaat aggtcttatt gaaaatgatg gagtgcatag acaatggtat   240
atgcatctaa gtaaatataa tgttaaagta ggagattatg tcaaagctgg tcaaataatc   300
ggttggtctg gaagcactgg ttattctaca gcaccacatt tacacttcca agaatggtt   360
aattcatttt caaattcaac tgcccaagat ccaatgcctt tcttaaagag cgcaggatat   420
ggaaaagcag gtggtacagt aactccaacg ccgaatacag gttggaaaac aaacaaatat   480
ggcacactat ataatcaga gtcagctagc ttcacaccta atacagatat aataacaaga   540
acgactggtc catttagaag catgccgcag tcaggagtct aaaagcagg tcaaacaatt   600
cattatgatg aagtgatgaa acaagacggt catgtttggg taggttatac aggtaacagt   660
ggccaacgta tttacttgcc tgtaagaaca tggaataaat ctactaatac tttaggtgtt   720
```
ctttggggaa ctataaagtg a          741

<210> SEQ ID NO 34
<211> LENGTH: 246
<212> TYPE: PRT
<213> ORGANISM: Staphylococcus simulans

<400> SEQUENCE: 34

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
                20                  25                  30

Tyr Gly Val Asp Phe Phe Met Asn Ile Gly Thr Pro Val Lys Ala Ile
            35                  40                  45

Ser Ser Gly Lys Ile Val Glu Ala Gly Trp Ser Asn Tyr Gly Gly Gly
        50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly Trp Lys Thr Asn Lys Tyr
145                 150                 155                 160

Gly Thr Leu Tyr Lys Ser Glu Ser Ala Ser Phe Thr Pro Asn Thr Asp
                165                 170                 175

Ile Ile Thr Arg Thr Thr Gly Pro Phe Arg Ser Met Pro Gln Ser Gly
            180                 185                 190

Val Leu Lys Ala Gly Gln Thr Ile His Tyr Asp Glu Val Met Lys Gln
        195                 200                 205

Asp Gly His Val Trp Val Gly Tyr Thr Gly Asn Ser Gly Gln Arg Ile
    210                 215                 220

Tyr Leu Pro Val Arg Thr Trp Asn Lys Ser Thr Asn Thr Leu Gly Val
225                 230                 235                 240

Leu Trp Gly Thr Ile Lys
                245
```

<210> SEQ ID NO 35
<211> LENGTH: 94
<212> TYPE: PRT
<213> ORGANISM: Staphylococcus aureus bacteriophage 2638a

<400> SEQUENCE: 35

```
Trp Lys Gln Asn Lys Asp Gly Ile Trp Tyr Lys Ala Glu His Ala Ser
1               5                   10                  15

Phe Thr Val Thr Ala Pro Glu Gly Ile Ile Thr Arg Tyr Lys Gly Pro
                20                  25                  30

Trp Thr Gly His Pro Gln Ala Gly Val Leu Gln Lys Gly Gln Thr Ile
            35                  40                  45

Lys Tyr Asp Glu Val Gln Lys Phe Asp Gly His Val Trp Val Ser Trp
        50                  55                  60

Glu Thr Phe Glu Gly Glu Thr Val Tyr Met Pro Val Arg Thr Trp Asp
```

```
                65                  70                  75                  80
Ala Lys Thr Gly Lys Val Gly Lys Leu Trp Gly Glu Ile Lys
                    85                  90

<210> SEQ ID NO 36
<211> LENGTH: 92
<212> TYPE: PRT
<213> ORGANISM: Staphylococcus simulans

<400> SEQUENCE: 36

Trp Lys Thr Asn Lys Tyr Gly Thr Leu Tyr Lys Ser Glu Ser Ala Ser
1               5                   10                  15

Phe Thr Pro Asn Thr Asp Ile Ile Thr Arg Thr Thr Gly Pro Phe Arg
            20                  25                  30

Ser Met Pro Gln Ser Gly Val Leu Lys Ala Gly Gln Thr Ile His Tyr
        35                  40                  45

Asp Glu Val Met Lys Gln Asp Gly His Val Trp Val Gly Tyr Thr Gly
    50                  55                  60

Asn Ser Gly Gln Arg Ile Tyr Leu Pro Val Arg Thr Trp Asn Lys Ser
65                  70                  75                  80

Thr Asn Thr Leu Gly Val Leu Trp Gly Thr Ile Lys
                85                  90

<210> SEQ ID NO 37
<211> LENGTH: 146
<212> TYPE: PRT
<213> ORGANISM: Staphylococcus aureus bacteriophage 2638a

<400> SEQUENCE: 37

Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
        35                  40                  45

His Arg Ala Phe Asp Val Tyr Ser Asn Glu Thr Asn Asp Val Pro Ala
    50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Trp Ile Tyr Gly
                85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
        115                 120                 125

Pro Met Ser Val His Leu His Leu Gln Leu Arg Pro Lys Asp Ala Lys
    130                 135                 140

Lys Asp
145

<210> SEQ ID NO 38
<211> LENGTH: 140
<212> TYPE: PRT
<213> ORGANISM: Staphylococcus simulans

<400> SEQUENCE: 38

Ala Ala Thr His Glu His Ser Ala Gln Trp Leu Asn Asn Tyr Lys Lys
1               5                   10                  15
```

```
Gly Tyr Gly Tyr Gly Pro Tyr Pro Leu Gly Ile Asn Gly Gly Met His
                20                  25                  30

Tyr Gly Val Asp Phe Phe Met Asn Ile Gly Thr Pro Val Lys Ala Ile
            35                  40                  45

Ser Ser Gly Lys Ile Val Glu Ala Gly Trp Ser Asn Tyr Gly Gly Gly
50                  55                  60

Asn Gln Ile Gly Leu Ile Glu Asn Asp Gly Val His Arg Gln Trp Tyr
65                  70                  75                  80

Met His Leu Ser Lys Tyr Asn Val Lys Val Gly Asp Tyr Val Lys Ala
                85                  90                  95

Gly Gln Ile Ile Gly Trp Ser Gly Ser Thr Gly Tyr Ser Thr Ala Pro
            100                 105                 110

His Leu His Phe Gln Arg Met Val Asn Ser Phe Ser Asn Ser Thr Ala
        115                 120                 125

Gln Asp Pro Met Pro Phe Leu Lys Ser Ala Gly Tyr
130                 135                 140

<210> SEQ ID NO 39
<211> LENGTH: 169
<212> TYPE: PRT
<213> ORGANISM: Staphylococcus aureus bacteriophage 2638a

<400> SEQUENCE: 39

Asn Lys Ile Thr Ala Pro Lys Pro Ser Ile Gln Gly Val Val Ile His
1               5                   10                  15

Asn Asp Tyr Gly Ser Met Thr Pro Ser Gln Tyr Leu Pro Trp Leu Tyr
                20                  25                  30

Ala Arg Glu Asn Asn Gly Thr His Val Asn Gly Trp Ala Ser Val Tyr
            35                  40                  45

Ala Asn Arg Asn Glu Val Leu Trp Tyr His Pro Thr Asp Tyr Val Glu
50                  55                  60

Trp His Cys Gly Asn Gln Trp Ala Asn Ala Asn Leu Ile Gly Phe Glu
65                  70                  75                  80

Val Cys Glu Ser Tyr Pro Gly Arg Ile Ser Asp Lys Leu Phe Leu Glu
                85                  90                  95

Asn Glu Glu Ala Thr Leu Lys Val Ala Ala Asp Val Met Lys Ser Tyr
            100                 105                 110

Gly Leu Pro Val Asn Arg Asn Thr Val Arg Leu His Asn Glu Phe Phe
        115                 120                 125

Gly Thr Ser Cys Pro His Arg Ser Trp Asp Leu His Val Gly Lys Gly
    130                 135                 140

Glu Pro Tyr Thr Thr Thr Asn Ile Asn Lys Met Lys Asp Tyr Phe Ile
145                 150                 155                 160

Lys Arg Ile Lys His Tyr Tyr Asp Gly
                165

<210> SEQ ID NO 40
<211> LENGTH: 163
<212> TYPE: PRT
<213> ORGANISM: Staphylococcus aureus phage phi 11

<400> SEQUENCE: 40

Asn Pro Lys Gly Ile Val Ile His Asn Asp Ala Gly Ser Lys Gly Ala
1               5                   10                  15

Thr Ala Glu Ala Tyr Arg Asn Gly Leu Val Asn Ala Pro Leu Ser Arg
                20                  25                  30
```

```
Leu Glu Ala Gly Ile Ala His Ser Tyr Val Ser Gly Asn Thr Val Trp
        35                  40                  45

Gln Ala Leu Asp Glu Ser Gln Val Gly Trp His Thr Ala Asn Gln Ile
 50                  55                  60

Gly Asn Lys Tyr Tyr Gly Ile Glu Val Cys Gln Ser Met Gly Ala
 65                  70                  75                  80

Asp Asn Ala Thr Phe Leu Lys Asn Glu Gln Ala Thr Phe Gln Glu Cys
                85                  90                  95

Ala Arg Leu Leu Lys Lys Trp Gly Leu Pro Ala Asn Arg Asn Thr Ile
                100                 105                 110

Arg Leu His Asn Glu Phe Thr Ser Thr Ser Cys Pro His Arg Ser Ser
                115                 120                 125

Val Leu His Thr Gly Phe Asp Pro Val Thr Arg Gly Leu Leu Pro Glu
                130                 135                 140

Asp Lys Arg Leu Gln Leu Lys Asp Tyr Phe Ile Lys Gln Ile Arg Ala
145                 150                 155                 160

Tyr Met Asp

<210> SEQ ID NO 41
<211> LENGTH: 158
<212> TYPE: PRT
<213> ORGANISM: Staphylococcus aureus phage phi 11

<400> SEQUENCE: 41

Met Ser Ile Ile Met Glu Val Ala Thr Met Gln Ala Lys Leu Thr Lys
  1               5                  10                  15

Asn Glu Phe Ile Glu Trp Leu Lys Thr Ser Glu Gly Lys Gln Phe Asn
                 20                  25                  30

Val Asp Leu Trp Tyr Gly Phe Gln Cys Phe Asp Tyr Ala Asn Ala Gly
                 35                  40                  45

Trp Lys Val Leu Phe Gly Leu Leu Leu Lys Gly Leu Gly Ala Lys Asp
 50                  55                  60

Ile Pro Phe Ala Asn Asn Phe Asp Gly Leu Ala Thr Val Tyr Gln Asn
 65                  70                  75                  80

Thr Pro Asp Phe Leu Ala Gln Pro Gly Asp Met Val Val Phe Gly Ser
                 85                  90                  95

Asn Tyr Gly Ala Gly Tyr Gly His Val Ala Trp Val Ile Glu Ala Thr
                 100                 105                 110

Leu Asp Tyr Ile Ile Val Tyr Glu Gln Asn Trp Leu Gly Gly Gly Trp
                 115                 120                 125

Thr Asp Gly Ile Glu Gln Pro Gly Trp Gly Trp Glu Lys Val Thr Arg
                 130                 135                 140

Arg Gln His Ala Tyr Asp Phe Pro Met Trp Phe Ile Arg Pro
145                 150                 155

<210> SEQ ID NO 42
<211> LENGTH: 140
<212> TYPE: PRT
<213> ORGANISM: Staphylococcus phage Twort

<400> SEQUENCE: 42

Met Lys Thr Leu Lys Gln Ala Glu Ser Tyr Ile Lys Ser Lys Val Asn
  1               5                  10                  15

Thr Gly Thr Asp Phe Asp Gly Leu Tyr Gly Tyr Gln Cys Met Asp Leu
                 20                  25                  30
```

Ala Val Asp Tyr Ile Tyr His Val Thr Asp Gly Lys Ile Arg Met Trp
         35                  40                  45

Gly Asn Ala Lys Asp Ala Ile Asn Asn Ser Phe Gly Gly Thr Ala Thr
 50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Tyr Gly His Ile Ala Ile Val
             85                  90                  95

Thr Asn Pro Asp Pro Tyr Gly Asp Leu Gln Tyr Val Thr Val Leu Glu
             100                 105                 110

Gln Asn Trp Asn Gly Asn Gly Ile Tyr Lys Thr Glu Leu Ala Thr Ile
             115                 120                 125

Arg Thr His Asp Tyr Thr Gly Ile Thr His Phe Ile
 130                 135                 140

<210> SEQ ID NO 43
<211> LENGTH: 12
<212> TYPE: PRT
<213> ORGANISM: artificial
<220> FEATURE:
<223> OTHER INFORMATION: His-tag

<400> SEQUENCE: 43

Met Arg Gly Ser His His His His His His Gly Ser
1               5                   10

<210> SEQ ID NO 44
<211> LENGTH: 1497
<212> TYPE: DNA
<213> ORGANISM: artificial
<220> FEATURE:
<223> OTHER INFORMATION: His-tagged Ply2638

<400> SEQUENCE: 44
atgagaggat cgcatcacca tcaccatcac ggatccatgc taactgctat tgactatctt      60
acgaaaaaag gttggaaaat atcatctgac cctcgcactt acgatggtta ccctaaaaac     120
tacggctaca gaaattacca tgaaaacggc attaattatg atgagttttg tggtggttat     180
catagagctt ttgatgttta cagtaacgaa actaacgacg tgcctgctgt tactagcgga     240
acagttattg aagcaaacga ttacggtaat tttggtggta cattcgttat tagagacgct     300
aacgataacg attggatata tgggcatcta caacgtggct caatgcgatt tgttgtaggc     360
gacaaagtca atcaaggtga cattattggt ttacaaggta atagcaacta ttacgacaat     420
cctatgagtg tacatttaca tttacaatta cgccctaaag acgcaaagaa agatgaaaaa     480
tcacaagtat gtagtggttt ggctatggaa aaatatgaca ttacaaattt aaatgctaaa     540
caagataaat caaagaatgg gagcgtgaaa gagttgaaac atatctattc aaaccatatt     600
aaaggtaaca agattacagc accaaaacct agtattcaag gtgtggtcat ccacaatgat     660
tatggtagta tgacacctag tcaatactta ccatggttat atgcacgtga ataacggt      720
acacacgtta acggttgggc tagtgtttat gcaaatagaa acgaagtgct ttggtatcat     780
ccgacagact acgtagagtg gcattgtggt aatcaatggg caaatgctaa cttaatcgga     840
tttgaagtgt gtgagtcgta tcctggtaga atctcggaca attattcctt agaaaatgaa     900
gaagcgacat tgaaagtagc tgcggatgtg atgaagtcgt acggattacc agttaatcgc     960
aacactgtac gtctgcataa cgaattcttc ggaacttctt gtccacatcg ttcgtgggac    1020
ttgcatgttg gcaaaggtga gccttacaca actactaata ttaataaaat gaaagactac    1080

```
ttcatcaaac gcatcaaaca ttattatgac ggtggaaagc tagaagtaag caaagcagca    1140
actatcaaac aatctgacgt taagcaagaa gttaaaaagc aagaagcaaa acaaattgtg    1200
aaagcaacag attggaaaca gaataaagat ggcatttggt ataaagctga acatgcttcg    1260
ttcacagtga cagcaccaga gggaattatc acaagataca aaggtccttg gactggtcac    1320
ccacaagctg gtgtattaca aaaaggtcaa acgattaaat atgatgaggt tcaaaaattt    1380
gacggtcatg tttgggtatc gtgggaaacg tttgagggcg aaactgtata catgccggta    1440
cgcacatggg acgctaaaac tggtaaagtt ggtaagttgt ggggcgaaat taaataa      1497
```

<210> SEQ ID NO 45
<211> LENGTH: 2019
<212> TYPE: DNA
<213> ORGANISM: artificial
<220> FEATURE:
<223> OTHER INFORMATION: His-tagged CHAP11-M23-2638_Ami2638_CBD2638

<400> SEQUENCE: 45

```
atgagaggat cgcatcacca tcaccatcac ggatccatgc aagcaaaatt aactaaaaat     60
gagtttatag agtggttgaa aacttctgag ggaaaacaat tcaatgtgga cttatggtat    120
ggatttcaat gctttgatta tgccaatgct ggttggaaag ttttgtttgg attacttcta    180
aaaggtttag gtgcaaaaga tattccgttc gctaacaact tcgacggatt agctactgta    240
taccaaaata caccggactt cttagcacaa cctggcgaca tggtggtatt cggtagcaac    300
tacggtgctg atatggtcac gttcatggg taattgaag caactttaga ttacatcatt    360
gtatatgagc agaattggct aggcggtggc tggactgacg gaatcgaaca acccggctgg    420
ggttgggaaa aagttacaag acgacaacat gcttatgatt tccctatgtg gtttatccgt    480
ccgaatttta aaagtgagac agcgccacga tcagttcaat ctcctacaca agcacctaaa    540
aaagaaacag ctggatccat gctaactgct attgactatc ttacgaaaaa aggttggaaa    600
atatcatctg accctcgcac ttacgatggt taccctaaaa actacggcta cagaaattac    660
catgaaaacg gcattaatta tgatgagttt tgtggtggtt atcatagagc ttttgatgtt    720
tacagtaacg aaactaacga cgtgcctgct gttactagcg gaacagttat tgaagcaaac    780
gattacggta attttggtgg tacattcgtt attagagacg ctaacgataa cgattggata    840
tatgggcatc tacaacgtgg ctcaatgcga tttgttgtag cgacaaagt caatcaaggt    900 gacattattg gtttacaagg taatagcaac tattacgaca atcctatgag tgtacattta    960
catttacaat tacgccctaa agacgcaaag aaagatgaaa aatcacaagt atgtagtggt   1020
ttggctatgg aaaaatatga cattacaaat ttaaatgcta aacaagataa atcaaagaat   1080
gggagcgtga aagagttgaa acatatctat tcaaaccata ttaaaggtaa caagattaca   1140
gcaccaaaac ctagtattca aggtgtggtc atccacaatg attatggtag tatgacacct   1200
agtcaatact taccatggtt atatgcacgt gagaataacg gtacacacgt taacggttgg   1260
gctagtgttt atgcaaatag aaacgaagtg ctttggtatc atccgacaga ctacgtagag   1320
tggcattgtg gtaatcaatg gcaaatgctt aacttaatcg gatttgaagt gtgtgagtcg   1380
tatcctggta gaatctcgga caaattattc ttagaaaata agaagcgac attgaaagta   1440 gctgcggatg tgatgaagtc gtacggatta ccagttaatc gcaacactgt acgtctgcat   1500
aacgaattct tcggaacttc ttgtccacat cgttcgtggg acttgcatgt tggcaaaggt   1560
gagccttaca caactactaa tattaataaa atgaaagact acttcatcaa acgcatcaaa   1620
```

| | |
|---|---|
| cattattatg acggtggaaa gctagaagta agcaaagcag caactatcaa acaatctgac | 1680 |
| gttaagcaag aagttaaaaa gcaagaagca aaacaaattg tgaaagcaac agattggaaa | 1740 |
| cagaataaag atggcatttg gtataaagct gaacatgctt cgttcacagt gacagcacca | 1800 |
| gagggaatta tcacaagata caaaggtcct tggactggtc acccacaagc tggtgtatta | 1860 |
| caaaaaggtc aaacgattaa atatgatgag gttcaaaaat ttgacggtca tgtttgggta | 1920 |
| tcgtgggaaa cgtttgaggg cgaaactgta tacatgccgg tacgcacatg ggacgctaaa | 1980 |
| actggtaaag ttggtaagtt gtggggcgaa attaaataa | 2019 |

<210> SEQ ID NO 46
<211> LENGTH: 2145
<212> TYPE: DNA
<213> ORGANISM: artificial
<220> FEATURE:
<223> OTHER INFORMATION: His-tagged Ami11_M23-2638_Ami2638_CBD2638

<400> SEQUENCE: 46

| | |
|---|---|
| atgagaggat cgcatcacca tcaccatcac ggatccaagc cacaacctaa agcagtagaa | 60 |
| cttaaaatca tcaaagatgt ggttaaaggt tatgacctac ctaagcgtgg tagtaaccct | 120 |
| aaaggtatag ttatacacaa cgacgcaggg agcaaagggg cgactgctga agcatatcgt | 180 |
| aacggattag taaatgcacc tttatcaaga ttagaagcgg gcattgcgca tagttacgta | 240 |
| tcaggcaaca cagtttggca agccttagat gaatcacaag taggttggca taccgctaat | 300 |
| caaataggta ataaatatta ttacggtatt gaagtatgtc aatcaatggg cgcagataac | 360 |
| gcgacattct aaaaaatga acaggcaact ttccaagaat cgctagatt gttgaaaaaa | 420 |
| tggggattac cagcaaacag aaatacaatc agattgcaca tgaatttac ttcaacatca | 480 |
| tgccctcata gaagttcggt tttacacact ggttttgacc cagtaactcg cggtctattg | 540 |
| ccagaagaca agcggttgca acttaaagac tactttatca agcagattag ggcgtacatg | 600 |
| gatggtaaaa taccggttgc cactgtctct aatgagtcaa gcgcttcaag taatacagtt | 660 |
| aaaccagttg caagtgcagg atccatgcta actgctattg actatcttac gaaaaaaggt | 720 |
| tggaaaatat catctgaccc tcgcacttac gatggttacc ctaaaaacta cggctacaga | 780 |
| aattaccatg aaaacggcat taattatgat gagttttgtg gtggttatca tagagctttt | 840 |
| gatgtttaca gtaacgaaac taacgacgtg cctgctgtta ctagcggaac agttattgaa | 900 |
| gcaaacgatt acggtaattt tggtggtaca ttcgttatta gagacgctaa cgataacgat | 960 |
| tggatatatg gcatctaca acgtggctca atgcgatttg ttgtaggcga caaagtcaat | 1020 |
| caaggtgaca ttattggttt acaaggtaat agcaactatt acgacaatcc tatgagtgta | 1080 |
| catttacatt tacaattacg ccctaaagac gcaaagaaag atgaaaaatc acaagtatgt | 1140 |
| agtggtttgg ctatggaaaa atatgacatt acaaatttaa atgctaaaca agataaatca | 1200 |
| aagaatggga gcgtgaaaga gttgaaacat atctattcaa accatattaa aggtaacaag | 1260 |
| attacagcac caaaacctag tattcaaggt gtggtcatcc acaatgatta tggtagtatg | 1320 |
| acacctagtc aatacttacc atggttatat gcacgtgaga ataacggtac acacgttaac | 1380 |
| ggttgggcta tgtttatgc aaatagaaac gaagtgcttt ggtatcatcc gacagactac | 1440 |
| gtagagtggc attgtggtaa tcaatgggca aatgctaact aatcggatt tgaagtgtgt | 1500 |
| gagtcgtatc ctggtagaat ctcggacaaa ttattcttag aaaatgaaga agcgacattg | 1560 |
| aaagtagctg cggatgtgat gaagtcgtac ggattaccag ttaatcgcaa cactgtacgt | 1620 |
| ctgcataacg aattcttcgg aacttcttgt ccacatcgtt cgtgggactt gcatgttggc | 1680 |

```
aaaggtgagc cttacacaac tactaatatt aataaaatga aagactactt catcaaacgc    1740
atcaaacatt attatgacgg tggaaagcta gaagtaagca aagcagcaac tatcaaacaa    1800
tctgacgtta agcaagaagt taaaaagcaa gaagcaaaac aaattgtgaa agcaacagat    1860
tggaaacaga ataagatgg catttggtat aaagctgaac atgcttcgtt cacagtgaca     1920
gcaccagagg gaattatcac aagatacaaa ggtccttgga ctggtcaccc acaagctggt    1980
gtattacaaa aaggtcaaac gattaaatat gatgaggttc aaaaatttga cggtcatgtt    2040
tgggtatcgt gggaaacgtt tgagggcgaa actgtataca tgccggtacg cacatgggac    2100
gctaaaactg gtaaagttgg taagttgtgg ggcgaaatta aataa                    2145
```

<210> SEQ ID NO 47
<211> LENGTH: 1959
<212> TYPE: DNA
<213> ORGANISM: artificial
<220> FEATURE:
<223> OTHER INFORMATION: His-tagged CHAPTw_Ami2638_M23-LST_CBD2638

<400> SEQUENCE: 47

```
atgagaggat cgcatcacca tcaccatcac ggatccatga aaaccctgaa acaagcagag      60
tcctacatta agagtaaagt aaatacagga actgattttg atggtttata tgggtatcag     120
tgtatggact tagcagtaga ttatatttac catgtaacag atggtaaaat aagaatgtgg     180
ggtaatgcta aggatgcgat aaataactct tttggtggta ctgctacggt atataaaaac    240
taccctgctt ttagacctaa gtacggtgat gtagtcgtat ggactactgg taattttgca    300
acttatggtc atatcgcaat agttactaac cctgacccct atggagaccct tcaatatgtt   360 acagttcttg aacaaaactg gaacggtaac gggatttata aaccgagttt agctacaatc    420
agaacacacg attacacagg aattacacat tttattaaag acgcaaagaa agatgaaaaa    480
tcacaagtat gtagtggttt ggctatggaa aaatatgaca ttacaaattt aaatgctaaa    540
caagataaat caagaatgg gagcgtgaaa gagttgaaac atatctattc aaaccatatt    600
aaaggtaaca agattacagc accaaaacct agtattcaag gtgtggtcat ccacaatgat    660
tatggtagta tgacacctag tcaatactta ccatggttat atgcacgtga gataacggt    720 acacacgtta acggttgggc tagtgtttat gcaaatagaa acgaagtgct ttggtatcat    780
ccgacagact acgtagagtg gcattgtggt aatcaatggg caaatgctaa cttaatcgga    840
tttgaagtgt gtgagtcgta tcctggtaga atctcggaca aattattctt agaaaatgaa    900
gaagcgacat tgaaagtagc tgcggatgtg atgaagtcgt acggattacc agttaatcgc    960
aacactgtac gtctgcataa cgaattcttc ggaacttctt gtccacatcg ttcgtgggac   1020
ttgcatgttg gcaaaggtga gccttacaca actactaata ttaataaaat gaaagactac   1080
ttcatcaaac gcatcaaaca ttattatgac ggtggaaagc tagaagtaag caaagcagca   1140
actatcaaac aatctgacgt taagcaagaa gttaaaaagc aagaagcaaa acaaattgtg   1200
aaagcaacag atgctgcaac acatgaacat tcagcacaat ggttgaataa ttacaaaaaa   1260
ggatatggtt acggtcctta tccattaggt ataaatggcg gtatgcacta cggagttgat   1320
ttttttatga atattggaac accagtaaaa gctatttcaa gcggaaaaat agttgaagct   1380
ggttggagta attacggagg aggtaatcaa ataggtctta ttgaaaatga tggagtgcat   1440
agacaatggt atatgcatct aagtaaatat aatgttaaag taggagatta tgtcaaagct   1500
ggtcaaataa tcggttggtc tggaagcact ggttattcta cagcaccaca tttacacttc   1560
```

```
caaagaatgg ttaattcatt ttcaaattca actgcccaag atccaatgcc tttcttaaag    1620
agcgcaggat atggaaaagc aggtggtaca gtaactccaa cgccgaatac aggttggaaa    1680
cagaataaag atggcatttg gtataaagct gaacatgctt cgttcacagt gacagcacca    1740
gagggaatta tcacaagata caaaggtcct tggactggtc acccacaagc tggtgtatta    1800
caaaaaggtc aaacgattaa atatgatgag gttcaaaaat ttgacggtca tgtttgggta    1860
tcgtgggaaa cgtttgaggg cgaaactgta tacatgccgg tacgcacatg ggacgctaaa    1920
actggtaaag ttggtaagtt gtggggcgaa attaaataa                           1959

<210> SEQ ID NO 48
<211> LENGTH: 1554
<212> TYPE: DNA
<213> ORGANISM: artificial
<220> FEATURE:
<223> OTHER INFORMATION: His-tagged M23-LST_Ami2638_CBD2638

<400> SEQUENCE: 48
atgagaggat cgcatcacca tcaccatcac ggatccgctg caacacatga acattcagca      60
caatggttga ataattacaa aaaaggatat ggttacggtc cttatccatt aggtataaat     120
ggcggtatgc actacggagt tgattttttt atgaatattg gaacaccagt aaaagctatt     180
tcaagcggaa aaatagttga agctggttgg agtaattacg gaggaggtaa tcaaataggt     240
cttattgaaa atgatggagt gcatagacaa tggtatatgc atctaagtaa atataatgtt     300
aaagtaggag attatgtcaa agctggtcaa ataatcggtt ggtctggaag cactggttat     360
tctacagcac acatttaca cttccaaaga atggttaatt cattttcaaa ttcaactgcc      420
caagatccaa tgcctttctt aaagagcgca ggatatggaa aagcaggtgg tacagtaact     480
ccaacgccga atacaggtga gctcttacgc cctaaagacg caagaaaga tgaaaaatca      540 caagtatgta gtggtttggc tatggaaaaa tatgacatta caaatttaaa tgctaaacaa     600
gataaatcaa agaatgggag cgtgaaagag ttgaaacata tctattcaaa ccatattaaa     660
ggtaacaaga ttacagcacc aaaacctagt attcaaggtg tggtcatcca caatgattat     720
ggtagtatga cacctagtca atacttacca tggttatatg cacgtgagaa taacggtaca     780
cacgttaacg gttgggctag tgtttatgca aatagaaacg aagtgctttg gtatcatccg     840
acagactacg tagagtggca ttgtggtaat caatgggcaa atgctaactt aatcggattt     900
gaagtgtgtg agtcgtatcc tggtagaatc tcggacaaat tattcttaga aaatgaagaa     960
gcgacattga aagtagctgc ggatgtgatg aagtcgtacg gattaccagt taatcgcaac    1020
actgtacgtc tgcataacga attcttcgga acttcttgtc cacatcgttc gtgggacttg    1080
catgttggca aaggtgagcc ttacacaact actaatatta taaaaatgaa agactacttc    1140
atcaaacgca tcaaacatta ttatgacggt ggaaagctag aagtaagcaa agcagcaact    1200
atcaaacaat ctgacgttaa gcaagaagtt aaaaagcaag aagcaaaaca aattgtgaaa    1260
gcaacagatt ggaaacagaa taagatggca tttggtata aagctgaaca tgcttcgttc     1320
acagtgacag caccagaggg aattatcaca agatacaaag gtccttggac tggtcaccca    1380
caagctggtg tattacaaaa aggtcaaacg attaaatatg atgaggttca aaaatttgac    1440
ggtcatgttt gggtatcgtg ggaaacgttt gagggcgaaa ctgtatacat gccggtacgc    1500
acatgggacg ctaaaactgg taaagttggt aagttgtggg gcgaaattaa ataa          1554

<210> SEQ ID NO 49
<211> LENGTH: 1887
```

<212> TYPE: DNA
<213> ORGANISM: artificial
<220> FEATURE:
<223> OTHER INFORMATION: His-tagged M23-2638_Ami2638_CBD2638_CBD2638

<400> SEQUENCE: 49

```
atgagaggat cgcatcacca tcaccatcac ggatccatgc taactgctat tgactatctt      60
acgaaaaaag gttggaaaat atcatctgac cctcgcactt acgatggtta ccctaaaaac     120
tacggctaca gaaattacca tgaaaacggc attaattatg atgagttttg tggtggttat     180
catagagctt ttgatgttta cagtaacgaa actaacgacg tgcctgctgt tactagcgga     240
acagttattg aagcaaacga ttacggtaat tttggtggta cattcgttat tagagacgct     300
aacgataacg attggatata tgggcatcta caacgtggct caatgcgatt tgttgtaggc     360
gacaaagtca atcaaggtga cattattggt ttacaaggta atagcaacta ttacgacaat     420
cctatgagtg tacatttaca tttacaatta cgccctaaag acgcaaagaa agatgaaaaa     480
tcacaagtat gtagtggttt ggctatggaa aaatatgaca ttacaaattt aaatgctaaa     540
caagataaat caagaatgg gagcgtgaaa gagttgaaac atatctattc aaaccatatt     600
aaaggtaaca agattacagc accaaaacct agtattcaag gtgtggtcat ccacaatgat     660
tatggtagta tgacacctag tcaatactta ccatggttat atgcacgtga gaataacggt     720
acacacgtta acggttgggc tagtgtttat gcaaatagaa acgaagtgct ttggtatcat     780
ccgacagact acgtagagtg gcattgtggt aatcaatggg caaatgctaa cttaatcgga     840
tttgaagtgt gtgagtcgta tcctggtaga atctcggaca aattattctt agaaaatgaa     900
gaagcgacat tgaaagtagc tgcggatgtg atgaagtcgt acggattacc agttaatcgc     960
aacactgtac gtctgcataa cgaattcttc ggaacttctt gtccacatcg ttcgtgggac    1020
ttgcatgttg gcaaaggtga gccttacaca actactaata ttaataaaat gaaagactac    1080
ttcatcaaac gcatcaaaca ttattatgac ggtggaaagc tagaagtaag caaagcagca    1140
actatcaaac aatctgacgt taagcaagaa gttaaaaagc aagaagcaaa acaaattgtg    1200
aaagcaacag attggaaaca gaataaagat ggcatttggt ataaagctga acatgcttcg    1260
ttcacagtga cagcaccaga gggaattatc acaagataca aaggtccttg gactggtcac    1320
ccacaagctg gtgtattaca aaaggtcaa acgattaaat atgatgaggt tcaaaaattt    1380
gacggtcatg tttgggtatc gtgggaaacg tttgagggcg aaactgtata catgccggta    1440
cgcacatggg acgctaaaac tggtaaagtt ggtaagttgt ggggcgaaat taaagagctc    1500
ggtggaaagc tagaagtaag caaagcagca actatcaaac aatctgacgt taagcaagaa    1560
gttaaaaagc aagaagcaaa acaaattgtg aaagcaacag attggaaaca gaataaagat    1620
ggcatttggt ataaagctga acatgcttcg ttcacagtga cagcaccaga gggaattatc    1680
acaagataca aaggtccttg gactggtcac ccacaagctg gtgtattaca aaaggtcaa    1740
acgattaaat atgatgaggt tcaaaaattt gacggtcatg tttgggtatc gtgggaaacg    1800
tttgagggcg aaactgtata catgccggta cgcacatggg acgctaaaac tggtaaagtt    1860
ggtaagttgt ggggcgaaat taaataa                                        1887
```

<210> SEQ ID NO 50
<211> LENGTH: 3461
<212> TYPE: DNA
<213> ORGANISM: artificial
<220> FEATURE:
<223> OTHER INFORMATION: pQE-30 vector

<400> SEQUENCE: 50

```
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc gcatgcgagc tcggtacccc gggtcgacct     180
gcagccaagc ttaattagct gagcttggac tcctgttgat agatccagta atgacctcag     240
aactccatct ggatttgttc agaacgctcg gttgccgccg ggcgtttttt attggtgaga     300
atccaagcta gcttggcgag attttcagga gctaaggaag ctaaaatgga gaaaaaaatc     360
actggatata ccaccgttga tatatcccaa tggcatcgta aagaacattt tgaggcattt     420
cagtcagttg ctcaatgtac ctataaccag accgttcagc tggatattac ggccttttta     480
aagaccgtaa agaaaaataa gcacaagttt tatccggcct ttattcacat tcttgcccgc     540
ctgatgaatg ctcatccgga atttcgtatg gcaatgaaag acggtgagct ggtgatatgg     600
gatagtgttc acccttgtta caccgttttc catgagcaaa ctgaaacgtt ttcatcgctc     660
tggagtgaat accacgacga tttccggcag tttctacaca tatattcgca agatgtggcg     720
tgttacggtg aaaacctggc ctatttccct aaagggttta ttgagaatat gttttttcgtc   780
tcagccaatc cctgggtgag tttcaccagt tttgatttaa acgtggccaa tatggacaac     840
ttcttcgccc ccgttttcac catgggcaaa tattatacgc aaggcgacaa ggtgctgatg     900
ccgctggcga ttcaggttca tcatgccgtt tgtgatggct tccatgtcgg cagaatgctt     960
aatgaattac aacagtactg cgatgagtgg cagggcgggg cgtaattttt ttaaggcagt    1020
tattggtgcc cttaaacgcc tggggtaatg actctctagc ttgaggcatc aaataaaacg    1080
aaaggctcag tcgaaagact gggcctttcg ttttatctgt tgtttgtcgg tgaacgctct    1140
cctgagtagg acaaatccgc cctctagagc tgcctcgcgc gtttcggtga tgacggtgaa    1200
aacctctgac acatgcagct cccggagacg gtcacagctt gtctgtaagc ggatgccggg    1260
agcagacaag cccgtcaggg cgcgtcagcg ggtgttggcg ggtgtcgggg cgcagccatg    1320
acccagtcac gtagcgatag cggagtgtat actggcttaa ctatgcggca tcagagcaga    1380
ttgtactgag agtgcaccat atgcggtgtg aaataccgca cagatgcgta aggagaaaat    1440
accgcatcag gcgctcttcc gcttcctcgc tcactgactc gctgcgctcg gtcgttcggc    1500
tgcggcgagc ggtatcagct cactcaaagg cggtaatacg gttatccaca gaatcagggg    1560
ataacgcagg aaagaacatg tgagcaaaag gccagcaaaa ggccaggaac cgtaaaaagg    1620
ccgcgttgct ggcgtttttc cataggctcc gcccccctga cgagcatcac aaaaatcgac    1680
gctcaagtca gaggtggcga aacccgacag gactataaag ataccaggcg tttccccctg    1740
gaagctccct cgtgcgctct cctgttccga ccctgccgct taccggatac ctgtccgcct    1800
ttctcccttc gggaagcgtg cgctttctc atagctcacg ctgtaggtat ctcagttcgg    1860
tgtaggtcgt tcgctccaag ctgggctgtg tgcacgaacc ccccgttcag cccgaccgct    1920
gcgccttatc cggtaactat cgtcttgagt ccaacccggt aagacacgac ttatcgccac    1980
tggcagcagc cactggtaac aggattagca gagcgaggta tgtaggcggt gctacagagt    2040
tcttgaagtg gtggcctaac tacggctaca ctagaaggac agtatttggt atctgcgctc    2100
tgctgaagcc agttaccttc ggaaaaagag ttggtagctc ttgatccggc aaacaaacca    2160
ccgctggtag cggtggtttt tttgtttgca agcagcagat tacgcgcaga aaaaaaggat    2220
ctcaagaaga tcctttgatc ttttctacgg ggtctgacgc tcagtggaac gaaaactcac    2280
gttaagggat tttggtcatg agattatcaa aaaggatctt cacctagatc cttttaaatt    2340
```

```
aaaaatgaag ttttaaatca atctaaagta tatatgagta aacttggtct gacagttacc    2400
aatgcttaat cagtgaggca cctatctcag cgatctgtct atttcgttca tccatagttg    2460
cctgactccc cgtcgtgtag ataactacga tacgggaggg cttaccatct ggccccagtg    2520
ctgcaatgat accgcgagac ccacgctcac cggctccaga tttatcagca ataaaccagc    2580
cagccggaag ggccgagcgc agaagtggtc ctgcaacttt atccgcctcc atccagtcta    2640
ttaattgttg ccgggaagct agagtaagta gttcgccagt taatagtttg cgcaacgttg    2700
ttgccattgc tacaggcatc gtggtgtcac gctcgtcgtt tggtatggct tcattcagct    2760
ccggttccca acgatcaagg cgagttacat gatcccccat gttgtgcaaa aaagcggtta    2820
gctccttcgg tcctccgatc gttgtcagaa gtaagttggc cgcagtgtta tcactcatgg    2880
ttatggcagc actgcataat tctcttactg tcatgccatc cgtaagatgc ttttctgtga    2940
ctggtgagta ctcaaccaag tcattctgag aatagtgtat gcggcgaccg agttgctctt    3000
gcccggcgtc aatacgggat aataccgcgc cacatagcag aactttaaaa gtgctcatca    3060
ttggaaaacg ttcttcgggg cgaaaactct caaggatctt accgctgttg agatccagtt    3120
cgatgtaacc cactcgtgca cccaactgat cttcagcatc ttttactttc accagcgttt    3180
ctgggtgagc aaaaacagga aggcaaaatg ccgcaaaaaa gggaataagg gcgacacgga    3240
aatgttgaat actcatactc ttcctttttc aatattattg aagcatttat cagggttatt    3300
gtctcatgag cggatacata tttgaatgta tttagaaaaa taaacaaata ggggttccgc    3360
gcacatttcc ccgaaaagtg ccacctgacg tctaagaaac cattattatc atgacattaa    3420
cctataaaaa taggcgtatc acgaggccct ttcgtcttca c                       3461

<210> SEQ ID NO 51
<211> LENGTH: 127
<212> TYPE: PRT
<213> ORGANISM: Staphylococcus aureus bacteriophage 2638a

<400> SEQUENCE: 51

Gly Lys Leu Glu Val Ser Lys Ala Ala Thr Ile Lys Gln Ser Asp Val
1               5                   10                  15

Lys Gln Glu Val Lys Lys Gln Glu Ala Lys Gln Ile Val Lys Ala Thr
            20                  25                  30

Asp Trp Lys Gln Asn Lys Asp Gly Ile Trp Tyr Lys Ala Glu His Ala
        35                  40                  45

Ser Phe Thr Val Thr Ala Pro Glu Gly Ile Ile Thr Arg Tyr Lys Gly
    50                  55                  60

Pro Trp Thr Gly His Pro Gln Ala Gly Val Leu Gln Lys Gly Gln Thr
65                  70                  75                  80

Ile Lys Tyr Asp Glu Val Gln Lys Phe Asp Gly His Val Trp Val Ser
                85                  90                  95

Trp Glu Thr Phe Glu Gly Glu Thr Val Tyr Met Pro Val Arg Thr Trp
            100                 105                 110

Asp Ala Lys Thr Gly Lys Val Gly Lys Leu Trp Gly Glu Ile Lys
        115                 120                 125

<210> SEQ ID NO 52
<211> LENGTH: 106
<212> TYPE: PRT
<213> ORGANISM: Staphylococcus simulans

<400> SEQUENCE: 52
```

```
Gly Lys Ala Gly Gly Thr Val Thr Pro Thr Pro Asn Thr Gly Trp Lys
1               5                   10                  15

Thr Asn Lys Tyr Gly Thr Leu Tyr Lys Ser Glu Ser Ala Ser Phe Thr
            20                  25                  30

Pro Asn Thr Asp Ile Ile Thr Arg Thr Thr Gly Pro Phe Arg Ser Met
            35                  40                  45

Pro Gln Ser Gly Val Leu Lys Ala Gly Gln Thr Ile His Tyr Asp Glu
        50                  55                  60

Val Met Lys Gln Asp Gly His Val Trp Val Tyr Thr Gly Asn Ser
65                  70                  75                  80

Gly Gln Arg Ile Tyr Leu Pro Val Arg Thr Trp Asn Lys Ser Thr Asn
                85                  90                  95

Thr Leu Gly Val Leu Trp Gly Thr Ile Lys
            100                 105
```

<210> SEQ ID NO 53
<211> LENGTH: 190
<212> TYPE: PRT
<213> ORGANISM: Staphylococcus aureus bacteriophage 2638a

<400> SEQUENCE: 53

```
Met Leu Thr Ala Ile Asp Tyr Leu Thr Lys Lys Gly Trp Lys Ile Ser
1               5                   10                  15

Ser Asp Pro Arg Thr Tyr Asp Gly Tyr Pro Lys Asn Tyr Gly Tyr Arg
            20                  25                  30

Asn Tyr His Glu Asn Gly Ile Asn Tyr Asp Glu Phe Cys Gly Gly Tyr
            35                  40                  45

His Arg Ala Phe Asp Val Tyr Ser Asn Glu Thr Asn Asp Val Pro Ala
        50                  55                  60

Val Thr Ser Gly Thr Val Ile Glu Ala Asn Asp Tyr Gly Asn Phe Gly
65                  70                  75                  80

Gly Thr Phe Val Ile Arg Asp Ala Asn Asp Asn Asp Trp Ile Tyr Gly
                85                  90                  95

His Leu Gln Arg Gly Ser Met Arg Phe Val Val Gly Asp Lys Val Asn
            100                 105                 110

Gln Gly Asp Ile Ile Gly Leu Gln Gly Asn Ser Asn Tyr Tyr Asp Asn
            115                 120                 125

Pro Met Ser Val His Leu His Leu Gln Leu Arg Pro Lys Asp Ala Lys
        130                 135                 140

Lys Asp Glu Lys Ser Gln Val Cys Ser Gly Leu Ala Met Glu Lys Tyr
145                 150                 155                 160

Asp Ile Thr Asn Leu Asn Ala Lys Gln Asp Lys Ser Lys Asn Gly Ser
                165                 170                 175

Val Lys Glu Leu Lys His Ile Tyr Ser Asn His Ile Lys Gly
            180                 185                 190
```

<210> SEQ ID NO 54
<211> LENGTH: 154
<212> TYPE: PRT
<213> ORGANISM: Staphylococcus simulans

<400> SEQUENCE: 54

```
Ala Ala Thr His Glu His Ser Ala Gln Trp Leu Asn Asn Tyr Lys Lys
1               5                   10                  15

Gly Tyr Gly Tyr Gly Pro Tyr Pro Leu Gly Ile Asn Gly Gly Met His
            20                  25                  30
```

```
Tyr Gly Val Asp Phe Phe Met Asn Ile Gly Thr Pro Val Lys Ala Ile
             35                  40                  45

Ser Ser Gly Lys Ile Val Glu Ala Gly Trp Ser Asn Tyr Gly Gly Gly
 50                  55                  60

Asn Gln Ile Gly Leu Ile Glu Asn Asp Gly Val His Arg Gln Trp Tyr
 65                  70                  75                  80

Met His Leu Ser Lys Tyr Asn Val Lys Val Gly Asp Tyr Val Lys Ala
                 85                  90                  95

Gly Gln Ile Ile Gly Trp Ser Gly Ser Thr Gly Tyr Ser Thr Ala Pro
                100                 105                 110

His Leu His Phe Gln Arg Met Val Asn Ser Phe Ser Asn Ser Thr Ala
                115                 120                 125

Gln Asp Pro Met Pro Phe Leu Lys Ser Ala Gly Tyr Gly Lys Ala Gly
130                 135                 140

Gly Thr Val Thr Pro Thr Pro Asn Thr Gly
145                 150
```

<210> SEQ ID NO 55
<211> LENGTH: 246
<212> TYPE: PRT
<213> ORGANISM: Staphylococcus aureus bacteriophage 2638a

<400> SEQUENCE: 55

```
Glu Lys Ser Gln Val Cys Ser Gly Leu Ala Met Glu Lys Tyr Asp Ile
 1               5                  10                  15

Thr Asn Leu Asn Ala Lys Gln Asp Lys Ser Lys Asn Gly Ser Val Lys
                 20                  25                  30

Glu Leu Lys His Ile Tyr Ser Asn His Ile Lys Gly Asn Lys Ile Thr
                 35                  40                  45

Ala Pro Lys Pro Ser Ile Gln Gly Val Val Ile His Asn Asp Tyr Gly
 50                  55                  60

Ser Met Thr Pro Ser Gln Tyr Leu Pro Trp Leu Tyr Ala Arg Glu Asn
 65                  70                  75                  80

Asn Gly Thr His Val Asn Gly Trp Ala Ser Val Tyr Ala Asn Arg Asn
                 85                  90                  95

Glu Val Leu Trp Tyr His Pro Thr Asp Tyr Val Glu Trp His Cys Gly
                100                 105                 110

Asn Gln Trp Ala Asn Ala Asn Leu Ile Gly Phe Glu Val Cys Glu Ser
                115                 120                 125

Tyr Pro Gly Arg Ile Ser Asp Lys Leu Phe Leu Glu Asn Glu Glu Ala
130                 135                 140

Thr Leu Lys Val Ala Ala Asp Val Met Lys Ser Tyr Gly Leu Pro Val
145                 150                 155                 160

Asn Arg Asn Thr Val Arg Leu His Asn Glu Phe Phe Gly Thr Ser Cys
                165                 170                 175

Pro His Arg Ser Trp Asp Leu His Val Gly Lys Gly Glu Pro Tyr Thr
                180                 185                 190

Thr Thr Asn Ile Asn Lys Met Lys Asp Tyr Phe Ile Lys Arg Ile Lys
                195                 200                 205

His Tyr Tyr Asp Gly Gly Lys Leu Glu Val Ser Lys Ala Ala Thr Ile
            210                 215                 220

Lys Gln Ser Asp Val Lys Gln Glu Val Lys Gln Glu Ala Lys Gln
225                 230                 235                 240

Ile Val Lys Ala Thr Asp
            245
```

<210> SEQ ID NO 56
<211> LENGTH: 220
<212> TYPE: PRT
<213> ORGANISM: Staphylococcus aureus phage phi 11

<400> SEQUENCE: 56

Pro Lys Lys Glu Thr Ala Lys Pro Gln Pro Lys Ala Val Glu Leu Lys
1               5                   10                  15

Ile Ile Lys Asp Val Val Lys Gly Tyr Asp Leu Pro Lys Arg Gly Ser
            20                  25                  30

Asn Pro Lys Gly Ile Val Ile His Asn Asp Ala Gly Ser Lys Gly Ala
        35                  40                  45

Thr Ala Glu Ala Tyr Arg Asn Gly Leu Val Asn Ala Pro Leu Ser Arg
    50                  55                  60

Leu Glu Ala Gly Ile Ala His Ser Tyr Val Ser Gly Asn Thr Val Trp
65                  70                  75                  80

Gln Ala Leu Asp Glu Ser Gln Val Gly Trp His Thr Ala Asn Gln Ile
                85                  90                  95

Gly Asn Lys Tyr Tyr Tyr Gly Ile Glu Val Cys Gln Ser Met Gly Ala
            100                 105                 110

Asp Asn Ala Thr Phe Leu Lys Asn Glu Gln Ala Thr Phe Gln Glu Cys
        115                 120                 125

Ala Arg Leu Leu Lys Lys Trp Gly Leu Pro Ala Asn Arg Asn Thr Ile
    130                 135                 140

Arg Leu His Asn Glu Phe Thr Ser Thr Ser Cys Pro His Arg Ser Ser
145                 150                 155                 160

Val Leu His Thr Gly Phe Asp Pro Val Thr Arg Gly Leu Leu Pro Glu
                165                 170                 175

Asp Lys Arg Leu Gln Leu Lys Asp Tyr Phe Ile Lys Gln Ile Arg Ala
            180                 185                 190

Tyr Met Asp Gly Lys Ile Pro Val Ala Thr Val Ser Asn Glu Ser Ser
        195                 200                 205

Ala Ser Ser Asn Thr Val Lys Pro Val Ala Ser Ala
    210                 215                 220

<210> SEQ ID NO 57
<211> LENGTH: 206
<212> TYPE: PRT
<213> ORGANISM: Staphylococcus aureus phage phi 11

<400> SEQUENCE: 57

Met Ser Ile Ile Met Glu Val Ala Thr Met Gln Ala Lys Leu Thr Lys
1               5                   10                  15

Asn Glu Phe Ile Glu Trp Leu Lys Thr Ser Glu Gly Lys Gln Phe Asn
            20                  25                  30

Val Asp Leu Trp Tyr Gly Phe Gln Cys Phe Asp Tyr Ala Asn Ala Gly
        35                  40                  45

Trp Lys Val Leu Phe Gly Leu Leu Lys Gly Leu Gly Ala Lys Asp
    50                  55                  60

Ile Pro Phe Ala Asn Asn Phe Asp Gly Leu Ala Thr Val Tyr Gln Asn
65                  70                  75                  80

Thr Pro Asp Phe Leu Ala Gln Pro Gly Asp Met Val Val Phe Gly Ser
                85                  90                  95

Asn Tyr Gly Ala Gly Tyr Gly His Val Ala Trp Val Ile Glu Ala Thr
            100                 105                 110

Leu Asp Tyr Ile Ile Val Tyr Glu Gln Asn Trp Leu Gly Gly Gly Trp
        115                 120                 125

Thr Asp Gly Ile Glu Gln Pro Gly Trp Gly Trp Glu Lys Val Thr Arg
    130                 135                 140

Arg Gln His Ala Tyr Asp Phe Pro Met Trp Phe Ile Arg Pro Asn Phe
145                 150                 155                 160

Lys Ser Glu Thr Ala Pro Arg Ser Val Gln Ser Pro Thr Gln Ala Pro
                165                 170                 175

Lys Lys Glu Thr Ala Lys Pro Gln Pro Lys Ala Val Glu Leu Lys Ile
                180                 185                 190

Ile Lys Asp Val Val Lys Gly Tyr Asp Leu Pro Lys Arg Gly
                195                 200                 205

<210> SEQ ID NO 58
<211> LENGTH: 187
<212> TYPE: PRT
<213> ORGANISM: Staphylococcus phage Twort

<400> SEQUENCE: 58

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Lys Asp Thr Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly
            180                 185

<210> SEQ ID NO 59
<211> LENGTH: 4546
<212> TYPE: DNA
<213> ORGANISM: artificial
<220> FEATURE:
<223> OTHER INFORMATION: pHGFP_CBD2638_c vector

<400> SEQUENCE: 59
ctcgagaaat cataaaaaat ttatttgctt tgtgagcgga taacaattat aatagattca    60
attgtgagcg gataacaatt tcacacagaa ttcattaaag aggagaaatt aactatgaga   120
ggatcgcatc accatcacca tcacggatcc atgagtaaag gagaagaact tttcactgga   180

```
gttgtcccaa ttcttgttga attagatggt gatgttaatg ggcacaaatt ttctgtcagt    240
ggagagggtg aaggtgatgc aacatacgga aaacttaccc ttaaatttat ttgcactact    300
ggaaaactac ctgttccatg ccaacactt gtcactactt tcgcgtatgg tcttcaatgc     360
tttgcgagat acccagatca tatgaaacgg catgactttt tcaagagtgc catgcccgaa    420
ggttatgtac aggaaagaac tatattttc aaagatgacg gaactacaa gacacgtgct     480 gaagtcaagt ttgaaggtga tacccttgtt aatagaatcg agttaaaagg tattgatttt    540
aaagaagatg aaacattct tggacacaaa ttggaataca actataactc acacaatgta    600
tacatcatgg cagacaaaca aaagaatgga atcaaagtta acttcaaaat tagacacaac   660
attgaagatg gaagcgttca actagcagac cattatcaac aaaatactcc aattggcgat    720
ggccctgtcc ttttaccaga caaccattac ctgtccacac aatctgccct tcgaaagat    780 cccaacgaaa agagagacca catggtcctt cttgagtttg taacagctgc tgggattaca   840
catggcatgg atgaactata caagagctc ggtggaaagc tagaagtaag caaagcagca    900
actatcaaac aatctgacgt taagcaagaa gttaaaaagc aagaagcaaa acaaattgtg    960
aaagcaacag attggaaaca gaataaagat ggcatttggt ataaagctga acatgcttcg   1020
ttcacagtga cagcaccaga gggaattatc acaagataca aaggtccttg gactggtcac   1080
ccacaagctg gtgtattaca aaaaggtcaa acgattaaat atgatgaggt tcaaaaattt   1140
gacggtcatg tttgggtatc gtgggaaacg tttgagggcg aaactgtata catgccggta   1200
cgcacatggg acgctaaaac tggtaaagtt ggtaagttgt ggggcgaaat taaataagtc   1260
gacctgcagc caagcttaat tagctgagct tggactcctg ttgatagatc cagtaatgac   1320
ctcagaactc catctggatt tgttcagaac gctcggttgc cgccgggcgt ttttattgg    1380 tgagaatcca agctagcttg gcgagatttt caggagctaa ggaagctaaa atggagaaaa   1440
aaatcactgg atataccacc gttgatatat cccaatggca tcgtaaagaa cattttgagg   1500
catttcagtc agttgctcaa tgtacctata accagaccgt tcagctggat attacggcct   1560
ttttaaagac cgtaaagaaa aataagcaca gttttatcc ggcctttatt cacattcttg    1620
cccgcctgat gaatgctcat ccggaatttc gtatggcaat gaaagacggt gagctggtga   1680
tatgggatag tgttcaccct tgttacaccg ttttccatga gcaaactgaa acgttttcat   1740
cgctctggag tgaataccac gacgatttcc ggcagtttct acacatatat tcgcaagatg   1800
tggcgtgtta cggtgaaaac ctggcctatt tccctaaagg gttattgag aatatgtttt    1860 tcgtctcagc caatccctgg gtgagtttca ccagttttga tttaaacgtg gccaatatgg   1920
acaacttctt cgccccgtt ttcaccatgg gcaaatatta tacgcaaggc gacaaggtgc    1980
tgatgccgct ggcgattcag gttcatcatg ccgtttgtga tggcttccat gtcggcagaa   2040
tgcttaatga attacaacag tactgcgatg agtggcaggg cggggcgtaa ttttttaag    2100 gcagttattg gtgcccttaa acgcctgggg taatgactct ctagcttgag gcatcaaata   2160
aaacgaaagg ctcagtcgaa agactgggcc tttcgtttta tctgttgttt gtcggtgaac   2220
gctctcctga gtaggacaaa tccgccctct agagctgcct cgcgcgtttc ggtgatgacg   2280
gtgaaaacct ctgacacatg cagctcccgg agacggtcac agcttgtctg taagcggatg   2340
ccgggagcag acaagcccgt cagggcgcgt cagcgggtgt tggcgggtgt cggggcgcag   2400
ccatgaccca gtcacgtagc gatagcggag tgtatactgg cttaactatg cggcatcaga   2460
gcagattgta ctgagagtgc accatatgcg gtgtgaaata ccgcacagat gcgtaaggag   2520
aaaataccgc atcaggcgct cttccgcttc ctcgctcact gactcgctgc gctcggtcgt   2580
```

```
tcggctgcgg cgagcggtat cagctcactc aaaggcggta atacggttat ccacagaatc    2640
aggggataac gcaggaaaga acatgtgagc aaaaggccag caaaaggcca ggaaccgtaa    2700
aaaggccgcg ttgctggcgt ttttccatag gctccgcccc cctgacgagc atcacaaaaa    2760
tcgacgctca agtcagaggt ggcgaaaccc gacaggacta taaagatacc aggcgtttcc    2820
ccctggaagc tccctcgtgc gctctcctgt tccgaccctg ccgcttaccg gatacctgtc    2880
cgcctttctc ccttcgggaa gcgtggcgct ttctcatagc tcacgctgta ggtatctcag    2940
ttcggtgtag gtcgttcgct ccaagctggg ctgtgtgcac gaaccccccg ttcagcccga    3000
ccgctgcgcc ttatccggta actatcgtct tgagtccaac ccggtaagac acgacttatc    3060
gccactggca gcagccactg gtaacaggat tagcagagcg aggtatgtag gcggtgctac    3120
agagttcttg aagtggtggc ctaactacgg ctacactaga aggacagtat ttggtatctg    3180
cgctctgctg aagccagtta ccttcggaaa aagagttggt agctcttgat ccggcaaaca    3240
aaccaccgct ggtagcggtg gtttttttgt ttgcaagcag cagattacgc gcagaaaaaa    3300
aggatctcaa gaagatcctt tgatcttttc tacggggtct gacgctcagt ggaacgaaaa    3360
ctcacgttaa gggattttgg tcatgagatt atcaaaaagg atcttcacct agatcctttt    3420
aaattaaaaa tgaagtttta aatcaatcta agtatatat gagtaaactt ggtctgacag    3480
ttaccaatgc ttaatcagtg aggcacctat ctcagcgatc tgtctatttc gttcatccat    3540
agttgcctga ctccccgtcg tgtagataac tacgatacgg gagggcttac catctggccc    3600
cagtgctgca atgataccgc gagacccacg ctcaccggct ccagatttat cagcaataaa    3660
ccagccagcc ggaagggccg agcgcagaag tggtcctgca actttatccg cctccatcca    3720
gtctattaat tgttgccggg aagctagagt aagtagttcg ccagttaata gtttgcgcaa    3780
cgttgttgcc attgctacag gcatcgtggt gtcacgctcg tcgtttggta tggcttcatt    3840
cagctccggt tcccaacgat caaggcgagt tacatgatcc cccatgttgt gcaaaaaagc    3900
ggttagctcc ttcggtcctc cgatcgttgt cagaagtaag ttggccgcag tgttatcact    3960
catggttatg gcagcactgc ataattctct tactgtcatg ccatccgtaa gatgcttttc    4020
tgtgactggt gagtactcaa ccaagtcatt ctgagaatag tgtatgcggc gaccgagttg    4080
ctcttgcccg gcgtcaatac gggataatac cgcgccacat agcagaactt taaaagtgct    4140
catcattgga aaacgttctt cggggcgaaa actctcaagg atcttaccgc tgttgagatc    4200
cagttcgatg taacccactc gtgcacccaa ctgatcttca gcatctttta ctttcaccag    4260
cgtttctggg tgagcaaaaa caggaaggca aaatgccgca aaaaagggaa taagggcgac    4320
acggaaatgt tgaatactca tactcttcct ttttcaatat tattgaagca tttatcaggg    4380
ttattgtctc atgagcggat acatatttga atgtatttag aaaaataaac aatagggggt    4440
tccgcgcaca tttccccgaa aagtgccacc tgacgtctaa gaaaccatta ttatcatgac    4500
attaacctat aaaaataggc gtatcacgag gccctttcgt cttcac               4546
```

<210> SEQ ID NO 60
<211> LENGTH: 1143
<212> TYPE: DNA
<213> ORGANISM: artificial
<220> FEATURE:
<223> OTHER INFORMATION: His-tagged GFP_CBD2638

<400> SEQUENCE: 60

```
atgagaggat cgcatcacca tcaccatcac ggatccatga gtaaaggaga agaacttttc     60
```

```
actggagttg tcccaattct tgttgaatta gatggtgatg ttaatgggca caaattttct      120
gtcagtggag agggtgaagg tgatgcaaca tacggaaaac ttacccttaa atttatttgc      180
actactggaa aactacctgt tccatggcca acacttgtca ctactttcgc gtatggtctt      240
caatgctttg cgagataccc agatcatatg aaacggcatg acttttcaa gagtgccatg       300 cccgaaggtt atgtacagga agaactata tttttcaaag atgacgggaa ctacaagaca       360
cgtgctgaag tcaagtttga aggtgatacc cttgttaata gaatcgagtt aaaaggtatt      420
gattttaaag aagatggaaa cattcttgga cacaaattgg aatacaacta taactcacac      480
aatgtataca tcatggcaga caacaaaag aatggaatca agttaacctt caaaattaga       540
cacaacattg aagatggaag cgttcaacta gcagaccatt atcaacaaaa tactccaatt      600
ggcgatggcc ctgtcctttt accagacaac cattacctgt ccacacaatc tgccctttcg      660
aaagatccca acgaaaagag agaccacatg gtccttcttg agtttgtaac agctgctggg      720
attacacatg gcatggatga actatacaaa gagctcggtg aaagctaga agtaagcaaa       780 gcagcaacta tcaaacaatc tgacgttaag caagaagtta aaaagcaaga agcaaaacaa      840
attgtgaaag caacagattg gaaacagaat aaagatggca tttggtataa agctgaacat      900
gcttcgttca cagtgacagc accagaggga attatcacaa gatacaaagg tccttggact      960
ggtcacccac aagctggtgt attacaaaaa ggtcaaacga ttaaatatga tgaggttcaa      1020
aaatttgacg tcatgtttg gtatcgtgg gaaacgttg agggcgaaac tgtatacatg       1080
ccggtacgca catgggacgc taaaactggt aaagttggta agttgtgggg cgaaattaaa      1140
taa                                                                    1143

<210> SEQ ID NO 61
<211> LENGTH: 1539
<212> TYPE: DNA
<213> ORGANISM: artificial
<220> FEATURE:
<223> OTHER INFORMATION: His-tagged GFP_CBD2638_CBD2638 var.1

<400> SEQUENCE: 61
atgagaggat cgcatcacca tcaccatcac ggatccatga gtaaaggaga agaactttc        60 actggagttg tcccaattct tgttgaatta gatggtgatg ttaatgggca caaattttct      120
gtcagtggag agggtgaagg tgatgcaaca tacggaaaac ttacccttaa atttatttgc      180
actactggaa aactacctgt tccatggcca acacttgtca ctactttcgc gtatggtctt      240
caatgctttg cgagataccc agatcatatg aaacggcatg acttttcaa gagtgccatg       300 cccgaaggtt atgtacagga agaactata tttttcaaag atgacgggaa ctacaagaca       360
cgtgctgaag tcaagtttga aggtgatacc cttgttaata gaatcgagtt aaaaggtatt      420
gattttaaag aagatggaaa cattcttgga cacaaattgg aatacaacta taactcacac      480
aatgtataca tcatggcaga caacaaaag aatggaatca agttaacctt caaaattaga       540
cacaacattg aagatggaag cgttcaacta gcagaccatt atcaacaaaa tactccaatt      600
ggcgatggcc ctgtcctttt accagacaac cattacctgt ccacacaatc tgccctttcg      660
aaagatccca acgaaaagag agaccacatg gtccttcttg agtttgtaac agctgctggg      720
attacacatg gcatggatga actatacaaa gagctcggtg aaagctaga agtaagcaaa       780 gcagcaacta tcaaacaatc tgacgttaag caagaagtta aaaagcaaga agcaaaacaa      840
attgtgaaag caacagattg gaaacagaat aaagatggca tttggtataa agctgaacat      900
gcttcgttca cagtgacagc accagaggga attatcacaa gatacaaagg tccttggact      960
```

```
ggtcacccac aagctggtgt attacaaaaa ggtcaaacga ttaaatatga tgaggttcaa    1020
aaatttgacg gtcatgtttg ggtatcgtgg gaaacgtttg agggcgaaac tgtatacatg    1080
ccggtacgca catgggacgc taaaactggt aaagttggta agttgtgggg cgaaattaaa    1140
gagctcggtg aaagctaga agtaagcaaa gcagcaacta tcaaacaatc tgacgttaag    1200
caagaagtta aaaagcaaga agcaaaacaa attgtgaaag caacagattg gaaacagaat    1260
aaagatggca tttggtataa agctgaacat gcttcgttca cagtgacagc accagaggga    1320
attatcacaa gatacaaagg tccttggact ggtcacccac aagctggtgt attacaaaaa    1380
ggtcaaacga ttaaatatga tgaggttcaa aaatttgacg gtcatgtttg ggtatcgtgg    1440
gaaacgtttg agggcgaaac tgtatacatg ccggtacgca catgggacgc taaaactggt    1500
aaagttggta agttgtgggg cgaaattaaa taagtcgac                          1539

<210> SEQ ID NO 62
<211> LENGTH: 1560
<212> TYPE: DNA
<213> ORGANISM: artificial
<220> FEATURE:
<223> OTHER INFORMATION: Hist-tagged GFP_CBD2638_CBD2638 var. 2

<400> SEQUENCE: 62
atgagaggat cgcatcacca tcaccatcac ggatccatga gtaaaggaga agaacttttc      60
actggagttg tcccaattct tgttgaatta gatggtgatg ttaatgggca caaattttct     120
gtcagtggag agggtgaagg tgatgcaaca tacggaaaac ttacccttaa atttatttgc     180
actactggaa aactacctgt tccatggcca acacttgtca ctactttcgc gtatggtctt     240
caatgctttg cgagataccc agatcatatg aaacagcatg acttttttcaa gagtgccatg     300 cccgaaggtt atgtacagga agaactatat ttttcaaag atgacgggaa ctacaagaca     360
cgtgctgaag tcaagtttga aggtgatacc cttgttaata gaatcgagtt aaaaggtatt    420
gattttaaag aagatggaaa cattcttgga cacaaattgg aatacaacta taactcacac    480
aatgtataca tcatggcaga caaacaaaag aatggaatca agttaacttt caaaattaga    540
cacaacattg aagatggaag cgttcaacta gcagaccatt atcaacaaaa tactccaatt    600
ggcgatggcc ctgtcctttt accagacaac cattacctgt ccacacaatc tgccctttcg    660
aaagatccca acgaaaagag agaccacatg gtccttcttg agtttgtaac agctgctggg    720
attacacatg gcatggatga actatacaaa gagctcggtg aaagctaga agtaagcaaa    780 gcagcaacta tcaaacaatc tgacgttaag caagaagtta aaaagcaaga agcaaaacaa    840
attgtgaaag caacagattg gaaacagaat aaagatggca tttggtataa agctgaacat    900
gcttcgttca cagtgacagc accagaggga attatcacaa gatacaaagg tccttggact    960
ggtcacccac aagctggtgt attacaaaaa ggtcaaacga ttaaatatga tgaggttcaa   1020
aaatttgacg gtcatgtttg ggtatcgtgg gaaacgtttg agggcgaaac tgtatacatg   1080
ccggtacgca catgggacgc taaaactggt aaagttggta agttgtgggg cgaaattaaa   1140
ggtaccggtg aaagctaga agtaagcaaa gcagcaacta tcaaacaatc tgacgttaag   1200
caagaagtta aaaagcaaga agcaaaacaa attgtgaaag caacagattg gaaacagaat   1260
aaagatggca tttggtataa agctgaacat gcttcgttca cagtgacagc accagaggga   1320
attatcacaa gatacaaagg tccttggact ggtcacccac aagctggtgt attacaaaaa   1380
ggtcaaacga ttaaatatga tgaggttcaa aaatttgacg gtcatgtttg ggtatcgtgg   1440
```

```
gaaacgtttg agggcgaaac tgtatacatg ccggtacgca catgggacgc taaaactggt    1500
aaagttggta agttgtgggg cgaaattaaa gtcgacctgc agccaagctt aattagctga    1560

<210> SEQ ID NO 63
<211> LENGTH: 1944
<212> TYPE: DNA
<213> ORGANISM: artificial
<220> FEATURE:
<223> OTHER INFORMATION: His-tagged GFP_CBD2638_CBD2638_CBD2638

<400> SEQUENCE: 63
atgagaggat cgcatcacca tcaccatcac ggatccatga gtaaaggaga agaactttc      60 actggagttg tcccaattct tgttgaatta gatggtgatg ttaatgggca caaattttct    120
gtcagtggag agggtgaagg tgatgcaaca tacggaaaac ttacccttaa atttatttgc    180
actactggaa aactacctgt tccatggcca acacttgtca ctactttcgc gtatggtctt    240
caatgctttg cgagataccc agatcatatg aaacagcatg acttttttcaa gagtgccatg    300 cccgaaggtt atgtacagga agaactatat ttttcaaag atgacggga ctacaagaca    360 cgtgctgaag tcaagtttga aggtgatacc cttgttaata gaatcgagtt aaaaggtatt    420
gattttaaag aagatggaaa cattcttgga cacaaattgg aatacaacta taactcacac    480
aatgtataca tcatggcaga caaacaaaag aatggaatca agttaacttc caaattaga    540 cacaacattg aagatggaag cgttcaacta gcagaccatt atcaacaaaa tactccaatt    600
ggcgatggcc ctgtccttt accagacaac cattacctgt ccacacaatc tgccctttcg    660
aaagatccca cgaaaagag agaccacatg gtccttcttg agtttgtaac agctgctggg    720
attacacatg gcatggatga actatacaaa gagctcggtg aaagctaga agtaagcaaa    780 gcagcaacta tcaaacaatc tgacgttaag caagaagtta aaaagcaaga agcaaaacaa    840
attgtgaaag caacagattg gaaacagaat aaagatggca tttggtataa agctgaacat    900
gcttcgttca cagtgacagc accagaggga attatcacaa gatacaaagg tccttggact    960
ggtcacccac aagctggtgt attacaaaaa ggtcaaacga ttaaatatga tgaggttcaa   1020
aaatttgacg gtcatgtttg ggtatcgtgg gaaacgtttg agggcgaaac tgtatacatg   1080
ccggtacgca catgggacgc taaaactggt aaagttggta agttgtgggg cgaaattaaa   1140
ggtaccggtg aaagctaga agtaagcaaa gcagcaacta tcaaacaatc tgacgttaag   1200
caagaagtta aaaagcaaga agcaaaacaa attgtgaaag caacagattg gaaacagaat   1260
aaagatggca tttggtataa agctgaacat gcttcgttca cagtgacagc accagaggga   1320
attatcacaa gatacaaagg tccttggact ggtcacccac aagctggtgt attacaaaaa   1380
ggtcaaacga ttaaatatga tgaggttcaa aaatttgacg gtcatgtttg ggtatcgtgg   1440
gaaacgtttg agggcgaaac tgtatacatg ccggtacgca catgggacgc taaaactggt   1500
aaagttggta agttgtgggg cgaaattaaa gtcgacggtg aaagctaga agtaagcaaa   1560 gcagcaacta tcaaacaatc tgacgttaag caagaagtta aaaagcaaga agcaaaacaa   1620
attgtgaaag caacagattg gaaacagaat aaagatggca tttggtataa agctgaacat   1680
gcttcgttca cagtgacagc accagaggga attatcacaa gatacaaagg tccttggact   1740
ggtcacccac aagctggtgt attacaaaaa ggtcaaacga ttaaatatga tgaggttcaa   1800
aaatttgacg gtcatgtttg ggtatcgtgg gaaacgtttg agggcgaaac tgtatacatg   1860
ccggtacgca catgggacgc taaaactggt aaagttggta agttgtgggg cgaaattaaa   1920
ctgcagccaa gcttaattag ctga                                          1944
```

<210> SEQ ID NO 64
<211> LENGTH: 380
<212> TYPE: PRT
<213> ORGANISM: artificial
<220> FEATURE:
<223> OTHER INFORMATION: His-tagged GFP_CBD2638

<400> SEQUENCE: 64

Met Arg Gly Ser His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
            35                  40                  45

Ala Thr Tyr Gly Lys Leu Thr Leu Lys Phe Ile Cys Thr Thr Gly Lys
        50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Arg His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Ser Lys Asp Pro Asn
    210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
        275                 280                 285

Gln Asn Lys Asp Gly Ile Trp Tyr Lys Ala Glu His Ala Ser Phe Thr
    290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
            340                 345                 350

Phe Glu Gly Glu Thr Val Tyr Met Pro Val Arg Thr Trp Asp Ala Lys
        355                 360                 365

```
Thr Gly Lys Val Gly Lys Leu Trp Gly Glu Ile Lys
    370             375             380
```

<210> SEQ ID NO 65
<211> LENGTH: 510
<212> TYPE: PRT
<213> ORGANISM: artificial
<220> FEATURE:
<223> OTHER INFORMATION: His-tagged GFP_CBD2638_CBD2638 var.1

<400> SEQUENCE: 65

```
Met Arg Gly Ser His His His His Gly Ser Met Ser Lys Gly
1               5                   10              15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Arg His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Ser Lys Asp Pro Asn
    210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
        275                 280                 285

Gln Asn Lys Asp Gly Ile Trp Tyr Lys Ala Glu His Ala Ser Phe Thr
    290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
            340                 345                 350
```

-continued

```
Phe Glu Gly Glu Thr Val Tyr Met Pro Val Arg Thr Trp Asp Ala Lys
            355                 360                 365

Thr Gly Lys Val Gly Lys Leu Trp Gly Glu Ile Lys Glu Leu Gly Gly
        370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
                405                 410                 415

Trp Lys Gln Asn Lys Asp Gly Ile Trp Tyr Lys Ala Glu His Ala Ser
            420                 425                 430

Phe Thr Val Thr Ala Pro Glu Gly Ile Ile Thr Arg Tyr Lys Gly Pro
        435                 440                 445

Trp Thr Gly His Pro Gln Ala Gly Val Leu Gln Lys Gly Gln Thr Ile
    450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
                485                 490                 495

Ala Lys Thr Gly Lys Val Gly Lys Leu Trp Gly Glu Ile Lys
            500                 505                 510
```

<210> SEQ ID NO 66
<211> LENGTH: 519
<212> TYPE: PRT
<213> ORGANISM: artificial
<220> FEATURE:
<223> OTHER INFORMATION: His-tagged GFP_CBD2638_CBD2638 var. 2

<400> SEQUENCE: 66

```
Met Arg Gly Ser His His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Phe Ala Tyr Gly Leu
65                  70                  75                  80

Gln Cys Phe Ala Arg Tyr Pro Asp His Met Lys Gln His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205
```

-continued

```
Asp Asn His Tyr Leu Ser Thr Gln Ser Ala Leu Ser Lys Asp Pro Asn
            210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
        275                 280                 285

Gln Asn Lys Asp Gly Ile Trp Tyr Lys Ala Glu His Ala Ser Phe Thr
    290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
            340                 345                 350

Phe Glu Gly Glu Thr Val Tyr Met Pro Val Arg Thr Trp Asp Ala Lys
        355                 360                 365

Thr Gly Lys Val Gly Lys Leu Trp Gly Glu Ile Lys Gly Thr Gly Gly
    370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
                405                 410                 415

Trp Lys Gln Asn Lys Asp Gly Ile Trp Tyr Lys Ala Glu His Ala Ser
            420                 425                 430

Phe Thr Val Thr Ala Pro Glu Gly Ile Ile Thr Arg Tyr Lys Gly Pro
        435                 440                 445

Trp Thr Gly His Pro Gln Ala Gly Val Leu Gln Lys Gly Gln Thr Ile
    450                 455                 460

Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
                485                 490                 495

Ala Lys Thr Gly Lys Val Gly Lys Leu Trp Gly Glu Ile Lys Val Asp
            500                 505                 510

Leu Gln Pro Ser Leu Ile Ser
        515

<210> SEQ ID NO 67
<211> LENGTH: 647
<212> TYPE: PRT
<213> ORGANISM: artificial
<220> FEATURE:
<223> OTHER INFORMATION: His-tagged GFP_CBD2638_CBD2638_CBD2638

<400> SEQUENCE: 67

Met Arg Gly Ser His His His His His His Gly Ser Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45
```

-continued

```
Ala Thr Tyr Gly Lys Leu Thr Leu Lys Phe Ile Cys Thr Thr Gly Lys
        50                  55                  60

Leu Pro Val Pro Trp Pro Thr Leu Val Thr Thr Phe Ala Tyr Gly Leu
 65              70                  75                      80

Gln Cys Phe Ala Arg Tyr Pro Asp His Met Lys Gln His Asp Phe Phe
                85                  90                  95

Lys Ser Ala Met Pro Glu Gly Tyr Val Gln Glu Arg Thr Ile Phe Phe
            100                 105                 110

Lys Asp Asp Gly Asn Tyr Lys Thr Arg Ala Glu Val Lys Phe Glu Gly
            115                 120                 125

Asp Thr Leu Val Asn Arg Ile Glu Leu Lys Gly Ile Asp Phe Lys Glu
            130                 135                 140

Asp Gly Asn Ile Leu Gly His Lys Leu Glu Tyr Asn Tyr Asn Ser His
145                 150                 155                 160

Asn Val Tyr Ile Met Ala Asp Lys Gln Lys Asn Gly Ile Lys Val Asn
                165                 170                 175

Phe Lys Ile Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
            195                 200                 205

Asp Asn His Tyr Leu Ser Thr Gln Ser Ala Leu Ser Lys Asp Pro Asn
210                 215                 220

Glu Lys Arg Asp His Met Val Leu Leu Glu Phe Val Thr Ala Ala Gly
225                 230                 235                 240

Ile Thr His Gly Met Asp Glu Leu Tyr Lys Glu Leu Gly Gly Lys Leu
                245                 250                 255

Glu Val Ser Lys Ala Ala Thr Ile Lys Gln Ser Asp Val Lys Gln Glu
            260                 265                 270

Val Lys Lys Gln Glu Ala Lys Gln Ile Val Lys Ala Thr Asp Trp Lys
            275                 280                 285

Gln Asn Lys Asp Gly Ile Trp Tyr Lys Ala Glu His Ala Ser Phe Thr
        290                 295                 300

Val Thr Ala Pro Glu Gly Ile Ile Thr Arg Tyr Lys Gly Pro Trp Thr
305                 310                 315                 320

Gly His Pro Gln Ala Gly Val Leu Gln Lys Gly Gln Thr Ile Lys Tyr
                325                 330                 335

Asp Glu Val Gln Lys Phe Asp Gly His Val Trp Val Ser Trp Glu Thr
            340                 345                 350

Phe Glu Gly Glu Thr Val Tyr Met Pro Val Arg Thr Trp Asp Ala Lys
        355                 360                 365

Thr Gly Lys Val Gly Lys Leu Trp Gly Glu Ile Lys Gly Thr Gly Gly
        370                 375                 380

Lys Leu Glu Val Ser Lys Ala Ala Thr Ile Lys Gln Ser Asp Val Lys
385                 390                 395                 400

Gln Glu Val Lys Lys Gln Glu Ala Lys Gln Ile Val Lys Ala Thr Asp
                405                 410                 415

Trp Lys Gln Asn Lys Asp Gly Ile Trp Tyr Lys Ala Glu His Ala Ser
            420                 425                 430

Phe Thr Val Thr Ala Pro Glu Gly Ile Ile Thr Arg Tyr Lys Gly Pro
            435                 440                 445

Trp Thr Gly His Pro Gln Ala Gly Val Leu Gln Lys Gly Gln Thr Ile
        450                 455                 460
```

```
Lys Tyr Asp Glu Val Gln Lys Phe Asp Gly His Val Trp Val Ser Trp
465                 470                 475                 480

Glu Thr Phe Glu Gly Glu Thr Val Tyr Met Pro Val Arg Thr Trp Asp
                485                 490                 495

Ala Lys Thr Gly Lys Val Gly Lys Leu Trp Gly Glu Ile Lys Val Asp
                500                 505                 510

Gly Gly Lys Leu Glu Val Ser Lys Ala Ala Thr Ile Lys Gln Ser Asp
            515                 520                 525

Val Lys Gln Glu Val Lys Lys Gln Glu Ala Lys Gln Ile Val Lys Ala
        530                 535                 540

Thr Asp Trp Lys Gln Asn Lys Asp Gly Ile Trp Tyr Lys Ala Glu His
545                 550                 555                 560

Ala Ser Phe Thr Val Thr Ala Pro Glu Gly Ile Ile Thr Arg Tyr Lys
                565                 570                 575

Gly Pro Trp Thr Gly His Pro Gln Ala Gly Val Leu Gln Lys Gly Gln
                580                 585                 590

Thr Ile Lys Tyr Asp Glu Val Gln Lys Phe Asp Gly His Val Trp Val
            595                 600                 605

Ser Trp Glu Thr Phe Glu Gly Glu Thr Val Tyr Met Pro Val Arg Thr
    610                 615                 620

Trp Asp Ala Lys Thr Gly Lys Val Gly Lys Leu Trp Gly Glu Ile Lys
625                 630                 635                 640

Leu Gln Pro Ser Leu Ile Ser
                645
```